(12) United States Patent
Rabinovich et al.

(10) Patent No.: US 11,020,478 B2
(45) Date of Patent: Jun. 1, 2021

(54) METHODS FOR MODULATING ANGIOGENESIS OF CANCERS REFRACTORY TO ANTI-VEGF TREATMENT

(71) Applicants: INIS BIOTECH LLC, Milford, DE (US); CONSEJO NACIONAL DE INVESTIGACIONES CIENTÍFICAS Y TÉCNICAS, Buenos Aires (AR); FUNDACIÓN SALES, Buenos Aires (AR)

(72) Inventors: Gabriel Adrian Rabinovich, Buenos Aires (AR); Diego Omar Croci Russo, Buenos Aires (AR); Juan Pablo Cerliani, Buenos Aires (AR); Mariana Salatino, Buenos Aires (AR); Pablo Francisco Hockl, Buenos Aires (AR); Juan Manuel Pérez Sáez, Buenos Aires (AR)

(73) Assignees: Inis Biotech LLC, Milford, DE (US); Consejo Nacional de Investigaciones Científicas y Técnicas, Buenos Aires (AR); Funadción Sales, Buenos Aires (AR)

( * ) Notice: Subject to any disclaimer, the term of this patent is extended or adjusted under 35 U.S.C. 154(b) by 0 days.

(21) Appl. No.: 16/416,996

(22) Filed: May 20, 2019

(65) Prior Publication Data
US 2020/0016266 A1 Jan. 16, 2020

Related U.S. Application Data

(63) Continuation-in-part of application No. 15/100,164, filed as application No. PCT/US2014/067757 on Nov. 26, 2014, now Pat. No. 10,294,295.

(60) Provisional application No. 61/909,942, filed on Nov. 27, 2013.

(51) Int. Cl.
| | | |
|---|---|---|
| A61K 39/395 | (2006.01) |
| C07K 16/18 | (2006.01) |
| C07K 16/28 | (2006.01) |
| C07K 16/22 | (2006.01) |
| C07K 16/30 | (2006.01) |
| A61K 35/00 | (2006.01) |
| A61P 35/00 | (2006.01) |
| A61K 38/17 | (2006.01) |
| A61K 45/06 | (2006.01) |
| A61K 9/00 | (2006.01) |
| A61K 39/00 | (2006.01) |

(52) U.S. Cl.
CPC ...... *A61K 39/39558* (2013.01); *A61K 9/0019* (2013.01); *A61K 38/179* (2013.01); *A61K 39/3955* (2013.01); *A61K 45/06* (2013.01); *A61P 35/00* (2018.01); *C07K 16/2851* (2013.01); *A61K 2039/507* (2013.01); *C07K 2317/33* (2013.01); *C07K 2317/565* (2013.01); *C07K 2317/76* (2013.01); *C07K 2317/92* (2013.01)

(58) Field of Classification Search
CPC ............ A61K 39/39558; A61K 38/179; A61K 45/06; A61K 9/0019; A61K 2039/507; A61K 2039/505; A61K 39/3955; A61P 35/00; A61P 37/02; C07K 16/2851; C07K 2317/92; C07K 2317/76; C07K 2317/33; C07K 2317/565; C07K 2317/34; C07K 2317/21; C07K 2317/622; C07K 2317/73; C07K 16/2863; C07K 16/2482; C07K 16/2848; C07K 16/22; C07K 16/28; C07K 2317/54; C07K 2317/55; C07K 2317/74
See application file for complete search history.

(56) References Cited

U.S. PATENT DOCUMENTS

| | | |
|---|---|---|
| 2004/0121981 A1 | 6/2004 | Chang et al. |
| 2013/0011409 A1 | 1/2013 | Shipp et al. |

FOREIGN PATENT DOCUMENTS

| | | |
|---|---|---|
| WO | 2009/060198 A1 | 5/2009 |
| WO | 2011/060272 A2 | 5/2011 |

OTHER PUBLICATIONS

Lloyd et al., Protein Engineering, Design & Selection 22:159-168 (Year: 2009).*
Edwards et al., J Mol Biol. Nov. 14, 2003;334(1): 103-118 (Year: 2003).*
Croci et al., "Glycosylation-Dependent Lectin-Receptor Interactions Presever Angiogenesis in Anti-VEGF Refractory Tumors," Cell, 2014, 156:744-758.
PCT International Search Report for PCT Application No. PCT/US2014/067757 dated Feb. 26, 2015 (1 page).
European Extended Search Report for EP Application No. 14865112.8 dated Jun. 12, 2017 (8 pages).
Thijssen et al., "Vascular Galectins: Regulators of Tumor Progression and Targets for Cancer Therapy," Cytokine & Growth Factor Reviews, 2013, 24:547-558.

(Continued)

*Primary Examiner* — Phuong Huynh
(74) *Attorney, Agent, or Firm* — Eversheds Sutherland (US) LLP

(57) ABSTRACT

A method for modulating angiogenesis in a cancer or tumor refractory to anti-VEGF, including identifying a cancer cell as being referactory to anti-VEGF, and then contacting the cancer cell refractory to anti-VEGF with an effective amount of an agent that modulates interaction between Gal1 or a Gal1 fragment and the natural binding partner of Gal1 or the Gal1 fragment to thereby modulate angiogenesis.

23 Claims, 22 Drawing Sheets
Specification includes a Sequence Listing.

(56) References Cited

OTHER PUBLICATIONS

Blancher et al., Expert Opion on therapeutic patents 26(5): 537-554, May 2016.
Stancovski et al., PNAS, 88: 8691-8695, 1991.
Golay et al., Archives of Biochemistry and Biophysics 526: 146-153, 2012.
Calvani et al., Cancer Res 68(1): 285-291, Jan. 1, 2008.
Rubinstein et al., Cancer Cell 5: 241-251, Mar. 2004.
Naeve et al., J Biol Chem (published on line Oct. 24, 2011, pp. 1-15.

* cited by examiner

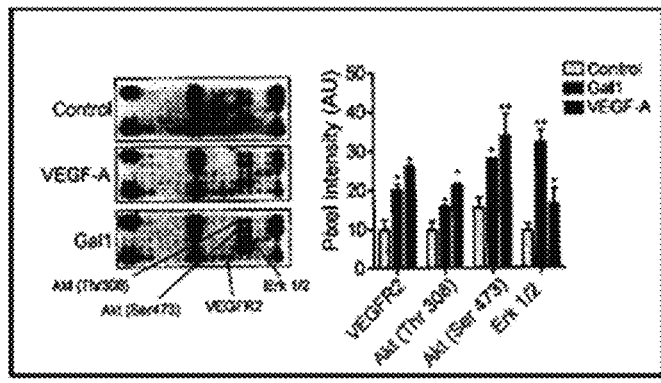
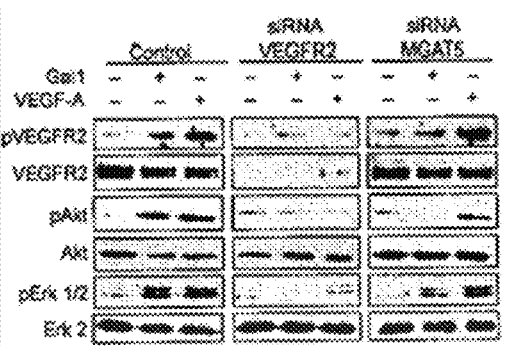
FIG. 2A FIG. 2B
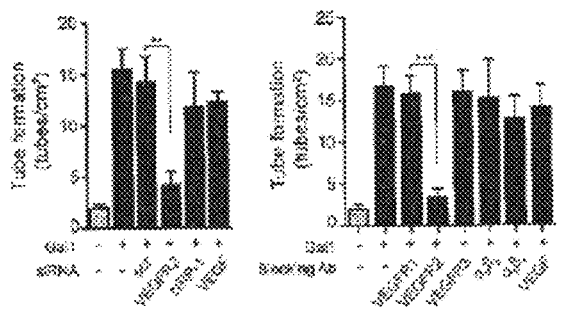
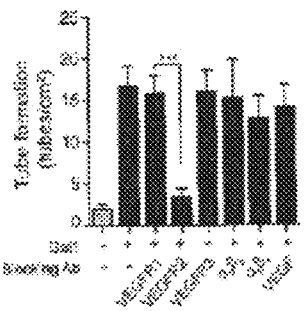
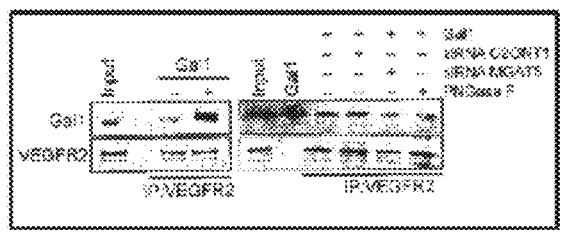
FIG. 2C FIG. 2D FIG. 2E
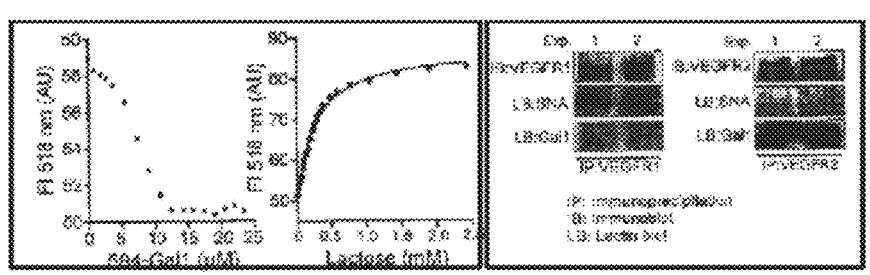
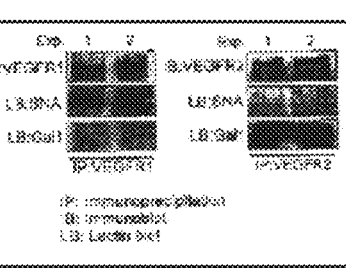
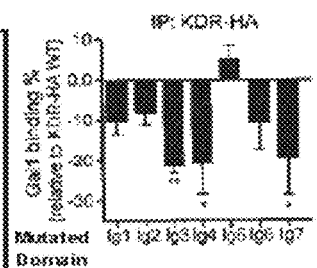
FIG. 2F FIG. 2G FIG. 2H

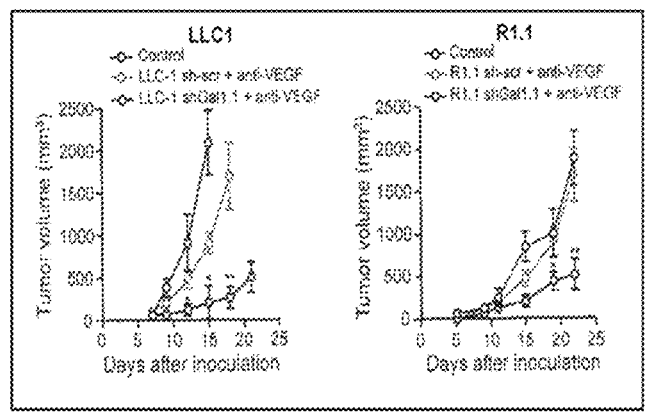
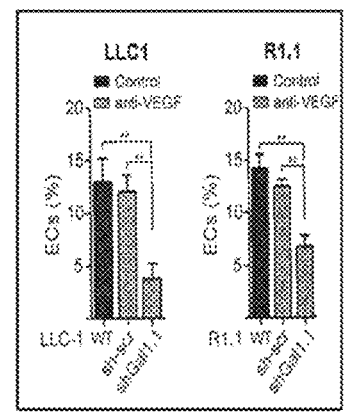
FIG. 4A
FIG. 4B
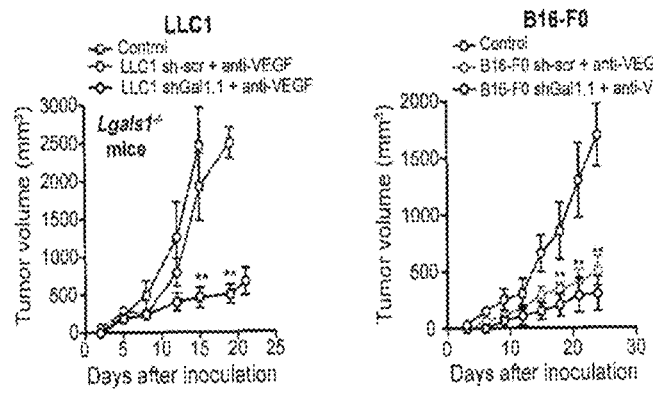
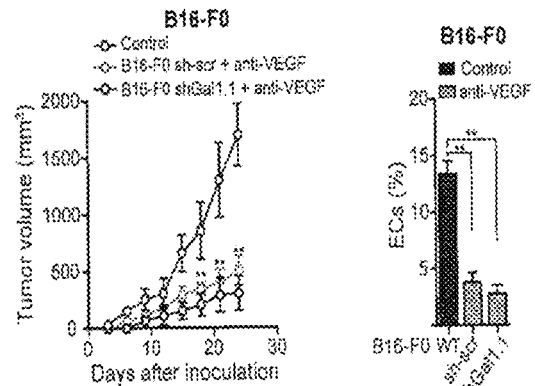
FIG. 4C
FIG. 4D
FIG. 4E

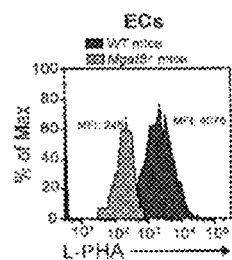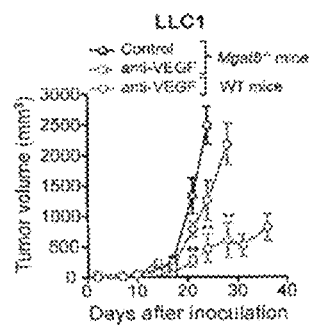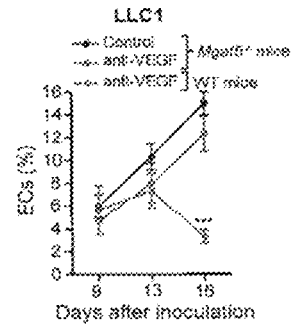
FIG. 5A   FIG. 5B   FIG. 5C
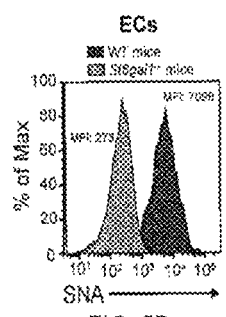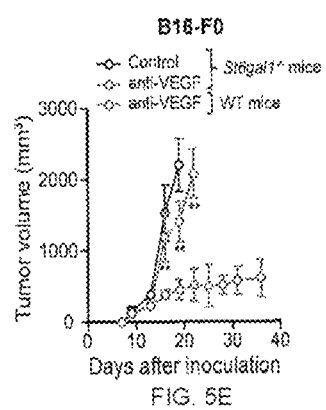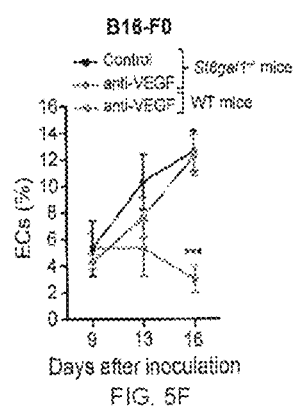
FIG. 5D   FIG. 5E   FIG. 5F
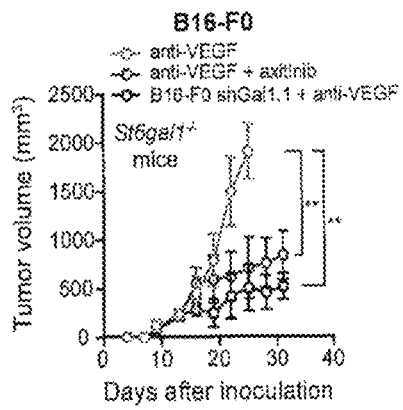
FIG. 5G

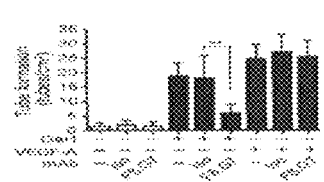 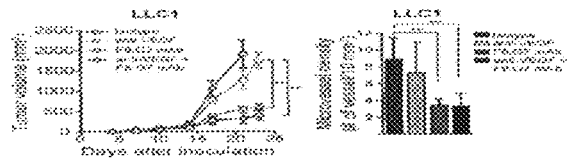
FIG. 6A    FIG. 6B    FIG. 6C
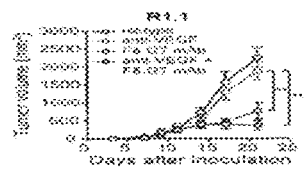 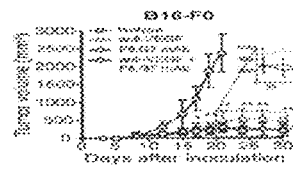 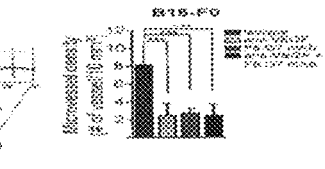
FIG. 6D    FIG. 6E    FIG. 6F
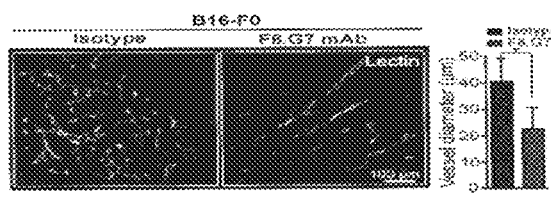 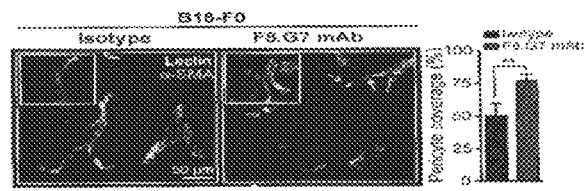
FIG. 6G    FIG. 6H
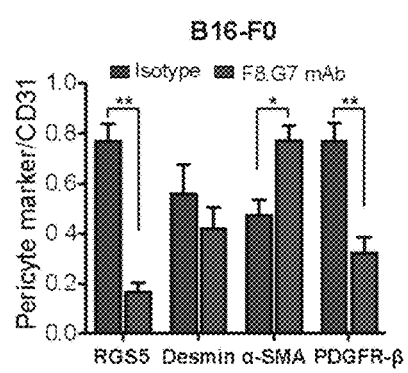
FIG. 6I

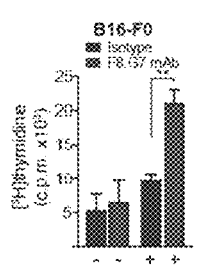
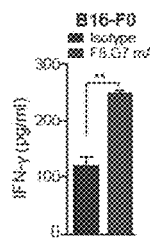
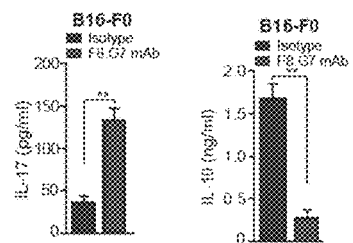
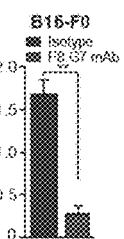
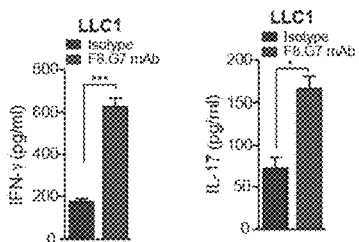
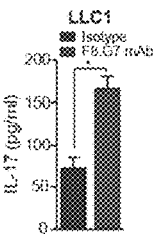
FIG. 7A  FIG. 7B  FIG. 7C  FIG. 7D  FIG. 7E  FIG. 7F
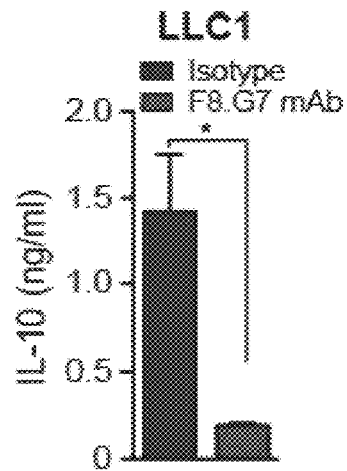
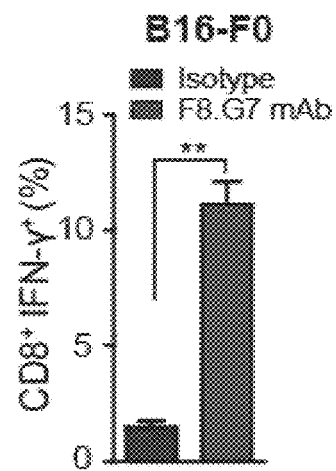
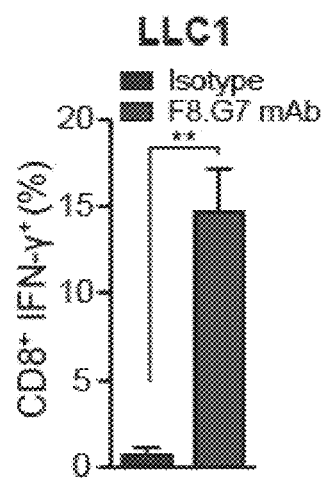
FIG. 7G  FIG. 7H  FIG. 7I
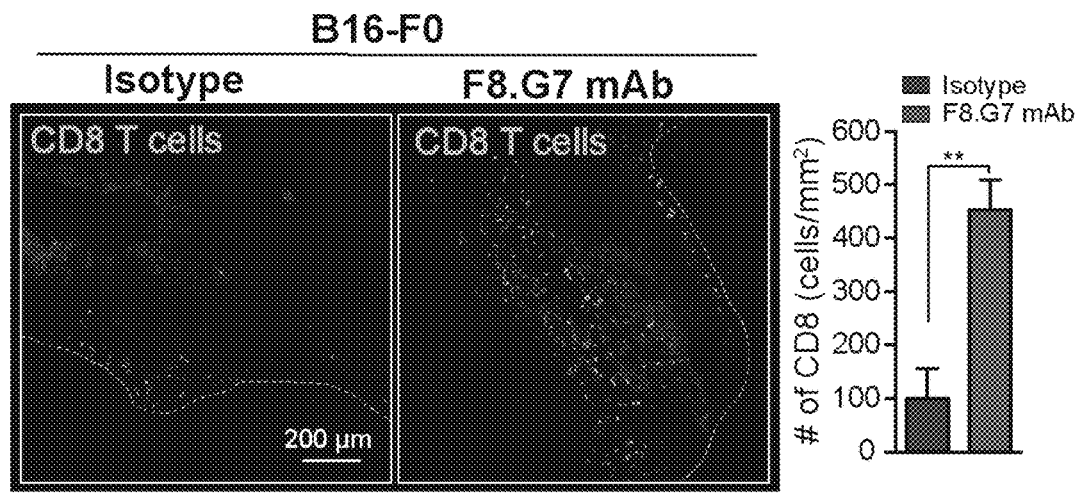
FIG. 7J

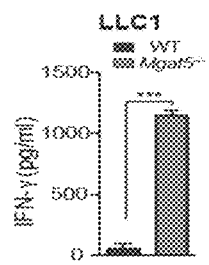 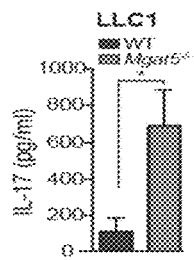 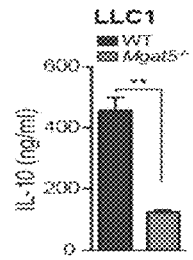 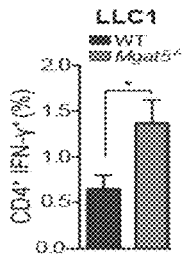
FIG. 7K  FIG. 7L  FIG. 7M  FIG. 7N
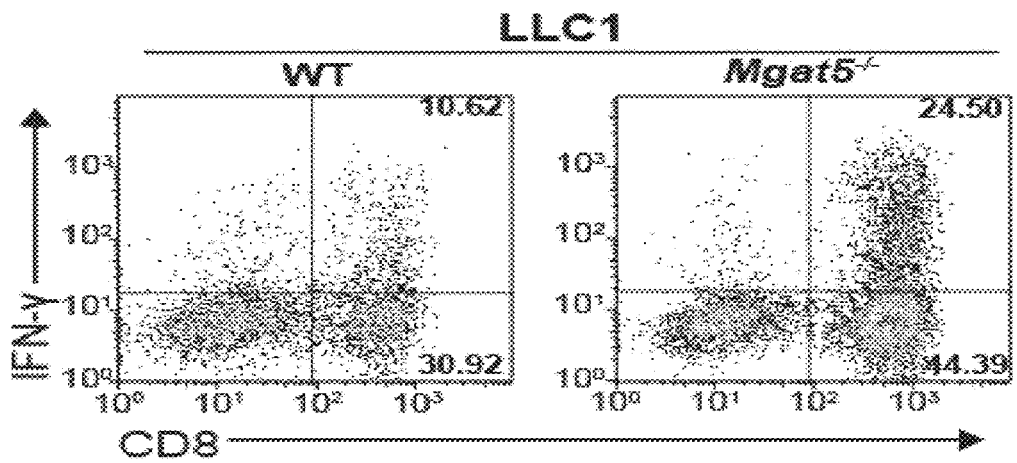
FIG. 7O
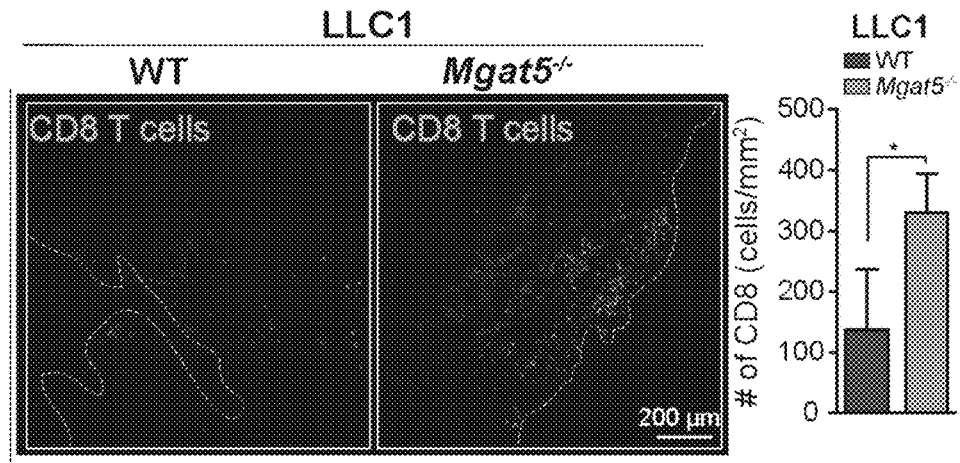
FIG. 7P

METHODS FOR MODULATING ANGIOGENESIS OF CANCERS REFRACTORY TO ANTI-VEGF TREATMENT

CROSS-REFERENCE TO RELATED APPLICATION

This application is a continuation-in-part of U.S. application Ser. No. 15/100,164, filed May 27, 2016, which claims the priority benefit of PCT/US2014/067757, filed Nov. 26, 2014, which claims the priority benefit of U.S. Provisional Application No. 61/909,942, filed on Nov. 27, 2013. The contents of the prior applications are hereby incorporated by reference herein in their entireties.

SEQUENCE LISTING

The instant application contains a Sequence Listing which has been filed electronically in ASCII format and is hereby incorporated by reference in its entirety. Said ASCII copy, created on Oct. 12, 2020, is named 33858-0024 SL.txt and is 38,347 bytes in size.

BACKGROUND

Genetic and pharmacological disruption of vascular signaling pathways have provided unequivocal evidence that abnormal angiogenesis is a hallmark feature of cancer (Hanahan and Weinberg (2011); Chung and Ferrara, *Annu. Rev. Cell Dev. Biol.* 27, 563-584 (2011); Carmeliet and Jain, *Nature* 473, 298-307 (2011)). Cancer cells adapt to low oxygen tension by promoting the expression of genes associated with anaerobic metabolism, invasion and angiogenesis (Pugh et al., *Nat. Med.* 9, 677-684 (2003); Fraisl et al., *Dev. Cell* 16, 167-179 (2009)). The concerted action of hypoxia-regulated pathways allows tumor cells to sprout new vessels, co-opt host vessels and/or recruit angio-competent bone marrow-derived cells to generate functionally abnormal tumor vasculatures (Ferrara et al., *Nature* 438, 967-974 (2005)). Vascular endothelial growth factors (VEGFs) play central roles in this process through activation of VEGF receptor tyrosine kinases (RTKs), including VEGFR1 (Flt-1), VEGFR2 (KDR/Flk-1) and VEGFR3 (Flt-4), on endothelial cells (ECs) (Chung and Ferrara, *Annu. Rev. Cell Dev. Biol.* 27, 563-584 (2011)).

Blockade of VEGF-A signaling with BEVACIZUMAB, a humanized anti-VEGF monoclonal antibody (mAb) or with RTK inhibitors, such as SUNITINIB or SORAFENIB, has improved progression-free survival for patients with several types of cancers, including metastatic colorectal cancer, advanced non-small cell lung cancer, metastatic breast cancer, renal cell carcinoma and advanced hepatocarcinoma (Kerbel (2008); Ellis and Hicklin, *Nat. Rev. Cancer,* 8:8, 579-91 (2008)). However, although approved therapies targeting VEGF-A have offered considerable clinical benefit, many patients whose tumors initially responded eventually become non-responsive, suggesting the contribution of compensatory pathways that preserve angiogenesis in VEGF-targeted therapies (Bergers and Hanahan, *Nat. Rev. Cancer* 8:8, 592-603 (2008)). For tumors having evasive resistance or intrinsic refractoriness ("tumors refractory to anti-VEGF" or "anti-VEGF refractory tumors" herein), the approved therapies targeting VEGF-A fail to produce enduring clinical benefits.

There remains a need in the art for treating or inhibiting tumors that are refractory to conventional anti-VEGF treatments.

SUMMARY

Provided are methods for modulating angiogenesis in a cancer (or tumor) refractory to anti-VEGF treatment. In embodiments, methods for modulating angiogenesis in a refractory cancer (or tumor) may include identifying a cancer cell as being refractory to anti-VEGF, and then contacting (in vivo or in vitro) the refractory cancer cell with an effective amount of an agent that modulates interaction between Gal1 or a Gal1 fragment and a natural binding partner of Gal1 or the Gal1 fragment to thereby modulate angiogenesis. The modulating of angiogenesis preferably results in inhibition of angiogenesis in the refractory cancer cell.

The agent that modulates interaction between Gal1 or the Gal1 fragment and the natural binding partner of Gal1 or the Gal1 fragment inhibits may be, e.g., an antibody, a nucleic acid, a peptide, a fusion protein, a small molecule, or a glycan-related compound. In some embodiments, the agent that modulates interaction between Gal1 or the Gal1 fragment and the natural binding partner of Gal1 or the Gal1 fragment may be selected from the group consisting of: a blocking antibody or an antigen-binding fragment thereof that recognizes Gal1 or the Gal1 fragment; and a blocking antibody or an antigen-binding fragment thereof that recognizes the Gal1 or the Gal1 fragment natural binding partner. In certain embodiments, the agent that modulates interaction between Gal1 or the Gal1 fragment and the natural binding partner of Gal1 or the Gal1 fragment may be an anti-Gal1 monoclonal antibody or an antigen-binding fragment thereof. In still further embodiments, a monoclonal antibody that is selective for Gal1 over other galectins, or a fragment thereof, may be selected as as the agent that modulates interaction between Gal1 or the Gal1 fragment and the natural binding partner of Gal1 or the Gal1 fragment.

Cancers (or tumors) in which angiogenesis may be modulated according to methods described herein may be refractory to anti-VEGF, such as LLC1 Lewis lung carcinoma, R1.1 T cell lymphoma, and pancreatic cancer.

Methods of modulating angiogenesis in a cancer (or tumor) refractory to anti-VEGF treatment may include, in addition to identifying a cancer cell as being refractory to anti-VEGF and then contacting the refractory cancer cell with an effective amount of an agent that modulates interaction between Gal1 or a Gal1 fragment and a natural binding partner of Gal1 or the Gal1 fragment, contacting the refractory cancer cell with one or more second agent that may include a blocking antibody or an antigen binding fragment thereof that recognizes Gal1, and/or a blocking antibody or an antigen binding fragment thereof that recognizes a Gal1 binding partner or a fragment thereof. In certain embodiments, the second agent may be that is an anti-angiogenic agent, such as, e.g., an anti-VEGF antibody.

Provided herein are methods for treating a subject having a cancer (or tumor) refractory to anti-VEGF treatment, such methods including administering to the subject having the refractory cancer (or tumor) a therapeutically effective amount of an agent that inhibits interaction between Gal1 or a Gal1 fragment and the natural binding partner of Gal1 or the Gal1 fragment (i.e., a "modulating agent" as defined herein). The modulating agent administered to the subject is preferably therapeutically effective in: (a) slowing or inhibiting growth of the refractory cancer (or tumor); (b) preventing spreading of the refractory cancer (or tumor); (c) preventing recurrence of a previously spread tumor associated with the refractory cancer; (d) preventing spreading of one or more metastases associated with the refractory cancer (or tumor); (e) reducing the size of a tumor associated with the refractory cancer; and/or (f) preventing recurrence of the refractory cancer (or tumor) that has been previously treated.

Methods for treating a subject having a cancer (or tumor) refractory to anti-VEGF treatment may include administering at least a second agent, wherein the second agent may include a blocking antibody or an antigen binding fragment thereof that recognizes Gal1, and/or a blocking antibody or an antigen binding fragment thereof that recognizes a Gal1 binding partner or a fragment thereof. The additional agent(s) may include one or more anti-VEGF antibody.

In certain embodiments of the treatment methods described herein, the agent that inhibits interaction between Gal1 or the Gal1 fragment and the natural binding partner of Gal1 or the Gal1 fragment may be administered to a subject in a pharmaceutical composition that also comprises a pharmaceutically acceptable carrier selected from the group consisting of solvents, dispersion media, coatings, antibacterial agents, antifungal agents, isotonic agents and absorption delaying agents. The pharmaceutical composition may comprise: (a) as the active ingredient—an agent that inhibits interaction between Gal1 or the Gal1 fragment and the natural binding partner of Gal1 or the Gal1 fragment; and (b) as the carrier—a pharmaceutical excipient selected from the group consisting of starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol.

Modes of administration of the active ingredient (modulating agent) according to methods provided herein include, but are not limited to, parenteral administration, intradermal administration, subcutaneous administration, oral administration, inhalation, transdermal administration, transmucosal administration, and rectal administration. In certain embodiments, the agent that inhibits interaction between Gal1 or a fragment thereof and a natural binding partner of Gal1 or the Gal1 fragment may be administered to a subject having a cancer (or tumor) refractory to anti-VEGF treatment in the form of, e.g., an injectable solution, an aerosol, a nasal spray, a suppository, a cream, a gel, a tablet, and a capsule. The agent may be a nucleic acid that has been inserted into a vector, and the vector administered to the subject in need thereof in a composition by intravenous injection, local injection, or sterotactic injection.

Prophylactic methods for preventing angiogenesis in cancers (or tumors) refractory to anti-VEGF treatment may comprise administering to a subject susceptible or at risk for having a cancer refractory to anti-VEGF treatment an effective amount of an agent that binds to the Gal1 gene or a fragment thereof to attenuate hypoxia-associated angiogenesis. In embodiments, the agent that binds to the Gal1 gene or a fragment thereof may be an anti-Gal1 antibody, and may be administered to the subject susceptible or at risk for having a cancer refractory to anti-VEGF treatment in a vaccine composition.

In some embodiments, methods for treating a subject having a cancer (or tumor) refractory to anti-VEGF treatment comprise administering to the subject a therapeutically effective amount of an agent that inhibits the interaction between Gal1 or a fragment thereof and its natural binding partner(s).

In some embodiments, methods for treating a subject having a cancer (or tumor) refractory to anti-VEGF treatment comprise administering to the subject a therapeutically effective amount of a pharmaceutical composition comprising an anti-Gal1 antibody and an anti-VEGF antibody.

BRIEF DESCRIPTION OF THE DRAWINGS

FIG. 1A shows a schematic representation of N- and O-glycan biosynthesis, including relevant glycosyltransferases, such as α2-6 sialyltransferase 1 (ST6GAL1), N-acetylglucosaminyltransferase 5 (MGAT5), α2-3 sialyltransferase 1 (ST3GAL1) and core 2 N-acetylglucosaminyltransferase 1 (C2GNT1). Coordinated actions of these glycosyltransferases lead to the generation or masking of common glycosylated ligands for galectins (N-acetyl lactosamine; LacNAc) or poly-LacNAc residues in complex N-glycans or core 2 O-glycans). FIG. 1A also shows a schematic representation of lectin-binding sites in N- and O-glycans. Specific residues recognized by MAL II, LEL, SNA and L-PHA on complex N-glycans and by HPA, PNA and LEL on O-glycans are indicated (green grayscales). The common glycosylated ligand for Gal1 (LacNAc) is also indicated (purple grayscales). FIG. 1B shows the glycan repertoire of HUVEC under resting conditions (2% FCS) detected with biotinylated L-PHA, LEL, SNA, MAL II, PNA and HPA (filled histograms) or with PE-conjugated stravidin alone (open histograms). Data are representative of eight experiments. FIG. 1C shows the glycan repertoire of HUVEC under resting, proliferative (bFGF), activated (VEGF-A), tolerogenic (IL-10 and/or TGF-$\beta_1$) or pro-inflammatory (IFN-γ and/or IL-17) conditions. rMFI (relative mean fluorescence intensity)=(MFI with lectin−MFI without lectin)/ MFI without lectin. Data are presented as the ratio relative to resting conditions (dotted line; value=1) and are the mean±SEM of four experiments. *$P<0.05$, $P<0.01$ versus resting. FIG. 1D shows binding results of 488-Gal1 to HUVEC with or without lactose or sucrose, swainsonine or benzyl-α-GalNAc. $P<0.01$. Data are the mean±SEM of four experiments. FIG. 1E shows binding results of 488-Gal1 to HUVEC transfected with MGAT5 or C2GNT1 siRNA. Cells without siRNA or transfected with scrambled (src) siRNA were used as controls. **$P<0.01$. Data are the mean±SEM of four experiments. FIG. 1F shows binding results of 488-Gal1 to HUVEC exposed to tolerogenic, proliferative or inflammatory stimuli. Data are presented as the rMFI ratio relative to resting ECs (dotted line; value=1) and are the mean±SEM of four experiments. *$P<0.05$, **$P<0.01$ versus resting. FIG. 1G shows the glycan repertoire on HUVEC incubated in hypoxia (black-filled greyscales histograms) or normoxia (grey-filled greyscales histograms), detected with biotinylated L-PHA, LEL, SNA, MAL II or PNA, or with PE-conjugated stravidin alone (open histograms). Data are representative of five experiments. FIG. 1H shows the results of glycan nanoprofiling of ECs exposed to normoxia or hypoxia. Bars represent the relative abundance of neutral, mono-, di-, tri-, and tetra-sialylated N-glycans from total N-glycans. *$P<0.05$. Data are the mean±SEM of three experiments. FIG. 1I shows the binding of 488-Gal1 to HUVEC exposed to hypoxia or normoxia. $P<0.01$. Data are the mean±SEM of five experiments. FIG. 1J shows tube formation of HUVEC transfected or not with MGAT5, C2GNT1 or scr siRNA and incubated with Gal1 (1 μM), Gal1$^{N46D}$ (3 μM) and/or VEGF-A (20 ng/ml) in the absence or presence of lactose or swainsonine. $P<0.01$ versus control, †$P<0.05$ versus Gal1. Data are the mean±SEM of five experiments.

FIGS. 2A-2J show the galectin-1 co-opts VEGFR2 signaling pathways through the formation of lectin-glycan lattices on highly branched complex N-glycans. FIG. 2A shows results of a phospho-RTK signaling array of HUVEC exposed to medium (control), VEGF or Gal1, wherein in the left panel, arrows indicate proteins with increased phosphorylation intensity. Data are representative of three independent experiments. By contrast, the right panel shows quantification of pixel intensity. $*P<0.05$, $P<0.01$ versus control. Data are the mean±SEM of three independent experiments. FIG. 2B shows immunoblot analysis of VEGFR2, Akt and Erk1/2 phosphorylation induced by Gal1 or VEGF in HUVEC transfected with VEGFR2 or MGAT5 siRNA. Data are representative of three independent experiments. FIG. 2C shows tube formation results of HUVEC transfected or not with VEGFR2, NRP-1, VEGF or scr siRNA treated or not with Gal1. $P<0.01$. Data are the mean±SEM of four experiments. FIG. 2D shows tube formation results of HUVEC pre-treated with blocking antibodies to VEGFR1, VEGFR2, VEGFR3, integrins $\alpha_v\beta_3$ or $\alpha_5\beta_1$ or VEGF. $***P<0.001$. Data are the mean±SEM of four experiments. FIG. 2E shows co-immunoprecipitation results followed by immunoblot analysis of HUVEC lysates, wherein the left panel shows results from cells treated with or without Gal1 and the right panel shows results from cells transfected or not with MGAT5 or C2GNT1 siRNA or exposed to PNGase F and treated with Gal1. Input, whole cell lysate; IB, immunoblot; IP, immunoprecipitation. Data are representative of three independent experiments. FIG. 2F shows results of binding of Gal1 to rhVEGFR2 followed by FRET analysis. Left, fluorescence intensity at 518 nm measured at increasing concentrations of 594-Gal1. Right, fluorescence intensity at 518 nm of 0.5 μM 488-VEGFR2 in the presence of 594-Gal1 titrated with increasing concentrations of lactose. Data are representative of three experiments. FIG. 2G shows results of lectin blot analysis, showing selective sialylation of different VEGFRs, demonstrating the fine regulation of this process. FIG. 2H shows results of Gal1 binding to VEGFR2/KDR mutants devoid of N-glycosylation sites in each of the 7 Ig-like domains. Binding of Gal1 to immunoprecipitated KDR-HA mutants expressed as percentage relative to WT-KDR. $*P<0.05$, $P<0.01$ versus WT-KDR. Data are the mean±SEM of four independent experiments. FIG. 2I shows laser confocal microscopy results of VEGFR2 segregation in HUVEC transfected or not with MGAT5 or C2GNT1 siRNA and treated or not with Gal1 or Gal1 plus lactose. $P<0.01$, $***P<0.001$. Data are the mean±SEM (left) or are representative (right) of four independent experiments.

FIG. 3A shows tumor growth in syngeneic mice inoculated with B16-F0, CT26, LLC1 or R1.1 tumors treated with anti-VEGF mAb (5 mg/kg) or isotype control. $*P<0.05$. Data are the mean±SEM of four independent experiments with six animals per group. FIG. 3B shows the percentage of tumor-associated ECs for the same mice. $*P<0.05$, $**P<0.01$. Data are the mean±SEM of four independent experiments with six animals per group. FIG. 3C shows the glycophenotype of ECs exposed to serum-free conditioned media collected from LLC1, R1.1, B16-F0 or CT26 tumor cells previously cultured in normoxia or hypoxia. $*P<0.05$, $P<0.01$, $*P<0.001$. Data are the mean±SEM of four experiments. FIG. 3D shows the glycophenotype of ECs associated to LLC1 tumors in response to anti-VEGF treatment. $*P<0.05$, $**P<0.01$. Data are the mean±SEM of four independent experiments. FIG. 3E shows the glycophenotype of ECs associated to B16-F0 tumors in response to anti-VEGF treatment. $*P<0.05$, $**P<0.01$. Data are the mean±SEM of four independent experiments. FIG. 3F shows ELISA results of Gal1 secretion by LLC1, R1.1 or B16-F0 tumors in response to anti-VEGF treatment. $*P<0.05$, $**P<0.01$. Data are the mean±SEM of four experiments.

FIGS. 4A-4E show that tumors devoid of Gal1 circumvent refractoriness to anti-VEGF therapy. FIG. 4A shows tumor growth in syngeneic B6 mice inoculated with LLC1 or R1.1 tumors transduced with Gal1-specific shRNA (sh-Gal1.1) or sh-scr and treated with anti-VEGF mAb. $*P<0.05$, $P<0.01$. Data are the mean±SEM of four independent experiments with six animals per group. FIG. 4B shows the percentage of tumor-associated ECs in the same mice. $P<0.01$. Data are the mean±SEM of four independent experiments with six animals per group. FIG. 4C shows tumor growth in Lgals1$^{-/-}$ B6 mice inoculated with LLC1 tumors transduced with shGal1.1 or sh-scr and treated with anti-VEGF mAb. $P<0.01$ versus sh-scr. Data are the mean±SEM of three independent experiments with six animals per group. FIG. 4D shows tumor growth in syngeneic B6 mice inoculated with B16-F0 tumors transduced with shGal1.1 or sh-scr and treated with anti-VEGF mAb. $P<0.01$. Data are the mean±SEM of four independent experiments with six animals per group. FIG. 4E shows the percentage of tumor-associated in the same mice. $**P<0.01$. Data are the mean±SEM of four independent experiments with six animals per group.

FIGS. 5A-5G show that reprogramming of EC glycosylation converts anti-VEGF refractory tumors to sensitive tumors. FIG. 5A shows flow cytometry results of L-PHA staining in ECs associated to LLC1 tumors inoculated into WT or Mgat5$^{-/-}$ mice (day 16). Data are representative of four independent experiments with six animals per group. FIG. 5B shows tumor growth in Mgat5$^{-/-}$ or WT mice inoculated with LLC1 tumors and treated with anti-VEGF mAb (5 mg/kg) or isotype control. $P<0.01$ versus WT. Data are the mean±SEM of four independent experiments with six animals per group. FIG. 5C shows the percentage of tumor-associated ECs in Mgat5$^{-/-}$ or WT mice inoculated with LLC1 tumors and treated with anti-VEGF mAb (5 mg/kg) or isotype control. $*P<0.001$ versus WT. Data are the mean±SEM of four independent experiments with six animals per group. FIG. 5D shows flow cytometry results of SNA staining in ECs associated with B16-F0 tumors inoculated into WT or St6gal1$^{-/-}$ mice (day 16). Data are representative of four independent experiments with six animals per group. FIG. 5E shows tumor growth in St6gal1$^{-/-}$ or WT mice inoculated with B16-F0 tumors and treated with anti-VEGF mAb (5 mg/kg) or isotype control. $P<0.01$ versus WT. Data are the mean±SEM of four independent experiments with six animals per group. FIG. 5F shows the percentage of tumor-associated ECs in the same mice. $*P<0.001$ versus WT. Data are the mean±SEM of four independent experiments with six animals per group. FIG. 5G shows tumor growth in St6gal1$^{-/-}$ mice inoculated with B16-F0 tumors and treated with anti-VEGF mAb (5 mg/kg) or anti-VEGF mAb plus axitinib (30 mg/kg) or inoculated with B16-F0 tumors transduced with Gal1-specific shRNA (shGal1.1) and treated with anti-VEGF mAb. $**P<0.01$. Data are the mean±SEM of three independent experiments with six animals per group.

FIGS. 6A-6L show that targeting the Gal1-N-glycan axis promotes vascular remodeling and overcomes refractoriness to anti-VEGF therapy. FIG. 6A shows tube formation results of HUVEC induced by Gal1 or VEGF-A in the absence or presence of the anti-Gal1 (F8.G7) mAb or isotype control. P<0.01. Data are the mean±SEM of four experiments. FIG. 6B shows an immunoblot of VEGFR2 phosphorylation in HUVEC treated with Gal1 in the absence or presence of F8.G7 mAb or isotype control or in HUVEC transfected with MGAT5 siRNA. Results are representative of three independent experiments. FIG. 6C shows growth of LLC1 and microvessel density of tumors inoculated in syngeneic mice treated with anti-VEGF mAb or F8.G7 mAb (alone or in combination) or with isotype control. P<0.01. Data are the mean±SEM of four independent experiments with six animals per group. FIG. 6D shows growth of R1.1. *P<0.05, **P<0.01. Data are the mean±SEM of four independent experiments with six animals per group. FIG. 6E shows growth of B16-F0 and microvessel density of tumors inoculated in syngeneic mice treated with anti-VEGF mAb or F8.G7 mAb (alone or in combination) or with isotype control. *P<0.05, P<0.01, *P<0.001. Data are the mean±SEM of four independent experiments with six animals per group. FIG. 6F shows ELISA results of Gal1 secretion by B16-F0, LLC1 and R1.1 tumors (at day 16) inoculated in syngeneic mice and treated with anti-Gal1 F8.G7 mAb or isotype control. ***P<0.001. Data are the mean±SEM of four independent experiments with five animals per group. FIG. 6G shows confocal microscopy results of lectin (GLS-1$_{B4}$)-perfused vessels in size-matched B16-F0 tumors inoculated in syngeneic mice and treated for 4-5 days with F8.G7 mAb or isotype control. The right panel quantifies vessel diameters. *P<0.05. Data are the mean±SEM of four independent experiments with six mice per group. FIG. 6H shows confocal microscopy results of lectin-perfused vessels (green grayscales) labeled with anti-α-SMA Ab (red grayscales) in sized-matched B16-F0 tumors inoculated in syngeneic mice and treated for 4-5 days with F8.G7 mAb or with isotype control. The right panel shows the percentage of tumor vessels showing pericyte coverage. **P<0.01. Data are the mean±SEM of four independent experiments with six mice per group. FIG. 6I shows confocal microscopy results of RGS5, desmin, α-SMA and PDGFR-β in pericytes associated to vessels of B16-F0 tumors inoculated into syngeneic mice and treated for 4-5 days with F8.G7 mAb or isotype control. Quantification (left) and representative images (right) are shown. *P<0.05, P<0.01. Data are the mean±SEM of four independent experiments with six mice per group. FIG. 6J shows confocal microscopy of B16-F0 size-matched tumors stained with Hypoxiprobe-1. Data are the mean±SEM of four independent experiments with six mice per group. FIGS. 6K and 6L show confocal microscopy results of CD31 (FIG. 6K) and lectin-perfused vessels (green greyscales) labeled with anti-α-SMA Ab (red greyscales) (FIG. 6L) in LLC1 tumors inoculated into WT mice and treated with anti-Gal1 F8.G7 mAb or with isotype control or LLC1 tumors inoculated into Mgat5$^{-/-}$ mice. The right panel of FIG. 6K quantifies vessel diameter, and the right panel of FIG. 6L quantifies pericyte coverage. P<0.01. Data are the mean±SEM of four independent experiments with six mice per group.

FIGS. 7A-7R show disruption of Gal1-N-glycan interactions controlling both vascular and immune compartments. FIGS. 7A-7D show proliferation results (FIG. 7A) and ELISA results of IFN-γ (FIG. 7B), IL-17 (FIG. 7C) and IL-10 (FIG. 7D) by TDLN cells from mice inoculated with B16-F0 tumor cells and treated with F8.G7 mAb or isotype control and restimulated ex vivo with B16 cells. **P<0.01. Data are the mean±SEM of four independent experiments with six mice per group. FIGS. 7E-7G show ELISA results of IFN-γ (FIG. 7E), IL-17 (FIG. 7F) and IL-10 (FIG. 7G) secretion of IFN-γ-producing CD8+ T cells in TDLNs from mice inoculated with LLC1 cells and treated with F8.G7 mAb or isotype control. *P<0.05, *P<0.001. Data are the mean±SEM of four independent experiments with six mice per group. FIG. 7H shows flow cytometry results of IFN-γ-producing CD8$^+$ T cells in TDLNs from mice inoculated with B16-F0 cells and treated with F8.G7 mAb or isotype control. P<0.01. Data are the mean±SEM of four independent experiments with six mice per group. FIG. 7I shows flow cytometry results of IFN-γ-producing CD8$^+$ T cells in TDLNs from mice inoculated with LLC1 cells and treated with F8.G7 mAb or isotype control. P<0.01. Data are the mean±SEM of four independent experiments with six mice per group. FIG. 7J shows confocal microscopy results of tumor-infiltrating CD8$^+$ T cells in mice inoculated with B16-F0 tumor cells and treated with F8.G7 mAb or isotype control. P<0.01. Data in the left panel are representative of four independent experiments with six mice per group; data in the right panel are the mean±SEM of four independent experiments with six mice per group. FIGS. 7K-7O show ELISA results of IFN-γ (FIG. 7K), IL-17 (FIG. 7L) and IL-10 (FIG. 7M) and flow cytometry results of IFN-γ-producing CD4+(FIG. 7N) or CD8+(FIG. 7O) T cells in TDLNs from Mgat5$^{-/-}$ mice inoculated with LLC1 tumors. *P<0.05, P<0.01, *P<0.001. Data are the mean±SEM (FIGS. 7L-7N) or are representative (FIG. 7O) of four independent experiments with six mice per group. FIGS. 7P and 7Q show confocal microscopy results of tumor-infiltrating CD8+ T cells (FIG. 7P) and F4/80+ macrophages (FIG. 7Q) in Mgat5$^{-/-}$ or WT mice inoculated with LLC1 tumors. *P<0.05. Data in the left panel of FIG. 7P are representative of four independent experiments with six mice per group. Data in the right panel of FIG. 7P and in FIG. 7Q are the mean±SEM of four independent experiments with six mice per group. FIG. 7R shows flow cytometry analysis of T cell influx to tumor parenchyma or spleen. Spleen T cells were purified from tumor (B16-F0)-bearing mice, stained with CFSE and transferred (5×10$^6$) to mice with established tumors treated with F8.G7 mAb or isotype control. Data are representative of four independent experiments with six mice per group.

FIG. 8B shows ELISA results of bFGF (left), TGF-β$_1$ (middle) and VEGF-A (right) secretion by LLC1, R1.1, B16-F0 and CT26 tumor cells exposed to normoxia or hypoxia. *P<0.05, P<0.01, *P<0.001. Data are the mean±SEM of two independent experiments. FIG. 8C shows ELISA results of Gal3 or Gal8 secretion by refractory (LLC1, R1.1) or sensitive (B16-F0) tumors in response to anti-VEGF treatment. Data are the mean±SEM of three independent experiments.

FIG. 9A shows an immunoblot of Gal1 in total lysates of LLC1, R1.1 and B16-F0 non-transduced tumor cells (WT) or transduced with two different Gal1-specific shRNA (shGal1.1, shGal1.2) or with scrambled shRNA (sh-scr). Data are representative of three independent experiments. FIG. 9B shows the results of an MTS proliferation assay of LLC1, R1.1 and B16-F0 non-transduced tumor cells (WT) or tumor cells transduced with sh-Gal1.1 or control sh-scr. Data are the mean±SEM of four experiments. FIG. 9C shows that tumor growth results in syngeneic B6 mice inoculated with B16-F0 tumors transduced with shGal1.1 (bulk) or a clone obtained by limiting dilution (shGal1.1-c) or control sh-scr. *P<0.05 versus sh-scr. Data are the mean±SEM of four independent experiments with six mice per group. FIG. 9D shows the results of immunoblot analysis of Gal3, Gal4, Gal7 and Gal8 in lysates of B16-F0 cells transduced with shGal1.1 or sh-scr. Data are representative of two independent experiments.

FIG. 10A shows migration of HUVEC induced by Gal1 or VEGF-A in the absence or presence of the anti-Gal1 (F8.G7) mAb or isotype control. **$P<0.01$. Data are representative (left) or are the mean±SEM of four independent experiments. FIG. 10B shows the dose-dependent effect of anti-Gal1 (F8.G7) mAb. Tumor growth in syngeneic mice inoculated with B16-F0 tumors and treated with different doses of anti-Gal1 F8.G7 mAb or with isotype control when tumors reached 100 mm$^3$. *$P<0.05$, **$P<0.01$. Data are the mean±SEM of four independent experiments with six mice per group.

FIG. 11A shows tumor growth results in B6.Rag1$^{-/-}$ mice inoculated with B16-F0 tumors and treated with F8.G7 mAb or with isotype control when tumors reached 100 mm$^3$. *$P<0.05$. Data are the mean±SEM of two independent experiments with six animals per group. FIG. 11B shows the number of fluorescently—labeled beads (relative to $1\times10^6$ events) reaching tumor and spleen of mice inoculated with B16-F0 tumors and treated with F8.G7 mAb or with isotype control. $P<0.01$. Data are the mean±SEM of two independent experiments with four animals per group. FIG. 11C shows the number of fluorescently-labeled beads (relative to $1\times10^6$ events) reaching the tumor of Mgat5$^{-/-}$ or WT mice inoculated with LLC1 cells. $P<0.01$. Data are the mean±SEM of two independent experiments with four mice per group.

FIG. 16C depicts a tubulogensis assay of HUVEC in the presence of Gal1 alone or in combination with anti-Gal1 clone 21. FIG. 16D depicts (left) quantification of migration assays, and (right) representative images of HUVEC migration induced by human plasma from patients treated with anti-VEGF antibody Bevacizumab in the absence or presence of anti-Gal1 clone 21.

DEFINITIONS

Figure 1A:
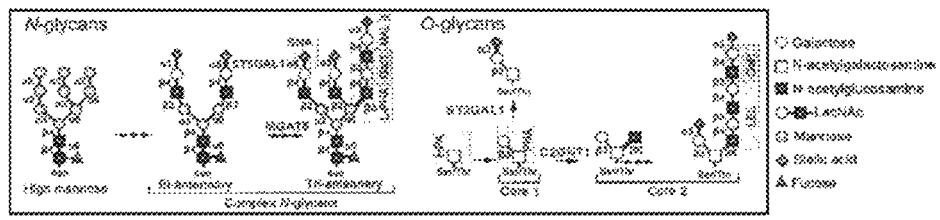
FIGS. 1A-1J show differential glycosylation of endothelial cells (ECs) controlling the formation of lectin-glycan lattices.

When introducing elements of various embodiments, the articles "a," "an," "the" and "said" are intended to mean that there are one or more of the elements. The terms "comprising," "including" and "having" are intended to be inclusive and mean that there may be additional elements other than the listed elements. Additional terms are defined below.

The term "Gal1" as used herein refers to known Galectin-1 sequences, domains, fragments, and variants thereof, as well as gene products of the Gal1 gene and/or modulators thereof. The term "Gal1" also refers to a glycan-binding protein belonging to a highly-conserved family of animal lectins. Sequences, structures, domains, biophysical characteristics, and functions of Gal1 genes and gene products have been described in the art. See, e.g., Rabinovich et al., *Trends Immunol.* 23:313-320 (2002); Liu and Rabinovich, *Nature Reviews Cancer* 5:29-41 (2005); Rubinstein et al., *Cancer Cell* 5:241-251 (2004); Le et al., *J. Clin. Oncol.* 23:8932-8941 (2005); Vasta et al., *Curr. Opin. Struct. Biol.* 14:617-630 (2004); Toscano et al., *Cyt. Growth Fact. Rev.* 18:57-71 (2007); Camby et al., *Glycobiology* 16:137R-157R (2006) (the disclosures of the cited reference being incorporated by reference herein in their entireties). The Gal1 gene is also expressed in other cells known in the art. See, e.g., Gottschalk et al., *Annu. Rev. Med.* 56, 29-44 (2005); Nalesnik et al., *Clin. Transplant.* 13, 39-44 (1999); Toscano et al., *Nat. Immunol.* 8, 825-834 (2007); Ilarregui et al., *Nat. Immunol.* 10, 981-991 (2009); Re et al., *J. Clin. Oncol.* 23, 6379-6386 (2005); Marshall et al., *Blood* 103, 1755-1762 (2004); Gandhi et al., *Blood* 108, 2280-2289 (2006); Juszczynski et al., *Proc. Natl. Acad. Sci. U.S.A.* 104, 13134-13139 (2007); Rodig et al., *Clin. Cancer Res.* 14, 3338-3344 (2008); Rabinovich et al., *Trends Immunol.* 23:313-320 (2002); Liu and Rabinovich, *Nature Reviews Cancer* 5:29-41 (2005); Rubinstein et al., *Cancer Cell* 5:241-251 (2004); Le et al., *J. Clin. Oncol.* 23:8932-8941 (2005); Vasta et al., *Curr. Opin. Struct. Biol.* 14:617-630 (2004); Toscano et al., *Cyt. Growth Fact. Rev.* 18:57-71 (2007); Camby et al., *Glycobiology* 16:137 R-157R (2006). Human Gal1 sequences include those listed below.

```
Gal1 Coding Nucleic Acid Sequence
                            (SEQ ID NO: 1)
ATGGCTTGTGGTCTGGTCGCCAGCAACCTGAATCTCAAACCTGGAG

AGTGCCTTCGAGTGCGAGGCGAGGTGGCTCCTGACGCTAAGAGCTT

CGTGCTGAACCTGGGCAAAGACAGCAACAACCTGTGCCTGCACTTC

AACCCTCGCTTCAACGCCCACGGCGACGCCAACACCATCGTGTGCA

ACAGCAAGGACGGCGGGGCCTGGGGGACCGAGCAGCGGGAGGCTGT

CTTTCCCTTCCAGCCTGGAAGTGTTGCAGAGGTGTGCATCACCTTC
```

-continued

```
GACCAGGCCAACCTGACCGTCAAGCTGCCAGATGGATACGAATTCA

AGTTCCCCAACCGCCTCAACCTGGAGGCCATCAACTACATGGCAGC

TGACGGTGACTTCAAGATCAAATGTGTGGCCTTTGACTGA

Gal1 Protein Sequence
                                        (SEQ ID NO: 2)
MACGLVASNLNLKPGECLRVRGEVAPDAKSFVLNLGKDSNNLCLHF

NPRFNAHGDANTIVCNSKDGGAWGTEQREAVFPFQPGSVAEVCITF

DQANLTVKLPDGYEFKFPNRLNLEAINYMAADGDFKIKCVAFD
```

A "Gal1 antagonist" refers to a molecule (peptidyl or non-peptidyl) capable of neutralizing, blocking, inhibiting, abrogating, reducing or interfering with activities of a Gal1 sequence, including its binding to one or more Gal1 receptors. Gal1 antagonists include anti-Gal1 antibodies and antigen-binding fragments thereof, receptor molecules and derivatives that bind specifically to Gal1, thereby sequestering its binding to one or more receptors (e.g., soluble Gal1 receptor proteins or Gal1 binding fragments thereof, or chimeric Gal1 receptor proteins), anti-Gal1 receptor antibodies and Gal1 receptor antagonists, such as small molecule inhibitors of the Gal1 tyrosine kinases, and fusion proteins. Gal1 antagonists according to embodiments may include antagonists of Gal1, antisense molecules directed to Gal1, RNA aptamers, and ribozymes against Gal1 or Gal1 receptors. Gal1 antagonists useful in embodiments may further include peptidyl or non-peptidyl compounds that specifically bind Gal1, such as anti-Gal1 antibodies and antigen-binding fragments thereof, polypeptides, antibody variants or fragments thereof that specifically bind to Gal1, antisense nucleic oligomers complementary to at least a fragment of a nucleic acid molecule encoding a Gal1 polypeptide, small RNAs complementary to at least a fragment of a nucleic acid molecule encoding a VEGF polypeptide, ribozymes that target Gal1, peptibodies to Gal1, and Gal1 aptamers. In embodiments, the Gal1 antagonist reduces or inhibits, by at least 10%, or more, the expression level or biological activity of Gal1.

The term "anti-Gal1 antibody" refers to an antibody that is capable of binding to Gal1 with sufficient affinity. In embodiments, the anti-Gal1 antibody may be used as a therapeutic agent in targeting and interfering with diseases or conditions in which Gal1 activity is involved. The antibody selected will normally have a sufficiently strong binding affinity for Gal1. Antibody affinities may be determined by a surface plasmon resonance based assay (such as the BIACORE assay described in PCT Application Publication No. WO 2005/012359), enzyme-linked immunoabsorbent assay (ELISA), and/or competition assays (e.g., RIAs).

The terms "VEGF" and "VEGF-A" are used interchangeably to refer to the native sequence 165 amino acid vascular endothelial cell growth factor and related 121-, 145-, 183-, 189-, and 206-amino acid vascular endothelial cell growth factors together with the naturally occurring allelic and processed forms thereof, as well as variants thereof. See, e.g., Leung et al., Science, 246:1306 (1989); Houck et al., Mol. Endocrin., 5:1806 (1991); and Robinson & Stringer, Journal of Cell Science, 144(5):853-865 (2001)). VEGF-A is part of a gene family that includes VEGF-B, VEGF-C, VEGF-D, VEGF-E, VEGF-F, and PlGF. VEGFs primarily bind to VEGF receptor tyrosine kinases (RTKs), including VEGFR1 (Flt-1), VEGFR2 (Flk-1/KDR) and VEGFR3 (Flt-4) on endothelial cells (ECs) (see Chung and Ferrara, Annu. Rev. Cell Dev. Biol. 27, 563-584 (2011)).

Sequences, structures, domains, biophysical characteristics, and functions of VEGFR2 genes and gene products, and glycosylated forms thereof, have been described in the art. See, e.g., Terman et al., Biochem. Biophys. Res. Commun. 187:1579-1586 (1992); Witte et al., Cancer Metastasis 17:155-161 (1998); Ortega et al., Front. Biosci. 4:D141-D152 (1999); Shibuya, Biol. Chem. 383:1573-1579 (2002); Olsson et al., Nat. Rev. Mol. Cell. Biol. 7:359-371 (2006); and Shibuya, J. Biochem. Mol. Biol. 39:469-478 (2006). Known VEGFR2 genes and gene products include those for, e.g., chimpanzee VEGFR2 (NCBI Accession XM_517284.2 and XP_517284.2), dog VEGFR2 (NCBI Accession XM_539273.2 and XP_539273.2), cow VEGFR2 (NCBI Accession XM_611785.3 and XP_611785.3), mouse VEGFR2 (NCBI Accession NM_010612.2 and NP_034742.2) and chicken Gal1 (NM_001004368.1 and NP_001004368.1). In addition, glycosylated forms of VEGFR2 are also known, as described by, e.g., Zhang et al., Cell Death Differ. 17:499 (2010) (incorporated by reference herein in its entirety). Accordingly, the terms "VEGF" or "VEGF-A" also refer to VEGFs from non-human species, such as, for example, mouse, rat or primate.

Human VEGFR2 sequences include those provided below.

```
VEGFR2 Coding Nucleic Acid Sequence
                                        (SEQ ID NO: 3)
ATGCAGAGCAAGGTGCTGCTGGCCGTCGCCCTGTGGCTCTGCGTGG

AGACCCGGGCCGCCTCTGTGGGTTTGCCTAGTGTTTCTCTTGATCT

GCCCAGGCTCAGCATACAAAAAGACATACTTACAATTAAGGCTAAT

ACAACTCTTCAAATTACTTGCAGGGGACAGAGGGACTTGGACTGGC

TTTGGCCCAATAATCAGAGTGGCAGTGAGCAAAGGGTGGAGGTGAC

TGAGTGCAGCGATGGCCTCTTCTGTAAGACACTCACAATTCCAAAA

GTGATCGGAAATGACACTGGAGCCTACAAGTGCTTCTACCGGGAAA

CTGACTTGGCCTCGGTCATTTATGTCTATGTTCAAGATTACAGATC

TCCATTTATTGCTTCTGTTAGTGACCAACATGGAGTCGTGTACATT

ACTGAGAACAAAAACAAAACTGTGGTGATTCCATGTCTCGGGTCCA

TTTCAAATCTCAACGTGTCACTTTGTGCAAGATACCCAGAAAAGAG

ATTTGTTCCTGATGGTAACAGAATTTCCTGGGACAGCAAGAAGGGC

TTTACTATTCCCAGCTACATGATCAGCTATGCTGGCATGGTCTTCT

GTGAAGCAAAAATTAATGATGAAAGTTACCAGTCTATTATGTACAT

AGTTGTCGTTGTAGGGTATAGGATTTATGATGTGGTTCTGAGTCCG

TCTCATGGAATTGAACTATCTGTTGGAGAAAAGCTTGTCTTAAATT

GTACAGCAAGAACTGAACTAAATGTGGGGATTGACTTCAACTGGGA

ATACCCTTCTTCGAAGCATCAGCATAAGAAACTTGTAAACCGAGAC

CTAAAAACCCAGTCTGGGAGTGAGATGAAGAAATTTTTGAGCACCT

TAACTATAGATGGTGTAACCCGGAGTGACCAAGGATTGTACACCTG

TGCAGCATCCAGTGGGCTGATGACCAAGAAGAACAGCACATTTGTC

AGGGTCCATGAAAAACCTTTTGTTGCTTTTGGAAGTGGCATGGAAT

CTCTGGTGGAAGCCACGGTGGGGAGCGTGTCAGAATCCCTGCGAA

GTACCTTGGTTACCCACCCCCAGAAATAAAATGGTATAAAAATGGA

ATACCCCTTGAGTCCAATCACACAATTAAAGCGGGGCATGTACTGA
```

-continued

```
CGATTATGGAAGTGAGTGAAAGAGACACAGGAAATTACACTGTCAT
CCTTACCAATCCCATTTCAAAGGAGAAGCAGAGCCATGTGGTCTCT
CTGGTTGTGTATGTCCCACCCCAGATTGGTGAGAAATCTCTAATCT
CTCCTGTGGATTCCTACCAGTACGGCACCACTCAAACGCTGACATG
TACGGTCTATGCCATTCCTCCCCCGCATCACATCCACTGGTATTGG
CAGTTGGAGGAAGAGTGCGCCAACGAGCCCAGCCAAGCTGTCTCAG
TGACAAACCCATACCCTTGTGAAGAATGGAGAAGTGTGGAGGACTT
CCAGGGAGGAAATAAAATTGAAGTTAATAAAAATCAATTTGCTCTA
ATTGAAGGAAAAACAAAACTGTAAGTACCCTTGTTATCCAAGCGG
CAAATGTGTCAGCTTTGTACAAATGTGAAGCGGTCAACAAAGTCGG
GAGAGGAGAGAGGGTGATCTCCTTCCACGTGACCAGGGGTCCTGAA
ATTACTTTGCAACCTGACATGCAGCCCACTGAGCAGGAGAGCGTGT
CTTTGTGGTGCACTGCAGACAGATCTACGTTTGAGAACCTCACATG
GTACAAGCTTGGCCCACAGCCTCTGCCAATCCATGTGGGAGAGTTG
CCCACACCTGTTTGCAAGAACTTGGATACTCTTTGGAAATTGAATG
CCACCATGTTCTAATAGCACAAATGACATTTTGATCATGGAGCT
TAAGAATGCATCCTTGCAGGACCAAGGAGACTATGTCTGCCTTGCT
CAAGACAGGAAGACCAAGAAAAGACATTGCGTGGTCAGGCAGCTCA
CAGTCCTAGAGCGTGTGGCACCCACGATCACAGGAAACCTGGAGAA
TCAGACGACAAGTATTGGGGAAAGCATCGAAGTCTCATGCACGGCA
TCTGGGAATCCCCCTCCACAGATCATGTGGTTTAAAGATAATGAGA
CCCTTGTAGAAGACTCAGGCATTGTATTGAAGGATGGGAACCGGAA
CCTCACTATCCGCAGAGTGAGGAAGGAGGACGAAGGCCTCTACACC
TGCCAGGCATGCAGTGTTCTTGGCTGTGCAAAAGTGGAGGCATTTT
TCATAATAGAAGGTGCCCAGGAAAAGACGAACTTGGAAATCATTAT
TCTAGTAGGCACGGCGGTGATTGCCATGTTCTTCTGGCTACTTCTT
GTCATCATCCTACGGACCGTTAAGCGGGCCAATGGAGGGGAACTGA
AGACAGGCTACTTGTCCATCGTCATGGATCCAGATGAACTCCCATT
GGATGAACATTGTGAACGACTGCCTTATGATGCCAGCAAATGGGAA
TTCCCCAGAGACCGGCTGAAGCTAGGTAAGCCTCTTGGCCGTGGTG
CCTTTGGCCAAGTGATTGAAGCAGATGCCTTTGGAATTGACAAGAC
AGCAACTTGCAGGACAGTAGCAGTCAAAATGTTGAAAGAAGGAGCA
ACACACAGTGAGCATCGAGCTCTCATGTCTGAACTCAAGATCCTCA
TTCATATTGGTCACCATCTCAATGTGGTCAACCTTCTAGGTGCCTG
TACCAAGCCAGGAGGGCCACTCATGGTGATTGTGGAATTCTGCAAA
TTTGGAAACCTGTCCACTTACCTGAGGAGCAAGAGAAATGAATTTG
TCCCCTACAAGACCAAAGGGGCACGATTCCGTCAAGGGAAAGACTA
CGTTGGAGCAATCCCTGTGGATCTGAAACGGCGCTTGGACAGCATC
ACCAGTAGCCAGAGCTCAGCCAGCTCTGGATTTGTGGAGGAGAAGT
CCCTCAGTGATGTAGAAGAAGAGGAAGCTCCTGAAGATCTGTATAA
GGACTTCCTGACCTTGGAGCATCTCATCTGTTACAGCTTCCAAGTG
GCTAAGGGCATGGAGTTCTTGGCATCGCGAAAGTGTATCCACAGGG
ACCTGGCGGCACGAAATATCCTCTTATCGGAGAAGAACGTGGTTAA
AATCTGTGACTTTGGCTTGGCCCGGGATATTTATAAAGATCCAGAT
TATGTCAGAAAAGGAGATGCTCGCCTCCCTTTGAAATGGATGGCCC
CAGAAACAATTTTTGACAGAGTGTACACAATCCAGAGTGACGTCTG
GTCTTTTGGTGTTTTGCTGTGGGAAATATTTTCCTTAGGTGCTTCT
CCATATCCTGGGGTAAAGATTGATGAAGAATTTTGTAGGCGATTGA
AAGAAGGAACTAGAATGAGGGCCCCTGATTATACTACACCAGAAAT
GTACCAGACCATGCTGGACTGCTGGCACGGGGAGCCCAGTCAGAGA
CCCACGTTTTCAGAGTTGGTGGAACATTTGGGAAATCTCTTGCAAG
CTAATGCTCAGCAGGATGGCAAAGACTACATTGTTCTTCCGATATC
AGAGACTTTGAGCATGGAAGAGGATTCTGGACTCTCTCTGCCTACC
TCACCTGTTTCCTGTATGGAGGAGGAGGAAGTATGTGACCCCAAAT
TCCATTATGACAACACAGCAGGAATCAGTCAGTATCTGCAGAACAG
TAAGCGAAAGAGCCGGCCTGTGAGTGTAAAAACATTTGAAGATATC
CCGTTAGAAGAACCAGAAGTAAAAGTAATCCCAGATGACAACCAGA
CGGACAGTGGTATGGTTCTTGCCTCAGAAGAGCTGAAAACTTTGGA
AGACAGAACCAAATTATCTCCATCTTTTGGTGGAATGGTGCCCAGC
AAAAGCAGGGAGTCTGTGGCATCTGAAGGCTCAAACCAGACAAGCG
GCTACCAGTCCGGATATCACTCCGATGACACAGACACCACCGTGTA
CTCCAGTGAGGAAGCAGAACTTTTAAAGCTGATAGAGATTGGAGTG
CAAACCGGTAGCACAGCCCAGATTCTCCAGCCTGACTCGGGGACCA
CACTGAGCTCTCCTCCTGTTTAA
```

VEGFR2 Protein Sequence (SEQ ID NO: 4)

MQSKVLLAVALWLCVETRAASVGLPSYSLDLPRLSIQKDILTIKAN
TTLQITCRGQRDLDWLWPNNQSGSEQRVEVTECSDGLFCKTLTIPK
VIGNDTGAYKCFYRETDLASVIYVYVQDYRSPFIASYSDQHGVVYI
TENKNKTVVIPCLGSISNLNVSLCARYPEKRFVPDGNRISWDSKKG
FTIPSYMISYAGMVFCEAKINDESYQSIMYIVVVVGYRIYDVVLSP
SHGIELSVGEKLVLNCTARTELNVGIDFNWEYPSSKHQHKKLVNRD
LKTQSGSEMKKFLSTLTIDGVTRSDQGLYTCAASSGLMTKKNSTFV
RVHEKPFVAFGSGMESLVEATVGERVRIPAKYLGYPPPEIKWYKNG
IPLESNHTIKAGHVLTIMEVSERDTGNYTVILTNPISKEKQSHVVS
LVVYVPPQIGEKSLISPVDSYQYGTTQTLTCTVYAIPPPHHIHWYW
QLEEECANEPSQAVSVTNPYPCEEWRSVEDFQGGNKIEVNKNQFAL
IEGKNKTVSTLVIQAANVSALYKCEAVNKVGRGERVISFHVTRGPE
ITLQPDMQPTEQESYSLWCTADRSTFENLTWYKLGPQPLPIHVGEL
PTPVCKNLDTLWKLNATMFSNSTNDILIMELKNASLQDQGDYVCLA
QDRKTKKRHCVVRQLTVLERVAPTITGNLENQTTSIGESIEVSCTA
SGNPPPQMWFKDNETLVEDSGIVLKDGNRNLTIRRVRKEDEGLYTC

```
QACSVLGCAKVEAFFIIEGAQEKTNLEIIILVGTAVIAMFFWLLLV

IILRTVKRANGGELKTGYLSIVMDPDELPLDEHCERLPYDASKWEF

PRDRLKLGKPLGRGAFGQVIEADAFGIDKTATCRTVAVKMLKEGAT

HSEHRALMSELKILIHIGHHLNVVNLLGACTKPGGPLMVIVEFCKF

GNLSTYLRSKRNEFVPYKTKGARFRQGKDYVGAIPVDLKRRLDSIT

SSQSSASSGFVEEKSLSDVEEEEAPEDLYKDFLTLEHLICYSFQVA

KGMEFLASRKCIHRDLAARNILLSEKNVVKICDFGLARDIYKDPDY

VRKGDARLPLKWMAPETIFDRVYTIQSDVWSFGVLLWEIFSLGASP

YPGVKIDEEFCRRLKEGTRMRAPDYTTPEMYQTMLDCWHGEPSQRP

TFSELVEHLGNLLQANAQQDGKDYIVLPISETLSMEEDSGLSLPTS

PVSCMEEEEVCDPKFHYDNTAGISQYLQNSKRKSRPVSVKTFEDIP

LEEPEVKVIPDDNQTDSGMVLASEELKTLEDRTKLSPSFGGMVPSK

SRESVASEGSNQTSGYQSGYHSDDTDTTVYSSEEAELLKLIEIGVQ

TGSTAQILQPDSGTTLSSPPV
```

The term "VEGF" may also be used to refer to truncated forms or fragments of the polypeptide comprising amino acids 8 to 109 or 1 to 109 of the 165-amino acid human vascular endothelial cell growth factor. The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native sequence VEGF.

A "VEGF antagonist" refers to a molecule (peptidyl or non-peptidyl) capable of neutralizing, blocking, inhibiting, abrogating, reducing or interfering with activities of a native sequence VEGF, including its binding to one or more VEGF receptors. VEGF antagonists include anti-VEGF antibodies and antigen-binding fragments thereof, receptor molecules and derivatives that bind specifically to VEGF, thereby sequestering its binding to one or more receptors (e.g., soluble VEGF receptor proteins or VEGF binding fragments thereof, or chimeric VEGF receptor proteins), anti-VEGF receptor antibodies and VEGF receptor antagonists, such as small molecule inhibitors of the VEGFR tyrosine kinases, and fusion proteins. VEGF antagonists according to embodiments may include antagonists of VEGF, antisense molecules directed to VEGF, RNA aptamers, and ribozymes against VEGF or VEGF receptors. VEGF antagonists useful in embodiments may further include peptidyl or non-peptidyl compounds that specifically bind VEGF, such as anti-VEGF antibodies and antigen-binding fragments thereof, polypeptides, antibody variants or fragments thereof that specifically bind to VEGF, antisense nucleic oligomers complementary to at least a fragment of a nucleic acid molecule encoding a VEGF polypeptide, small RNAs complementary to at least a fragment of a nucleic acid molecule encoding a VEGF polypeptide, ribozymes that target VEGF, peptibodies to VEGF, and VEGF aptamers. In embodiments, the VEGF antagonist reduces or inhibits, by at least 10%, or more, the expression level or biological activity of VEGF.

The term "anti-VEGF antibody" or "an antibody that binds to VEGF" refers to an antibody that is capable of binding to VEGF with sufficient affinity and, specifically, that the antibody is useful as a diagnostic and/or therapeutic agent in targeting VEGF. In embodiments, the anti-VEGF antibody may be used as a therapeutic agent in targeting and interfering with diseases or conditions in which the VEGF activity is involved. The antibody selected will normally have a sufficiently strong binding affinity for VEGF, for example, the antibody may bind to human VEGF with a Kd value of between 100 nM-1 pM. Antibody affinities may be determined by a surface plasmon resonance based assay (such as the BIACORE assay described in PCT Application Publication No. WO 2005/012359), enzyme-linked immunoabsorbent assay (ELISA), and/or competition assays (e.g., RIAs).

In embodiments, an anti-VEGF antibody may be substituted with a VEGF specific antagonist, e.g., a VEGF receptor molecule or chimeric VEGF receptor molecule as described herein. In certain embodiments, the anti-VEGF antibody is BEVACIZUMAB. The anti-VEGF antibody, or antigen-binding fragment thereof, can be a monoclonal antibody, a chimeric antibody, a fully human antibody, or a humanized antibody.

The term "angiogenesis" or "neovascularization" refers to the process by which new blood vessels develop from pre-existing vessels. (Varner et al., Angiogen. 3(1):53-60 (1999); Mousa et al., Angiogenesis Stim. and Inhib., 35-42, 44 (2000)). Endothelial cells from pre-existing blood vessels or from circulating endothelial stem cells become activated to migrate, proliferate, and differentiate into structures with lumens, forming new blood vessels, in response to growth factor or hormonal cues, or hypoxic or ischemic conditions. (Takahashi et al., Nat. Med. 5:434-438 (1995)). During ischemia, such as occurs in cancer, the need to increase oxygenation and delivery of nutrients apparently induces the secretion of angiogenic factors by the affected tissue; and these factors stimulate new blood vessel formation. Several additional terms related to angiogenesis are defined below.

As used herein, the term "inhibiting angiogenesis," means reducing a level of angiogenesis in a tissue where angiogenesis is occurring, i.e., where new blood vessels are developing from pre-existing blood vessels. In embodiments, inhibiting angiogenesis refers to reducing the level of angiogenesis in a tumor (or cancer) to a level that is at least 10% lower than a level of angiogenesis in a corresponding control tissue, and preferably at least 15%, 20%, 25%, 30%, 35%, 40%, 45%, 50%, 55%, 60%, 65%, 70%, 75%, 80%, 85%, 90%, 95%, or 99% lower than the level of angiogenesis in the corresponding control tissue. A reduced level of angiogenesis need not, although it may, mean an absolute absence of angiogenesis. The level of angiogenesis may be determined using methods well known in the art, including, e.g., counting the number of blood vessels and/or the number of blood vessel branch points, as discussed herein and in the examples.

An alternative in vitro assay contemplated in some embodiments includes a tubular cord formation assay that shows growth of new blood vessels at the cellular level (D. S. Grant et al., Cell, 58:933-943 (1989)). Art-accepted in vivo assays that involve the use of various test animals, such as chickens, rats, mice, rabbits and the like may also be used. These in vivo assays include the chicken chorioallantoic membrane (CAM) assay, which is suitable for showing anti-angiogenic activity in both normal and neoplastic tissues (D. H. Ausprunk, Amer. J. Path. 79, No. 3:597-610 (1975); and L. Ossonowski and E. Reich, Cancer Res., 30:2300-2309 (1980)). Other conventional in vivo assays include the mouse metastasis assay, which demonstrates the ability of a compound to reduce the rate of growth of transplanted tumors in certain mice, or to inhibit the formation of tumors or preneoplastic cells in mice that are predisposed to cancer or that express chemically-induced cancer (M. J. Humphries et al., *Science*, 233:467-470 (1986); and M. J. Humphries et al., *J. Clin. Invest.* 81:782-790 (1988)). In some embodiments, angiogenesis can be measured according to attributes such as pericyte maturation and vascular remodeling, as described further herein.

As used herein, the term "hypoxia associated angiogenesis" or "hypoxia-induced angiogenesis" refers generally to the process of pathological angiogenesis in non-neoplastic disease states and is typically, although not necessarily, accompanied by a transition to a neoplastic state. Hypoxia-induced transcription factors (HIFs) induce the expression of angiogenic factors, including HIF-1alpha, VEGF, nitric oxide synthase, PDFG, Ang2, and others. As a result, hypoxia associated angiogenesis encompasses a well-known set of pathological conditions characterized by such a process. See, e.g., Pugh et al., *Nat. Med.* 9, 677-684 (2003); Fraisl et al., *Dev. Cell.* 16, 167-179 (2009); Ferrara et al., *Nature* 438, 967-974 (2005); Ferrara, N., *Cytokine Growth Factor Rev.* 21, 21-26 (2010). In some embodiments, the set of hypoxia associated angiogenesis pathologies includes, but is not limited to, cancers.

Unless otherwise specified in the disclosure, the terms "antibody" and "antibodies" broadly encompass naturally-occurring forms of antibodies (e.g., IgG, IgA, IgM, IgE), as well as recombinant antibodies (e.g., single-chain, humanized, and multi-specific antibodies) and fragments and derivatives of all of the foregoing, wherein such fragments and derivatives have at least an antigenic binding site. Antibody derivatives may comprise a protein or chemical moiety conjugated to an antibody.

Generally, an "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The term "CDR," and its plural "CDRs," refers to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions.

An antibody or antigen-binding portion thereof may be part of a larger immunoadhesion polypeptide, formed by covalent or noncovalent association of the antibody or antibody portion with one or more other proteins or peptides. Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, syngeneic, or modified forms thereof (e.g., humanized, chimeric, etc.). Antibodies may also be fully human. As used herein, the terms "monoclonal antibodies" and "monoclonal antibody composition" refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. In embodiments, antibodies may bind specifically or substantially specifically to Gal1 or VEGF2 polypeptides or fragments thereof. Accordingly, the term "human monoclonal antibody" refers to an antibody that displays a single binding specificity and that has variable and constant regions derived from human germline or non-germline immunoglobulin sequences. In some embodiments, human monoclonal antibodies may be produced by a hybridoma that includes a B cell obtained from a transgenic non-human animal, e.g., a transgenic mouse, having a genome comprising a human heavy chain transgene and a light chain transgene fused to an immortalized cell. In embodiments, antibodies may bind specifically or substantially specifically to Gal1 or VEGF2 polypeptides or fragments thereof.

The term "humanized antibody," as used herein, includes antibodies made by a non-human cell having variable and constant regions that have been altered to more closely resemble antibodies that would be made by a human cell, e.g., by altering a non-human antibody amino acid sequence to incorporate amino acids found in human germline immunoglobulin sequences. In embodiments, humanized antibodies may include amino acid residues not encoded by human germline immunoglobulin sequences (e.g., mutations introduced by random or site-specific mutagenesis in vitro or by somatic mutation in vivo), for example in the CDRs. As used herein, the term "humanized antibody" also includes antibodies in which CDR sequences derived from the germline of another mammalian species, such as a mouse, have been grafted onto human framework sequences.

As used herein, the term "recombinant human antibody" includes all human antibodies that are prepared, expressed, created or isolated by recombinant means, such as, for example: (a) antibodies isolated from an animal (e.g., a mouse) that is transgenic or transchromosomal for human immunoglobulin genes, or a hybridoma prepared as described further below; (b) antibodies isolated from a host cell transformed to express the antibody, e.g., from a transfectoma; (c) antibodies isolated from a recombinant, combinatorial human antibody library; and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, the term "heterologous antibody" is defined in relation to a transgenic non-human organism producing such an antibody. This term refers to an antibody having an amino acid sequence or an encoding nucleic acid sequence corresponding to that found in an organism not consisting of the transgenic non-human animal, and generally from a species other than the transgenic non-human animal.

As used herein, an "isolated antibody" is intended to refer to an antibody that is substantially free of other antibodies having different antigenic specificities (e.g., an isolated antibody that specifically binds to human Gal1 and is substantially free of antibodies that do not bind to Gal1). An isolated antibody that specifically binds to an epitope of human Gal1 may, however, have cross-reactivity to other Gal1 proteins, respectively, from different species. However, in some embodiments, the antibody maintains higher affinity and selectivity for human Gal1. In addition, an isolated antibody is typically substantially free of other cellular material and/or chemicals. In certain embodiments, a combination of "isolated" monoclonal antibodies having different specificities to human Gal1 may be included in a defined composition.

As used herein, the term "hypervariable region," "HVR," or "HV," refers to a region of an antibody-variable domain that is hypervariable in sequence and/or forms structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. See, e.g., Xu et al. *Immunity* 13, 37-45 (2000); and Johnson and Wu, *Methods in Molecular Biology* 248, 1-25 (2003). Indeed, naturally occurring camelid antibodies consisting of a heavy chain only are functional and stable in the absence of a light chain. See, e.g., Hamers-Casterman et al., *Nature* 363:446-448 (1993); and Sheriff et al., *Nature Struct. Biol.* 3, 733-736 (1996).

As used herein, the term "Fc region" is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to extend from an amino acid residue at position Cys226, or from Pro230, to the carboxyl-terminus thereof. Suitable native-sequence Fc regions for use in antibodies of the present disclosure include Fc regions of human IgG1, IgG2 (IgG2A, IgG2B), IgG3 and IgG4.

As used herein, "Fc receptor" or "FcR" is a receptor that binds to the Fc region of an antibody. A preferred FcR is a native sequence human FcR that binds to an IgG antibody and includes receptors of the FcRI, FcRII, and FcRII subclasses, including allelic variants and alternatively spliced forms of these receptors. FcRII receptors include Fc RIIA (an "activating receptor") and FcRIIB (an "inhibiting receptor"), which have similar amino acid sequences that differ primarily in the cytoplasmic domains thereof. Activating receptor FcRIIA contains an immunoreceptor tyrosine-based activation motif (ITAM) in its cytoplasmic domain. Inhibiting receptor FcRIIB contains an immunoreceptor tyrosine-based inhibition motif (ITIM) in its cytoplasmic domain (see M. Daeron, *Annu. Rev. Immunol.* 15:203-234 (1997)).

As used herein, the term "$K_D$" is intended to refer to the dissociation equilibrium constant of a particular antibody-antigen interaction. In embodiments, the binding affinity of antibodies may be measured or determined by standard antibody-antigen assays, for example, competitive assays, saturation assays, or standard immunoassays such as ELISA or RIA.

As used herein, the term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE assay instrument using human FAS and/or USP2a as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody that binds specifically to an antigen."

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells also may exist alone within an animal, or may be non-tumorigenic cancer cells, such as a leukemia cells. Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. In embodiments, the terms "cancer" or "tumor" may refer to LLC1 Lewis lung carcinoma, R1.1 T-cell lymphoma, or Daucnealiz cancer.

The term "coding region" refers to a region of a nucleotide sequence comprising codons that are translated into amino acid residues, whereas the term "noncoding region" refers to a region of a nucleotide sequence that is not translated into amino acids (e.g., 5' and 3' untranslated regions).

The term "dosage unit form" refers to physically discrete units suited as unitary dosages for the subjects to be treated; each unit containing a predetermined quantity of active compound calculated to produce the desired therapeutic effect in association with the required pharmaceutical carrier.

A molecule is "fixed" or "affixed" to a substrate if it is covalently or non-covalently associated with the substrate such that the substrate can be rinsed with a liquid (e.g. standard saline citrate, pH 7.4) without a substantial fraction of the molecule dissociating from the substrate.

As used herein, "Framework" or "FR" residues are those variable-domain residues other than the HVR residues as herein defined.

As used herein, the term "homologous" refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue.

As used herein, the term "host cell" is intended to refer to a cell into which a nucleic acid, such as a recombinant expression vector, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "inhibit" includes the decrease, limitation, or blockage, of, e.g., a particular action, function, or interaction.

As used herein, an "antisense" nucleic acid polypeptide comprises a nucleotide sequence that is complementary to a "sense" nucleic acid encoding a protein, e.g., complementary to the coding strand of a double-stranded cDNA polypeptide, complementary to an mRNA sequence, or complementary to the coding strand of a gene.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a Gal1 polypeptide or fragment thereof, in which the protein is separated from the cellular components of the cells from which it is isolated or recombinantly produced. In some embodiments, the language "substantially free of cellular material" includes preparations of a Gal1 protein or fragment thereof, having less than about 30% (by dry weight) of non-Gal1 protein (also referred to herein as a "contaminating protein"), more preferably less than about 20% of non-Gal1 protein, still more preferably less than about 10% of non-Gal1 protein, and most preferably less than about 5% non-Gal1 protein. When isolated antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM or IgG) that is encoded by heavy chain constant region genes.

As used herein, the term "modulate" includes up-regulation and down-regulation, e.g., enhancing or inhibiting a response.

As used herein, the term "nucleic acid" is intended to include DNA molecules and RNA molecules. A nucleic acid molecule may be single-stranded or double-stranded, but preferably is double-stranded DNA. As used herein, the term nucleic acid molecule is intended to include DNA molecules (e.g., cDNA or genomic DNA) and RNA molecules (e.g., mRNA) and analogs of the DNA or RNA generated using nucleotide analogs. As used herein, the term "isolated nucleic acid molecule" in reference to nucleic acids encoding antibodies or antibody portions (e.g., $V_H$, $V_L$, CDR3) that bind to Gal1, is intended to refer to a nucleic acid molecule in which the nucleotide sequences encoding the antibody or antibody portion are at least substantially free of other nucleotide sequences encoding antibodies or antibody portions that bind antigens other than Gal1, which other sequences may naturally flank the nucleic acid in human genomic DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. In some embodiments an "isolated" nucleic acid molecule is free of sequences which naturally flank the nucleic acid (i.e., sequences located at the 5' and 3' ends of the nucleic acid molecule) in the genomic DNA of the organism from which the nucleic acid is derived. For example, an "isolated" nucleic acid molecule, such as a cDNA molecule, can be substantially free of other cellular material, or culture medium, when produced by recombinant techniques, or substantially free of chemical precursors or other chemicals when chemically synthesized.

In embodiments, a nucleic acid molecule can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleic acid sequences can be prepared by standard synthetic techniques, e.g., using an automated DNA synthesizer.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "polypeptide fragment" refers to a polypeptide in which amino acid residues are deleted as compared to the reference polypeptide itself, but in which the remaining amino acid sequence is usually identical as to corresponding positions in the reference polypeptide. Such deletions may occur at one or more of the amino-terminus, internally, or at the carboxy-terminus of the reference polypeptide. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they can be no longer than and/or excluding such a range so long as they are less than the length of the full-length polypeptide. The VEGFR2-Gal1 interaction involves N-glycosylation sites as it is prevented, for example, by treatment with swainsonine or siRNA-mediated silencing of MGAT5 glycosyltransferase, which is responsible for generating complex N-glycans. A fragment can retain one or more of the biological activities of the reference polypeptide. In various embodiments, a fragment may comprise an enzymatic activity and/or an interaction site of the reference polypeptide. In embodiments, the fragment may have immunogenic properties. In embodiments, a Gal1 fragment may form a complex with a VEGFR2 polypeptide or a fragment thereof, and/or a VEGFR2 fragment is able to form a complex with a Gal1 polypeptide or a fragment thereof.

The term "probe" refers to any molecule that is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and other organic molecules.

As used herein, the term "rearranged" refers to a configuration of a heavy chain or light chain immunoglobulin locus wherein a V segment is positioned immediately adjacent to a D-J or J segment in a conformation encoding essentially a complete $V_H$ and $V_L$ domain, respectively. A rearranged immunoglobulin gene locus can be identified by comparison to germline DNA; a rearranged locus will have at least one recombined heptamer/nonamer homology element.

As used herein, the term "refractory" refers to cancer, cancerous cells, or a tumor that is resistant (i.e., does not respond completely, or loses or shows a reduced response over the course of treatment) to cancer treatment comprising at least a VEGF antagonist. A cancer or tumor that is refractory, as used herein, may refer to cancers and tumors diagnosed as being "resistant to anti-VEGF treatment." In certain embodiments, there is an increase in CD11b+Gr1+ cells in a refractory cancer or tumor, as compared to a cancer or tumor that is sensitive to treatments that include at least a VEGF antagonist, i.e., "sensitive" to anti-VEGF treatment.

As used herein, the term "response" is generally related to, for example, determining the effects on progression, efficacy, or outcome of a clinical intervention. In some embodiments, a response relates directly to a change (or cessation or alteration of change) in tumor mass and/or volume after initiation of clinical intervention (e.g., administration of an anti-Gal1 monoclonal antibody). For example, hyperproliferative disorder responses may be assessed according to the size of a tumor after systemic intervention compared to the initial size and dimensions as measured by CT, PET, mammogram, ultrasound or palpation. Response may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment may be done early after the onset of the clinical intervention, e.g., after a few hours, days, weeks or preferably after a few months. A typical endpoint for response assessment is upon termination of the clinical intervention or upon surgical removal of residual tumor cells and/or the tumor bed.

As used herein, "subject" refers to any healthy animal (e.g., mammal; e.g., human), or any animal (e.g., mammal; e.g., human) afflicted with a cancer or tumor refractive to anti-VEGF treatment. The term "subject" is interchangeable with "patient." The term "non-human animal" includes all vertebrates, e.g., mammals and non-mammals, such as non-human primates, sheep, dogs, cows, chickens, amphibians, reptiles, etc.

A "transcribed polynucleotide" or "nucleotide transcript" is a polynucleotide (e.g., an mRNA, hnRNA, a cDNA, or an analog of such RNA or cDNA) that is complementary to or homologous with all or a portion of a mature mRNA, made by transcription of a marker and post-transcriptional processing (e.g. splicing), if any, of the RNA transcript, and reverse transcription of the RNA transcript.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

The term "organized vasculature" means substantially branched blood vessels, or blood vessels with a normal or increased degree of branching, so as to promote blood supply to surrounding tissue. The term "disorganized vasculature" means substantially unbranched blood vessels, or blood vessels with a reduced degree of branching, so as to impair blood supply to surrounding tissue.

As used herein, the term "vector" refers to a nucleic acid capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors." In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve similar functions.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The "percent identity" between two sequences is a function of the number of identical positions shared by the sequences (i.e., % identity=# of identical positions/total # of positions×100), taking into account the number of gaps and the length of each gap that needs to be introduced for optimal alignment of the two sequences. The comparison of sequences and determination of percent identity between two sequences can be accomplished using a mathematical algorithm, as described in the non-limiting examples below.

INCORPORATION BY REFERENCE

U.S. Patent Application Publication No. 2013/0011409, which is a national stage application of PCT/US2010/056547, relates to compositions, kits, and methods for diagnosing, prognosing, monitoring, treating and modulating viral-associated PTLD (i.e., EBV-associated PTLD and hypoxia-associated angiogenesis disorders). The disclosure of the prior application PCT/US2010/056547 is hereby incorporated by reference herein in its entirety.

Any additional references (patent application publications, issued patents, or journal publications) cited in the present disclosure are also incorporated by reference herein in their entireties. Also incorporated by reference are the Figures and any polynucleotide and polypeptide sequences that reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov. The synthesis and sequence of the hybridoma cell line 8F4.F8.G7 is described in detail in U.S. patent application Ser. No. 13/509,466, which published as U.S. Patent Application Publication No. 2013/0011409 and is incorporated by reference herein in its entirety.

DETAILED DESCRIPTION

In the present disclosure, numerous details are set forth to provide an understanding of the present disclosure. However, it may be understood by those skilled in the art that the methods of the present disclosure may be practiced without these details and that numerous variations or modifications from the described embodiments are possible.

The present disclosure is based in part on a glycolysation-dependent pathway to modulate angiogenesis in response to the VEGF blockade, thus unexpectedly circumventing resistance to VEGF-targeted therapies.

Remodeling of the endothelial cell (EC) surface glycome selectively regulates signaling by Gal1, which, upon recognition of complex N-glycans on the VEGFR2, mimics VEGF-A function. The glycosylation-dependent pathway compensates for the absence of cognate ligand and preserves angiogenesis in response to anti-VEGF treatment because interactions between Gal1 and specific N-glycans decorating VEGFR2 can substitute for the absence of VEGF-A to promote receptor signaling and preserve angiogenesis in cancers and tumors refractory to anti-VEGF.

Specifically, vessels within anti-VEGF sensitive tumors exhibit high levels of α2-6-linked sialic acid, which prevents Gal1 signaling and angiogenesis. However, such anti-VEGF refractory tumors secrete increased Gal1 and their associated vasculature expresses higher amounts of β1-6GlcNAc-branched N-glycans and decreased α2-6 sialylation, which in turn facilitates Gal1 signaling and revascularization. Interruption of β1-6GlcNAc branching in ECs or silencing of tumor-derived Gal1 converts anti-VEGF refractory tumors into anti-VEGF-sensitive tumors, whereas elimination of α2-6-linked sialic acid confers resistance to anti-VEGF. Disruption of the Gal1-N-glycan axis promotes vascular remodeling, immune cell influx, and tumor growth inhibition. According to this glycosylation-dependent pathway, methods of the present disclosure relate to modulating angiogenesis so as to unexpectedly circumvent resistance of certain cancers (tumors) to VEGF-targeted therapies.

Modulating Angiogenesis

Aspects of the present disclosure pertain to methods of modulating Gal1 expression, activity, or interaction with its natural binding partner(s) for therapeutic purposes. In embodiments, a method of modulating angiogenesis in a cancer refractory to anti-VEGF comprises contacting a cancer cell refractory to anti-VEGF with an effective amount of an agent that modulates the interaction between Gal1 or a fragment thereof and its natural binding partner(s) to thereby modulate angiogenesis. Aspects of the present disclosure utilize the Gal1 gene sequence or fragments thereof, as well as gene products of the Gal1 gene and/or modulators thereof, e.g., antibodies that specifically bind to such Gal1 gene products, or fragments thereof.

Thus, referenced compositions (e.g., natural ligands, derivatives of natural ligands, small molecules, RNA, aptamers, peptides, peptidomimetics, glycan-related compounds, glycomimetics, antibodies) that specifically bind to the Gal1 gene or gene products, or fragments thereof may also be utilized as modulating agents in methods of the present disclosure.

Modulating Agents

In embodiments, agents that modulate interaction between Gal1 or a fragment thereof and its natural binding partner(s) are referred to as "modulating agents." Modulating agents according to embodiments can modulate (e.g., up or down regulate) expression and/or activity of gene products or fragments thereof encoded by the Gal1 gene or fragments thereof. Modulating agents include agents that: (a) block interactions between a Gal1 polypeptide or a fragment thereof and its natural binding partner(s) or a fragment(s) thereof; and (b) agents that increase the interactions between a Gal1 polypeptide or a fragment thereof and its natural binding partner(s) or a fragment(s) thereof.

Examples of modulating agents that inhibit the interaction of Gal1 with its natural binding partner(s) (i.e., "Gal1 antagonists") include, e.g., antisense Gal1 nucleic acid molecules, anti-Gal1 antibodies, and Gal1 inhibitors. Examples of modulating agents that stimulate interaction of Gal1 with its natural binding partner(s) (i.e., "Gal1 agonists") include, e.g., nucleic acid molecules encoding Gal1 polypeptides, multivalent forms of Gal1, and compounds that increase the expression of Gal1. In general, stimulation of Gal1 activity is desirable in situations in which Gal1 is abnormally downregulated and/or in which increased Gal1 activity is likely to have a beneficial effect. Likewise, inhibition of Gal1 activity is desirable in situations in which Gal1 is abnormally upregulated and/or in which decreased Gal1 activity is likely to have a beneficial effect.

Modulating agents used in methods of the disclosure include, e.g., a nucleic acid, a polypeptide, a naturally-occurring binding partner of a Gal1 polypeptide, a Gal1 antibody, a combination of Gal1 antibodies and antibodies against other immune related targets, a Gal1 agonist or antagonist, a peptidomimetic of a Gal1 agonist or antagonist, a Gal1 peptidomimetic, a glycan-related compound, a glycomimetic, a natural ligand and a derivatives thereof, an antisense nucleic acid molecule, RNAi molecule, shRNA or other small RNA molecule, triplex oligonucleotide, ribozyme, and other small molecules. In embodiments, an oligonucleotide complementary to the area around a Gal1 polypeptide translation initiation site can be synthesized. Embodiments also relate to a recombinant vector for expression of a Gal1 polypeptide.

Specific modulating agents for use in methods according to certain embodiments also include, without limitation, the antibodies, proteins, fusion proteins and small molecules described U.S. Patent Application Publication 2013/0011409 (incorporated by reference herein in its entirety). Alternative antibodies can be raised against Gal1 by well-known methods and may be used in embodiments of the invention.

Table 1 (including sequences of the hybridoma cell line 8F4.F8.G7) and Table 2 (including an analysis of the sequences obtained from the hybridomas) provided on pages 52-54 of U.S. Patent Application Publication 2013/0011409 are likewise incorporated by reference herein in their entireties, with relevant portions and sequences reproduced for convenience below. The hybridoma cell line 8F4.F8.G7 was deposited with the American Type Culture Collection having an address of 10801 University Boulevard, Manassas, Va. 20110-2209, U.S.A., and was received on Dec. 17, 2009 in accordance with the provisions of the Budapest Treaty on the International Recognition of the Deposit of Microorganisms for the Purposes of Patent Procedure under deposit number PTA-10535.

Gal1 monoclonal antibodies for use in embodiments may comprise heavy chain and light chain sequences, such as those identified in Table 1 of of U.S. Patent Application Publication No. 2013/0011409 (reproduced below), or fragments thereof.

```
Heavy Chain Variable (vH) DNA Sequence
                                      (SEQ ID NO: 5)
GAGGTTCAGCTGCAGCAGTCTGTGGCAGAGTTTGTGAGGCCAGGGG

CCTCAGTCAGGTTGTCCTGCACAGCTTCTGGCTTCAACATTAAAAA

CACCTATATACACTGGGTGAGGCAGAGGCCTGAACAGGGCCTGGAG

TGGATTGGAAAGATTGATCCTGCGAATGGTAATACTAAATATGTCC

CGGAGTTCCAGGGCAAGGCCACTATGACTGCGGACACATCCTCCAA

CACAGTCTACCTGCACCTCAGCAGCCTGACATCTGAGGACACTGCC

ATCTATTACTGTGTCGATGGTTACTACGGCTGGTATTTCGCTGTCT

GGGGCACAGGGACCACGGTCACCGTCTCCTCA

Heavy Chain Variable (vH) Amino Acid Sequence
                                      (SEQ ID NO: 6)
EVQLQQSVAEFVRPGASVRLSCTASGFNIKNTYIHWVRQRPEQGLE

WIGKIDPANGNTKYVPEFQGKATMTADTSSNTVYLHLSSLTSEDTA

IYYCVDGYYGWYFAVWGTGTTVTVSS
```

In the heavy chain variable amino acid sequence above, underlined portions correspond to CDR1 (SEQ ID NO: 7), CDR2 (SEQ ID NO: 8), and CDR3 (SEQ ID NO:9) protein sequences according to Kabat.

```
Light Chain Variable (vK) DNA Sequence
                                     (SEQ ID NO: 10)
CAGGCTGTTGTGACTCAGGAATCTGCACTCACCACATCACCTGGTG

AAACAGTCACACTCACTTGTCGCTCAAGCACTGGGGCTGTTACAAC

TAGTAACTATGCCAACTGGGTCCAAGAAAAACCAGATCATTTATTC

ACTGGTCTAATAGGTGCTACCAACAACCGAGCTCCAGGTGTTCCTG

CCAGATTCTCAGGCTCCCTGATTGGAGACAAGGCTGTCCTCACCAT

CACAGGGGCACAAACTGAGGATGAGGCAATATATTTCTGTGCTCTA

TGGTACAGAAACCATTTTATTTTCGGCAGTGGAACCAAGGTCACTG

TCCTC

Light Chain Variable (vK) Amino Acid Sequence
                                     (SEQ ID NO: 11)
QAVVTQESALTTSPGETVTLTCRSSTGAVTTSNYANWVQEKPDHLF

TGLIGATNNRAPGVPARFSGSLIGDKAVLTITGAQTEDEAIYFCAL

WYRNHFIFGSGTKVTVL
```

In the light chain variable amino acid sequence above, underlined portions correspond to DDR1 (SEQ ID NO: 12), CDR2 (SEQ ID NO: 13), and CDR3 (SEQ ID NO: 14) protein sequences according to Kabat.

A. Nucleic Acids

Isolated nucleic acid molecules according to embodiments may comprise, e.g., a nucleotide sequence having at least about 70%, 75%, 80%, 85%, 90%, 91%, 92%, 93%, 94%, 95%, 96%, 97%, 98%, 99% or more sequence identity with the target full-length nucleotide sequences described herein, including those provided in Table 1 of U.S. Patent Application Publication No. 2013/0011409.

The expression characteristics of nucleic acid molecules according to embodiments within a cell line or microorganism may be modified by inserting a heterologous DNA regulatory element into the genome of a stable cell line or cloned microorganism such that the inserted regulatory element is operatively linked with a nucleic acid molecule. For example, a heterologous regulatory element may be inserted into a stable cell line or cloned microorganism, such that it is operatively linked with a nucleic acid molecule described herein, using techniques, such as targeted homologous recombination, which are well known to those of skill in the art, and described in, e.g., U.S. Pat. No. 5,272,071; PCT Publication No. WO 91/06667, published May 16, 1991.

In embodiments, nucleic acid compositions from either cDNA, genomic or mixtures thereof, while often in a native sequence (except for modified restriction sites and the like), may be mutated, in accordance with standard techniques to provide gene sequences. For coding sequences, these mutations may affect amino acid sequence as desired. For coding sequences, these mutations may affect amino acid sequences as desired. In particular, DNA sequences substantially homologous to or derived from native V, D, J, constant switches and other such derived sequences are alssequences described herein are contemplated (where "derived" indicates that a sequence is identical to or modified from another sequence).

In view of the foregoing, a nucleotide sequence of a DNA or RNA coding for a fusion protein or polypeptide described herein can be used to derive a fusion protein or polypeptide amino acid sequence, using the genetic code to translate the DNA or RNA into an amino acid sequence. Likewise with respect to fusion protein or polypeptide amino acid sequences, corresponding nucleotide sequences that can encode such fusion proteins or polypeptides can be deduced from the genetic code (which, because of its redundancy, will produce multiple nucleic acid sequences for any given amino acid sequence). Thus, description and/or disclosure herein of a nucleotide sequence that encodes a fusion protein or polypeptide should be understood to also include description and/or disclosure of the amino acid sequence encoded by the nucleotide sequence. Similarly, description and/or disclosure of a fusion protein or polypeptide amino acid sequence described herein should be considered to also include description and/or disclosure of all possible nucleotide sequences that can encode the amino acid sequence.

The skilled artisan will further appreciate that changes can be introduced by mutation into a nucleic acid molecule employed in embodiments (e.g., including the sequences in Table 1 of U.S. Patent Application Publication No. 2013/0011409), thereby leading to changes in the amino acid sequence of the encoded polypeptides without altering the functional ability of the polypeptides.

In embodiments, the isolated nucleic acid is comprised within a vector.

Isolated nucleic acid molecules described herein can be used, e.g., to express a Gal1 polypeptide or a fragment thereof (e.g., via a recombinant expression vector in a host cell in gene therapy applications), to detect Gal1 mRNA or a fragment thereof (e.g., in a biological sample) or a genetic alteration in a Gal1 gene, and to contact a cancer cell refractory to anti-VEGF with an effective amount thereof to modulate angiogenesis in the cancer cell. Moreover, the Gal1 nucleic acid molecules described herein can be used in the treatment and prophylaxis methods described herein.

B. Polypeptides

Polypeptides for use in embodiments include isolated polypeptides (e.g., including the sequences in Table 1 of U.S. Patent Application Publication No. 2013/0011409) and biologically active portions thereof. In embodiments, such polypeptides can be isolated from cells or tissue sources by an appropriate purification scheme using standard protein purification techniques, or can be produced by recombinant DNA techniques, or can be chemically synthesized using standard peptide synthesis techniques.

Peptides for use in embodiments can be produced, typically by direct chemical synthesis, and used e.g., as antagonists of the interactions between a Gal1 polypeptide or a fragment thereof and a natural binding partner of the Gal1 polypeptide or a fragment thereof. Peptides can be produced as modified peptides, with nonpeptide moieties attached by covalent linkage, such as to the N-terminus and/or C-terminus. In some embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides according to the disclosure can be used therapeutically to treat disease, e.g., by altering co-stimulation in a patient.

Amino acid sequences disclosed herein enable those skilled in the art to produce polypeptides with corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al., Molecular Cloning: A Laboratory Manual, 2nd ed., Cold Spring Harbor, N.Y. (1989) (the disclosure of which is incorporated by reference herein in its entirety).

In embodiments, mutant polypeptides can be assayed for the ability to bind to and/or modulate the activity of Gal1 by methods known to persons skilled in the art. Suitable media for cell culture are also well known in the art. Protein and peptides can be isolated from cell culture media, host cells, or both using techniques known in the art for purifying proteins and peptides. Techniques for transfecting host cells and purifying proteins and peptides are known in the art.

As described herein, a Gal1 polypeptide or fragment thereof may be an agent that modulates interaction between Gal1 and a natural binding partner of Gal1 so as to modulate angiogenesis in cancers and tumors refractory to anti-VEGF treatment. Moreover, the polypeptides, polypeptide homologues, antibodies, and fragments thereof can be used in the methods of treatment and prophylaxis according to embodiments described herein.

Gal1 polypeptides or fragments thereof may be used according to various methods as described herein, as well as to, for example, screen for drugs or compounds that modulate Gal1 activity due to insufficient or excessive production of Gal1 polypeptide or a fragment thereof.

C. Glycan-Related Compounds

Similarly, glycan-related compounds and/or glycomimetics can be used in methods of the present disclosure and according to well known methods in the art. See, e.g., U.S. Patent Application Publications Nos. 2008/0200406, 2008/0112955, and 2004/092015. For example, glycan-related compounds or glycomimetic analogs of proteins or peptides described herein can be used to modulate immune responses and/or hypoxia-associated angiogenesis.

D. Small Molecules

Also encompassed by the present disclosure are small molecules that can modulate (either enhance or inhibit) interactions, e.g., the interactions between a Gal1 polypeptide or a fragment thereof and its natural binding partner(s) or a fragment(s) thereof. Small molecules of the present disclosure can be obtained using any of numerous approaches in combinatorial library methods known in the art, including: spatially addressable parallel solid phase or solution phase library methods; synthetic library methods requiring deconvolution; the "one-bead one-compound" library method; and synthetic library methods using affinity chromatography selection. See Lam, K. S., *Anticancer Drug Des.* 12:145 (1997).

E. Antibodies

In embodiments, monoclonal antibodies, or antigen-binding fragments thereof, may be chimeric, humanized, composite, or human. Fully human and chimeric antibodies employed herein include IgG2, IgG3, IgE, IgA, IgM, and IgD antibodies. Similar plasmids can be constructed for expression of other heavy chain isotypes, or for expression of antibodies comprising lambda light chains.

In embodiments, the monoclonal antibody, or antigen-binding fragment thereof, is detectably labeled, comprises an effector domain, comprises an Fc domain, is a single-chain antibody, and/or is a Fab fragment.

In embodiments, the monoclonal antibody, or antigen-binding fragment thereof, inhibits the binding of commercial antibody to Gal1. In embodiments, monoclonal antibody, or antigen-binding fragment thereof, reduces or inhibits at least one Gal1 activity (e.g., binding to beta-galactosides) relative to the absence of the monoclonal antibody or antigen-binding fragment thereof. Such antibodies and antigen-binding fragments thereof act as Gal1 inhibitors and may therefore be used to both detect the presence of Gal1 and to inhibit Gal1 activity without the need for introduction of an additional Gal1 inhibitor.

Alternatively, a Gal1 inhibitory antibody or antigen-binding fragment thereof may be used in combination with another Gal1 inhibitor, such as in a composition for inhibiting Gal1 activity or as administered, separately or in combination, to a subject as part of a method to inhibit Gal1 activity.

Anti-Gal1 antibodies may be conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. In embodiments, conjugated anti-Gal1 antibodies may be used diagnostically or prognostically to monitor poly-peptide levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, biolu-minescent materials, and radioactive materials.

Techniques for conjugating therapeutic moiety to antibodies are well known. See, e.g., Amon et al., "Monoclonal Antibodies For Immunotargeting Of Drugs In Cancer Therapy," in *Monoclonal Antibodies And Cancer Therapy*; Reisfeld et al. (eds.), pp. 243-56, Alan R. Liss, Inc. (1985)).

Without being bound by theory, it is believed that antibodies used in methods of the disclosure have at least one of the CDRs (complementarity determining regions) that participate in binding to the Gal1 polypeptide. Antibodies described herein may, for example, be specific to human Gal1 (i.e., not cross-reactive with Gal1 molecules in other species). Accordingly, anti-human Gal1 antibodies administered according to embodiments recognize human Gal1 with higher specificity and sensitivity. Such antibodies are suitable for, among other therapeutic uses, Western blotting (or immunoblotting), immunohistochemistry (IHC), detection of denatured or fixed forms of Gal1, ELISA assays, and RIA assays.

It is well known in the art that antibody heavy and light chain CDR3 domains play a particularly important role in the binding specificity/affinity of an antibody for an antigen, recombinant antibodies as set forth herein preferably comprise the heavy and light chain CDR3s of variable regions of the present disclosure (e.g., including the sequences of Table 1 of U.S. Patent Application Publication No. 2013/0011409, or portions thereof). The antibodies can comprise the CDR2s of variable regions according to the present disclosure (e.g., including the sequences of Table 1 of U.S. Patent Application Publication No. 2013/0011409, or portions thereof). The antibodies can also comprise the CDR1s of variable regions according to the disclosure (e.g., including the sequences of Table 1 of U.S. Patent Application Publication No. 2013/0011409, or portions thereof). In other embodiments, the antibodies can comprise any combinations of the CDRs.

In embodiments, an antibody, monoclonal antibody, or an antigen-binding fragment thereof as used in methods described herein may comprise a heavy chain variable nucleotide or amino acid sequence having at least about 80%, or at least 85%, or at least 90%, or at least 95% sequence identity with the heavy chain variable nucleotide sequence of SEQ ID NO: 5 or the heavy chain variable amino acid sequence of SEQ ID NO: 6; or a light chain variable nucleotide or amino acid sequence having at least about 80%, or at least 85%, or at least 90%, or at least 95% sequence identity with the light chain variable nucleotide sequence of SEQ ID NO: 10 or the light chain variable amino acid sequence of SEQ ID NO: 11.

A non-limiting example of a modulating agent for use in embodiments includes the neutralizing Gal1-specific monoclonal antibody F8.G7.

In certain embodiments, monoclonal antibodies may be produced using a variety of known techniques, such as the standard somatic cell hybridization technique described by Kohler and Milstein, *Nature* 256:495 (1975). Furthermore, any of the many well known protocols used for fusing lymphocytes and immortalized cell lines can be used to generate an anti-Gal1 monoclonal antibody. See, e.g., Gal-fre, G. et al., *Nature* 266:55052 (1977); Gefter et al. (1977); Lerner, *Yale J. Biol. Med.* 54, 387-402 (1981); Kenneth (1980). Moreover, the ordinary skilled artisan will appreciate that there are many variations of such methods that also would be useful in carrying out the invention.

F. Selection of Modulating Agents

The present disclosure also relates, in part, to selecting agents (e.g., antibodies, nucleic acids, peptides, fusion proteins, small molecules, glycan-related compounds) that modulate an immune response by modulating interactions between a Gal1 polypeptide or a fragment thereof and its natural binding partner(s) or fragment(s) thereof. In embodiments, a method for identifying an agent to modulate an immune response and/or hypoxia associated angiogenesis entails determining the ability of the agent to modulate, e.g., enhance or inhibit, the interactions between a Gal1 polypeptide or a fragment thereof and its natural binding partner(s) or a fragment(s) thereof. In embodiments, a method for identifying an agent to decrease an immune response entails determining the ability of a candidate agent to enhance the interactions between a Gal1 polypeptide or a fragment thereof and its natural binding partner(s) or a fragment(s) thereof. In embodiments, a method for identifying an agent that decreases hypoxia associated angiogen-esis entails determining the ability of the candidate agent to inhibit interactions between a Gal1 polypeptide or a fragment thereof and its natural binding partner(s) or a fragment(s) thereof.

In embodiments, the modulatory agents may function as "blocking" agents. Determining the ability of blocking agents (e.g., antibodies, fusion proteins, peptides, and small molecules) to antagonize interaction between a given set of polypeptides can be accomplished by determining the activity of one or more members of the set of interacting molecules. For example, the activity of Gal1 can be determined by detecting induction of a cellular second messenger (e.g., H-Ras), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by a Gal1 polypeptide or a fragment thereof. Determining the ability of the blocking agent to bind to or interact with said polypeptide can be accomplished by measuring the ability of an agent to modulate immune responses, for example, by detecting changes in type and amount of cytokine secretion, changes in apoptosis or proliferation, changes in gene expression or activity associated with cellular identity, or by interfering with the ability of said polypeptide to bind to antibodies that recognize a portion thereof.

A number of art-recognized methods are known to determine whether a candidate agent can reduce hypoxia associated angiogenesis. For example, endothelial cell adhesion and migration are known to regulate endothelial cell survival, proliferation, and motility during new blood vessel growth in normal and pathologic conditions that involve angiogenesis.

The term "endothelial cell adhesion" as used herein refers to the adhesion of an endothelial cell to one or more components of the extracellular matrix (e.g., fibronectin, collagens I-XVIII, laminin, vitronectin, fibrinogen, osteopontin, Del 1, tenascin, von Willebrands' factor, etc.), to a ligand which is expressed on the cell surface (e.g., VCAM, ICAM, L1-CAM, VE-cadherin, integrin a2, integrin a3, etc.) and/or to another cell (e.g., another endothelial cell, a fibroblast cell, a stromal cell, a tumor cell, etc.). The term "endothelial cell migration" as used herein refers to the translocation of an endothelial cell across one or more components of the extracellular matrix (e.g., fibronectin, collagens I-XVIII, laminin, vitronectin, fibrinogen, osteopontin, Del 1, tenascin, von Willebrands's factor, etc.), or along the surface of another cell (e.g., another endothelial cell, a fibroblast cell, a stromal cell, a tumor cell, etc.).

The terms "inhibiting endothelial cell adhesion" and "reducing endothelial cell adhesion" refer to reducing the level of adhesion of an endothelial cell to one or more components of the extracellular matrix (e.g., fibronectin, collagens I-XVIII, laminin, vitronectin, fibrinogen, osteopontin, Del 1, tenascin, von Willebrands's factor, etc.), and/or to another cell (e.g., another endothelial cell, a fibroblast cell, a stromal cell, a tumor cell, etc.) to a quantity which is preferably 10% less than, more preferably 50% less than, yet more preferably 75% less than, even more preferably 90% less than, the quantity in a corresponding control endothelial cell, or at the same level that is observed in a control endothelial cell. A reduced level of endothelial cell adhesion need not, although it may, mean an absolute absence of cell adhesion. The level of endothelial cell adhesion may be determined using methods well known in the art.

For example, a Gal1 polypeptide or a fragment thereof and its natural binding partner(s) or a fragment(s) thereof can be used to form an assay mixture and the ability of a polypeptide to block this interaction can be tested by determining the ability of a Gal1 polypeptide or a fragment thereof to bind to the Gal1 natural binding partner(s) or a fragment(s) thereof, by a method a determining direct binding. Determining the ability of a Gal1 polypeptide or a fragment thereof and its natural binding partner(s) or a fragment(s) thereof can also be accomplished using a technology such as real-time Biomolecular Interaction Analysis (BIA) (see Sjolander, S. and Urbaniczky, C., *Anal. Chem.* 63:2338-2345 (1991); and Szabo et al., *Curr. Opin. Struct. Biol.* 5:699-705 (1995)). As used herein, "BIA" is a technology for studying biospecific interactions in real time, without labeling any of the interactants (e.g., BIAcore).

Pharmaceutical Compositions

Gal1 modulating agents (i.e., agents that inhibit or promote the interactions between a Gal1 polypeptide and its natural binding partner(s) or a fragment thereof) as described herein can be incorporated into pharmaceutical compositions suitable for administration to a subject according to methods further disclosed herein. Such compositions typically comprise the Gal1 modulating agent in combination with a pharmaceutically acceptable carrier. Specifically, pharmaceutical compositions according to certain embodiments may comprise an antibody, a peptide, a fusion protein or a small molecule and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In embodiments, the pharmaceutical composition may comprise, as an active ingredient, an agent that inhibits interaction between Gal1 and its natural binding partner(s) (e.g., a modulating agent as described herein) and a pharmaceutically acceptable carrier. The carrier may be one or more of a diluent, adjuvant, excipient, or vehicle with which the agent is administered. In embodiments, the carrier may be a sterile liquid, such as water and/or oils, including those of petroleum, animal, vegetable, or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition may include minor amounts of wetting or emulsifying agents, or pH buffering agents.

In embodiments, a pharmaceutical composition is formulated to be compatible with its intended route of administration. Suitable routes of administration include, e.g., parenteral, intravenous, intradermal, subcutaneous, oral, inhalation, transdermal (topical), transmucosal, and rectal administration.

In some embodiments, a pharmaceutical composition may be formulated as a solution or suspension for parenteral, intradermal, or subcutaneous applications, and can include the following components: a sterile diluent such as water for injection, saline solution, fixed oils, plyethylene, glycols, glycerin, propylene glycol or other synthetic solvents; antibacterial agents such as benzyl alcohol or methyl parabens; antioxidants such as as ascorbic acid or sodium bisulfite; chelating agents such as ethylenediaminetetraacetic acid; buffers such as acetates, citrates or phosphates and agents for the adjustment of tonicity such as sodium chloride or dextrose. Pharmaceutical compositions for parenteral administration can be enclosed in ampoules, disposable syringes or multiple dose vials made of glass or plastic.

In some embodiments, a pharmaceutical composition may be formulated as a sterile aqueous solution suitable for injectable use (where water soluble), or as a dispersios and/or sterile powder for the extemporaneous preparation of a sterile injectable solution or dispersion. For intravenous administration, suitable carriers include physiological saline, bacteriostatic water, CREMOPHOR EL (BASF, Parsippany, N.J.) or phosphate buffered saline (PBS). In all cases, the composition should be sterile and should be fluid to the extent that easy syringeability exists. It must also be stable under the conditions of manufacture and storage and should be preserved against the contaminating action of microorganisms such as bacteria and fungi. The carrier can be a solvent or dispersion medium containing, for example: water, ethanol, polyol (e.g., glycerol, propylene glycol, and liquid polyethylene glycol, and the like), and suitable mixtures thereof. Proper fluidity of such solutions can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In embodiments, it may be desirable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Pharmaceutical compositions according to embodiments described herein may be prepared by incorporating the active ingredient(s) (i.e., at least the modulating agent that inhibits the interactions between a Gal1 polypeptide or a fragment thereof and its natural binding partner(s) or a fragment(s) thereof) in a required amount in an appropriate solvent with one or a combination of ingredients enumerated above, as necessary, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, preferred methods of preparation include vacuum drying and freeze-drying, which yield a powder of the active ingredient plus any additional desired ingredient from a previously sterile-filtered solution thereof.

Oral compositions generally include an inert diluent or an edible carrier. Such oral compositions may be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, compounds may be delivered in the form of an aerosol spray from a pressured container or dispenser which contains a suitable propellant, e.g., a gas such as carbon dioxide, or a nebulizer.

In certain embodiments, systemic administration may be performed by transmucosal or transdermal means. For transmucosal or transdermal administration, penetrants appropriate to the barrier to be permeated are used in the formulation to be administered. Such penetrants are generally known in the art and—for transmucosal administration—include, e.g., detergents, bile salts, and fusidic acid derivatives. Such transmucosal administration can be accomplished through the use of nasal sprays or suppositories. For transdermal administration, the active ingredient(s) are formulated into ointments, salves, gels and/or creams, as generally known in the art.

The pharmaceutical compositions comprising the active ingredient(s) described herein may also be prepared in the form of suppositories (e.g., with conventional suppository bases such as cocoa butter and other glycerides) or retention enemas for rectal delivery.

In embodiments, the modulating agents may be prepared with carriers that will protect the compound against rapid elimination from the body, such as a controlled release formulation, including implants and microencapsulated delivery systems. Biodegradable, biocompatible polymers can be used, such as, e.g., ethylene vinyl acetate, polyanhydrides, polyglycolic acid, collagen, polyorthoesters, and polylactic acid. Methods for preparation of such formulations should be apparent to those skilled in the art. Such materials can also be obtained commercially from Alza Corporation and Nova Pharmaceuticals, Inc. Liposomal suspensions, including liposomes targeted to infected cells with monoclonal antibodies to viral antigens, can also be used as pharmaceutically acceptable carriers. These can be prepared according to methods known to those skilled in the art, as described in, e.g., U.S. Pat. No. 4,522,811.

In certain embodiments, pharmaceutical compositions for administration to a subject having a cancer refractory to anti-VEGF treatment may comprise a pharmaceutically acceptable carrier, an anti-Gal1 agent (e.g., an antibody) in a therapeutically effective amount, and an anti-VEGF agent (e.g., antibody) in a therapeutically effective amount. In such embodiments, an anti-Gal1 antibody may be administered in combination with an anti-VEGF antibody and/or other compounds. As demonstrated by the experimental results discussed further below, administration of an anti-Gal1 antibody and an anti-VEGF antibody results in synergistic effects. Co-administration as used herein is not limited to simultaneous administration, but includes sequential administration of an anti-Gal1 agent and an anti-VEGF agent.

In some embodiments, the compositions may include supplemental active compounds and, for example, two or more active ingredients (agents that modulate interaction between Gal1 or a fragment thereof and its natural binding partner(s), such as, e.g., the modulating agents described herein). Supplementary active compounds may also be incorporated into the compositions.

In embodiments, the pharmaceutical composition comprises an agent that modulates interaction between Gal1 or a fragment thereof and its natural binding partner(s) (i.e., an anti-Gal1 modulating agent). The agent may be a small molecule, such as peptides, amino acids, amino acid analogs, polynucleotides, polynucleotide analogs, and fragments thereof. It is understood that appropriate doses of small molecule agents depends upon various factors within the scope of knowledge of the ordinary skilled physician, veterinarian, or researches. The dose(s) of the small molecule will vary, for example, depending upon the identity, size, and condition of the subject or sample being treated with the pharmaceutical composition, as well as upon the route by which the composition is to be administered and the desired effect of the small molecule.

Exemplary doses may include milligram or microgram amounts of the anti-Gal1 modulating agent as small molecule per kilogram of the subject or sample weight. In embodiments, does may include about 1 microgram to about 750 milligrams per kilogram, about 100 micrograms to about 500 milligrams per kilogram, about 500 micrograms to about 100 milligrams per kilogram, or about 1 milligram to about 50 milligrams per kilogram, or about 50 micrograms to about 100 micrograms per kilogram.

The pharmaceutical compositions can be included in a container, pack, or dispenser together with instructions for administration.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Conjugates of the present disclosure can be used for modifying a given biological response; the drug moiety is not to be construed as limited to classical chemical therapeutic agents. For example, the drug moiety may be a protein or polypeptide possessing a desired biological activity. In embodiments, such polypeptides may include, e.g., a toxin, such as abrin, ricin A, *pseudomonas* exotoxin, or diphtheria toxin; a protein, such as tumor necrosis factor, alpha-interferon, beta-interferon, nerve growth factor, platelet derived growth factor, or tissue plasminogen activator; or biological response modifiers, such as, e.g., lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

The above described modulating agents may be administered in the form of expressible nucleic acids that encode said agents. Such nucleic acids and the compositions in which they are contained are also encompassed by the present disclosure. For instance, nucleic acid molecules can be inserted into vectors and used as gene therapy vectors. Gene therapy vectors can be delivered to a subject by, for example, intravenous injection, local administration (see U.S. Pat. No. 5,328,470) or by stereotactic injection (see Chen et al., *Proc. Natl. Acad. Sci. USA* 91:3054-3057 (1994). Pharmaceutical compositions of the gene therapy vectors may include the gene therapy vector in an acceptable diluent, or may further include a slow release matrix in which the gene delivery vehicle is imbedded. Alternatively, where the complete gene delivery vector can be produced intact from recombinant cells, the pharmaceutical composition can include one or more cells which produce the gene delivery system.

Methods

The present disclosure relates to treatment and prophylactic methods of subjects afflicted or susceptible to becoming afflicted with a cancer (or tumor) refractory to anti-VEGF treatment.

In embodiments, a method for treating a subject having a cancer refractory to anti-VEGF treatment comprises administering to the subject an effective amount of an agent that inhibits the interaction between Gal1 and its natural binding partner(s). Examples of such agents include modulating agents as described herein (e.g., antisense nucleic acid molecules, small RNAs, antibodies that recognize and block Gal1, a combination of antibodies that recognize and block Gal1 and antibodies that recognize and block other immune- and/or angiogenesis-related targets, compounds that block the interactions between a Gal1 polypeptide or a fragment thereof and its natural binding partner(s) or a fragment(s) thereof, etc.). According to methods of the disclosure, the modulating agents may be administered in the form of expressible nucleic acids that encode such agents, inserted into vectors delivered to a subject by intravenous injection, or in a pharmaceutical composition administered to the subject.

In embodiments, a method of treating a subject afflicted with a cancer (or tumor) refractory to anti-VEGF treatment comprises administering to the subject an effective amount of a modulating agent as described herein. In embodiments, administering of the agent is effective to: (a) slowing or inhibiting growth of the cancer; (b) preventing spreading of the cancer; (c) preventing recurrence of a previously spread tumor associated with the cancer; (d) preventing spreading of one or more metastases associated with the cancer; (e) reducing a size of a tumor associated with the cancer; and/or (f) preventing the recurrence of cancer that has been previously treated.

In treatment methods of the disclosure, the administration of a therapeutically effective amount of the agent in the cancer cell results in the level of angiogenesis in the cancer being reduced by at least 10% with respect to a level of angiogenesis in a corresponding control cancer. In embodiments, interaction between Gal1 or a fragment thereof and its natural binding partner(s) is inhibited so that angiogenesis in the cancer cell is reduced by at least 20%, at least 30%, at least 40%, at least 50%, at least 60%, at least 70%, at least 80%, or at least 90% of a level of angiogenesis in a corresponding control cancer cell.

In embodiments, the treatment methods are for treating a subject having a cancer refractory to anti-VEGF treatment, and more specifically, a cancer known to be refractory to anti-VEGF treatment. In embodiments, the subject has a cancer refractory to anti-VEGF treatment selected from the group consisting of LLC1 Lewis lung cancer, T-cell lymphoma (R1.1), and pancreatic cancer.

In performing any of the methods described herein, it is within the scope of the present disclosure to up-regulate an immune response by administering one or more additional agents. For example, other agents known to stimulate the immune response, such as cytokines, adjuvants, or stimulatory forms of co-stimulatory molecules or their ligands, can be used in conjunction with an agent that inhibits Gal1 activity or a Gal1 polypeptide or a fragment thereof and its natural binding partner(s) or a fragment(s) thereof.

In embodiments, immune modulating agents of the present disclosure are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein.

Depending on the route of administration, the active compound (i.e., modulating agents described herein) may be coated in a material to protect the compound from the action of enzymes, acids and other natural conditions which may inactivate the compound. For example, administering agents according to methods of the present disclosure by modes other than parenteral administration, it may be desirable to coat the agent or co-administer the agent with a material to prevent its inactivation.

In some embodiments, the agent may be administered to an individual in an appropriate carrier, diluent or adjuvant, co-administered with enzyme inhibitors, or in an appropriate carrier such as liposomes. Pharmaceutically acceptable diluents include saline and aqueous buffer solutions. Adjuvant is used in its broadest sense and includes any immune stimulating compound such as an interferon. Examples of adjuvants that may be used in embodiments of the present disclosure include, e.g., resorcinols, non-ionic surfactants such as polyoxyethylene oleyl ether and n-hexadecyl polyethylene ether. Examples of enzyme inhibitors that may be used in embodiments of the present disclosure include, e.g., pancreatic trypsin inhibitor, diisopropylfluorophosphate (DEEP) and trasylol. Examples of liposomes that may be used in embodiments include, e.g., water-in-oil-in-water emulsions as well as conventional liposomes (Sterna et al., *J. Neuroimmunol.* 7:27 (1984)).

The agent may also be administered parenterally or intraperitoneally. Dispersions can also be prepared in glycerol, liquid polyethylene glycols, and mixtures thereof, and in oils. These preparations may contain a preservative to prevent the growth of microorganisms.

In some embodiments, it may be desirable to further administer one or more additional agent(s) that downregulate angiogenesis and/or upregulate immune responses, for example, forms of B7 family members that transduce signals via co-stimulatory receptors, in order to further augment the immune response. In embodiments, such additional agent(s) may include anti-angiogenesis agents, such as an anti-VEGF antibody.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

It is advantageous to formulate parenteral compositions in dosage unit form for ease of administration and uniformity of dosage. The dosage unit forms according to embodiments of the present disclosure are dictated by, and directly dependent on, (a) the unique characteristics of the active compound and the particular therapeutic effect to be achieved, and (b) the limitations inherent in the art of compounding such an active compound for the treatment of an anti-VEGF resistant cancer or tumor in a subject.

Data obtained from cell culture assays and animal studies can be used in formulating a range of dosages for use in humans or other animals. The dosage of such compounds lies preferably within a range of circulating concentrations that include the ED50 with little or no toxicity. The dosage may vary within this range depending upon the dosage form employed and the route of administration utilized. For any compound used in the methods of the present disclosure, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans or other animals. Levels in plasma can be measured, for example, by high performance liquid chromatography.

Modulating agents administered according to methods of the disclosure may, for example, be in the form of small molecules. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including hetero-organic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the scope of knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the present disclosure, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

As used herein, an "effective amount" of an agent that inhibits the interaction between Gal1 and its natural binding partner(s) means an amount that is "effective" at dosages and for periods of time necessary to achieve the desired result.

For example, a therapeutically active amount of a Gal1 blocking antibody may vary according to factors such as the cancer disease state, age, sex, and weight of the subject, and the ability of peptide to elicit a desired response in the individual. Dosage regimens can similarly be adjusted to provide the optimum therapeutic response. For example, several divided doses can be administered daily or the dose can be proportionally reduced as indicated by the exigencies of the therapeutic situation.

In embodiments, the agent that modulates angiogenesis or inhibits the interaction between Gal1 or a fragment(s) thereof and its natural binding partner(s) or a fragment(s) thereof in a cancer refractory to anti-VEGF may be a modulating agent as described herein. An effective dosage of the modulating agent may be from about 0.001 to 30 mg/kg body weight, or from about 0.01 to 25 mg/kg body weight, or from about 0.1 to 20 mg/kg body weight, or from about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and the presence of other diseases.

In embodiments, treating a subject with a therapeutically effective amount of an agent that modulates or inhibits interaction between Gal1 or fragment(s) thereof and its natural binding partner(s) or fragment(s) thereof may include a single treatment or, preferably, may include a series of treatments.

For example, an antibody may be administered to the subject having a cancer (or tumor) refractory to anti-VEGF treatment according to methods of the present disclosure in a dosage as noted above one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

In certain embodiments, an agent may be administered to a subject having a cancer (or tumor) refractory to anti-VEGF treatment in combination therapy with, e.g., chemotherapeutic agents, hormones, antiangiogens, radiolabelled compounds, or with surgery, cryotherapy, and/or radiotherapy. The antibody may be administered in conjunction with other forms of conventional therapy, concurrently with, pre- or post-conventional therapy. For example, the antibody may be administered with a therapeutically effective dose of chemotherapeutic agent. In some embodiments, the antibody may be administered in conjunction with chemotherapy to enhance the activity and efficacy of the chemotherapeutic agent. The Physicians' Desk Reference (PDR) discloses dosages of chemotherapeutic agents that may be used in the treatment of various cancers.

In embodiments, the method for treating a subject having a cancer refractory to anti-VEGF treatment comprises administering to the subject an effective amount of an agent that inhibits the interaction between Gal1 or a fragment(s) thereof and its natural binding partner(s) or a fragment(s) thereof a pharmaceutical composition, the concentration of the agent in the pharmaceutical composition being dependent on the dosage regiment and mode of administration prescribed by a physician.

Treatment methods of the disclosure result in the cancer (or tumor) that is refractive to anti-VEGF treatment becoming sensitive to anti-VEGF treatment. Embodiments therefore also relate to monitoring the resistance of a cancer (or tumor) to VEGF-targeted therapies in a subject, comprising detecting in a subject sample at a first point in time the level of expression of Gal1 using at least one monoclonal antibody or antigen-binding fragment thereof; repeating the previous step at a subsequent point in time; and comparing the level of expression of said Gal1 detected in steps a) and b) to monitor the progression of the disease in the subject. In embodiments, the subject has undergone treatment to ameliorate tumor growth between the first point in time and the subsequent point in time.

In some embodiments, the sample comprises cells obtained from a subject. Cells may be in a fluid selected from the group consisting of whole blood, serum, plasma, interstitial fluid, cerebrospinal fluid, lymph fluid, saliva, stool, and urine. In embodiments, the level of Gal1 expression is assessed using a reagent that specifically binds with a Gal1 protein, polypeptide or protein fragment thereof (e.g., an antibody, an antibody derivative, or an antibody fragment). In embodiments, the level of Gal1 expression is assessed by detecting the presence in the sample of a transcribed polynucleotide encoded by a Gal1 polynucleotide (e.g., mRNA or cDNA) or a portion of said transcribed polynucleotide. In embodiments, the step of detecting further comprises amplifying the transcribed polynucleotide. In embodiments, the level of Gal1 expression is assessed by detecting the presence in the sample of a transcribed polynucleotide that anneals with a Gal1 polynucleotide or anneals with a portion of a Gal1 polynucleotide, under stringent hybridization conditions. In embodiments, a significant increase comprises at least a two-fold or at least a five-fold increase between the level of expression of Gal1 in the subject sample relative to the normal level of expression of Gal1 in the sample from the control subject.

Administration of an effective amount of an anti-Gal1 agent to a subject having a cancer (or tumor) refractory to anti-VEGF treatment according to embodiments inhibits or prevents the synthesis of a Gal1 polypeptide. As a result, the antisense oligonucleotide is taken up by cells and hybridizes to a Gal1 mRNA to prevent translation. Alternatively, an oligonucleotide that binds double-stranded DNA to form a triplex construct in order to prevent DNA unwinding and transcription may be used. As a result of either, synthesis of Gal1 polypeptide is blocked. When Gal1 expression is modulated, such modulation preferably occurs by a means other than by knocking out the Gal1 gene.

Embodiments also relate to monitoring the influence of additional agents (e.g., drugs, compounds) on the expression or activity of Gal1 in clinical trials. These and other agents and methods described in further detail in the following sections.

In some embodiments, the administration methods described herein relate to preventing a subject at risk or susceptible to having a cancer refractory to anti-VEGF from becoming afflicted with the cancer. In embodiments, prophylactic methods comprise administering to a subject at risk of or susceptible to having a cancer refractory to anti-VEGF an effective amount of a Gal1 polypeptide or a fragment thereof, or an agent that modulates Gal1 expression or at least one Gal1 activity to thereby modulate angiogenesis.

A modulating agent according to the disclosure may be administered as a "prophylactic agent" to the subject in need of such prophylactic treatment before manifestation of symptoms characteristic of the occurrence of an anti-VEGF cancer or tumor. Exemplary prophylactic agents according to embodiments may include, e.g., antisense Gal1 nucleic acid molecules, anti-Gal1 antibodies, Gal1 inhibitors, nucleic acid molecules encoding Gal1 polypeptides, multivalent forms of Gal1, and compounds that increase the expression of Gal1.

In embodiments, an agent that inhibits Gal1 activity or interactions between a Gal1 polypeptide or a fragment thereof and its natural binding partner(s) or a fragment(s) thereof, can be used prophylactically in vaccines against various polypeptides, e.g., polypeptides derived from pathogens. Immunity against a pathogen, e.g., a virus, can be induced by vaccinating with a viral polypeptide along with an agent that inhibits Gal1 activity or interactions between a Gal1 polypeptide or a fragment thereof and its natural binding partner(s) or a fragment(s) thereof, in an appropriate adjuvant. Alternately, a vector comprising genes that encode for both a pathogenic antigen and a form of Gal1 that blocks interactions between a Gal1 polypeptide or a fragment thereof and its natural binding partner(s) or a fragment(s) thereof can be used for vaccination.

Nucleic acid vaccines may be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al., *J. Biotechnol.* 44:37 (1996)). Alternatively, nucleic acid vaccines can be administered by non-invasive means. For example, pure or lipid-formulated DNA can be delivered to the respiratory system or targeted elsewhere, e.g., Peyers patches by oral delivery of DNA (Schubbert, *Proc. Natl. Acad. Sci. USA* 94:961 (1997)). Attenuated microorganisms can be used for delivery to mucosal surfaces (Sizemore et al., *Science* 270:29 (1995)).

In some embodiments, the antigen in the vaccine is a self-antigen. Such a vaccine is useful in the modulation of tolerance in an organism. Immunization with a self-antigen and an agent that blocks Gal1 activity or interactions between a Gal1 polypeptide or a fragment thereof and its natural binding partner(s) or a fragment(s) thereof can break tolerance (i.e., interfere with tolerance of a self-antigen). Such a vaccine may also include adjuvants such as alum or cytokines (e.g., GM-CSF, IL-12, B7-1, or B7-2).

The various agents administered by the prophylactic, modulating, and treatment methods described herein may be administered conventionally, such as by injection (subcutaneous, intravenous, etc.), oral administration, inhalation, transdermal application, or rectal administration.

The present disclosure also relates to methods for preventing angiogenesis in tumors refractory to anti-VEGF treatments. Embodiments are also based, in part, on the discovery that hypoxia promotes up-regulation of Gal1 resulting in angiogenesis such that targeted disruption of Gal1-glycan lattices attenuates hypoxia-associated angiogenesis, while promoting pericyte maturation and vascular remodeling. Thus, agents such as natural ligands, derivatives of natural ligands, small molecules, RNA, aptamers, peptides, peptidomimetics, glycan-related compounds, glycomimetics, and antibodies that specifically bind to the Gal1 gene or gene products, or fragments thereof, may be utilized in the treatment of cancers and tumors refractory to anti-VEGF treatment. Moreover, agents such as Gal1 gene sequences, Gal1 gene products, anti-Gal1 RNA interference molecules, anti-Gal1 antibodies and fragments thereof (i.e., antibodies that specifically bind to Gal1 gene products or fragments thereof), may be utilized to down-regulate Gal1 and glycan lattice expression.

Methods, and pharmaceutical compositions administered by the methods, relate to detection and/or modulation of expression and/or activity of a Gal1 gene or fragment thereof (e.g., biologically active fragments thereof), as well as to detection and/or modulation of expression and/or activity of gene products or fragments thereof encoded by the Gal1 gene (e.g., biologically active fragments thereof). Embodiments may utilize the Gal1 gene sequence or fragments, as well as the products of the Gal1 gene and/or modulators thereof or fragments thereof, e.g., antibodies which specifically bind to such Gal1 gene products. Embodiments also relate to methods for detecting in a sample the presence, absence, stage, and other characteristics of anti-VEGF refractoriness that are relevant to prevention, diagnosis, characterization, and therapy in a patient. Embodiments also feature compositions of matter, including antibodies (e.g., antibodies that specifically bind to any one or more of the polypeptides described herein) and fusion polypeptides, including all or a fragment of a polypeptide described herein. Moreover, the present disclosure pertains to compositions useful for the reduction of Gal1 nucleic acids (e.g., Gal1 mRNA or hnRNA or fragments thereof), including RNA interference compositions, directed against Gal1 nucleic acids or fragments thereof.

Embodiments are further explained by way of the following examples with reference to experimental results summarized in the Figures.

EXAMPLES

A novel glycosylation-dependent pathway was identified that compensates for the absence of cognate ligand and preserves angiogenesis in response to anti-VEGF treatment. In summary, remodeling of the endothelial cell (EC) surface glycome selectively regulates signaling by Gal1, which, upon recognition of complex N-glycans on the VEGFR2, mimics VEGF-A function. Specifically, vessels within anti-VEGF sensitive tumors exhibited high levels of $\alpha$2-6-linked sialic acid, which prevented Gal1 signaling and angiogenesis. On the other hand, anti-VEGF refractory tumors secrete increased Gal1 and their associated vasculature expresses higher amounts of $\beta$1-6GlcNAc-branched N-glycans and decreased $\alpha$2-6 sialylation, which facilitates Gal1 signaling and revascularization. Interruption of $\beta$1-6GlcNAc branching in ECs or silencing of tumor-derived Gal1 converts anti-VEGF refractory tumors into anti-VEGF-sensitive tumors, whereas elimination of $\alpha$2-6-linked sialic acid confers resistance to anti-VEGF. Disruption of the Gal1-N-glycan axis promotes vascular remodeling, immune cell influx and tumor growth inhibition.

Materials and Methods

A. Reagents 488-labeled Gal1 (488-Gal1) was obtained using DyLight labeling kit (Thermo Scientific) following manufacturer's instructions. Inhibitors of Jak2-STAT3 (AG490; 5 µM), JNK-SAP (SP600125; 20 µM), p38 (SB202190; 10 µM) and O-glycosylation (benzyl-$\alpha$-GalNAc; 2 mM) were from Calbiochem. Inhibitors of Erk1/2 (U0126; 5 µM), PI(3)K-Akt (Ly294002; 2 µM) and NF-YB (BAY1 1-7082; 1 µM), N-glycosylation (swainsonine; 3 µM), lactose or sucrose (30 mM) and Axitinib (30 mg/kg) were from Sigma. PNGase F (25 U/µg protein) was from New England Biolabs. Recombinant cytokines including IL-10 (50 ng/ml), IL-17 (5 ng/ml), TGF-$\beta_1$ (3 ng/ml), IFN-$\gamma$ (50 ng/ml), VEGF-A (20 ng/ml), bFGF (10 ng/ml) were from R&D. Biotinylated lectins, including L-PHA (2 µg/ml), LEL (1 µg/ml), SNA (5 µg/ml), MAL II (10 µg/ml), PNA (10 µg/ml) and HPA (10

µg/ml) were purchased from Vector Labs and incubated in buffer containing 150 mM NaCl, 10 mM HEPES and 1% (w/v) bovine serum albumin (BSA; Sigma). ON-TARGETplus SMART siRNA pools against GnT5, C2GnT1, VEGFR2, NRP-1, VEGF-A and scr were from Dharmacon. Transfections were performed by Lipofectamine-RNAiMAX (Invitrogen) following manufacturer's directions. Recombinant Gal1, Gal3 and Gal8 were produced and purified as described (Barrionuevo et al., 2007; Fernández et al., 2005; Delgado et al., 2010). Secondary Ab used were: Alexa Fluor 488-anti-rat IgG (Vector; 1:500), Texas Red-anti-rat IgG (Vector; 1:400), Alexa Fluor 488-anti-rabbit IgG (Cell Signaling: 1:1000) and Alexa Fluor 555-anti-rabbit IgG (Cell Signaling: 1:1000).

B. Cells

Primary HUVEC were maintained in M-199 medium supplemented with 20% fetal calf serum (FCS), EGF (10 ng/ml), bFGF (10 ng/ml), VEGF-A (20 ng/ml) (all from R&D) and used between passage 2 and 5. HEK-293T cells (CRL-1 1268; ATCC) were maintained in RPMI 1640 medium (Life Technologies) supplemented with 10% FCS. Tumor cell lines including B16-F0 (CRL-6322), Lewis lung carcinoma (LLC1; CRL-1642), R1.1 lymphoma (TIB42) and CT26 colon carcinoma (CRL-2638) and the mouse EC line EOMA (CRL-2586) were obtained from American Type Culture Collection (ATCC). Gal1-specific shRNA was cloned into the pSIREN-RetroQ vector and delivered using the RetroPack PT-67 packaging cell line as described in Croci et al., $J. Exp. Med.$ 209:11, 1985-2000 (2012).

C. Mice

B6.Lgals1$^{-/-}$ mice were provided by F. Poirier, B6.Mgat5$^{-/-}$ mice were provided by J. Dennis, B6.St6 gal$^{-/-}$ mice were provided by J. Paulson, and B6.Rag1$^{-/-}$ mice were from Jackson Laboratories. Mice were bred at the animal facilities of the Institute of Biology and Experimental Medicine (IBYME) according to NIH guidelines. Protocols were approved by the Institutional Review Board.

D. Angiogenesis Assays

The formation of capillary-like tubular structures was assessed in Matrigel-coated plates (essentially as described in Croci and Rabinovich, $J. Exp. Med.$ 209:11, 1985-2000 (2012). In brief, HUVEC ($3\times10^4$) or EOMA cells ($2\times10^4$), transfected or not with specific siRNA or pre-incubated with signaling pathway inhibitors, were seeded on Matrigel with Gal1 (0 to 3 µM) or VEGF-A (20 ng/ml) with or without lactose, sucrose or blocking Ab specific for Gal1 (F8.G7 mAb; 0.5 µM), VEGFR1 (AP-MAB0702; 5 µg/ml) or VEGFR3 (AB89501; 10 µg/ml) from Abcam or Ab specific for VEGF-A (MAB293; 5 µg/ml), VEGFR2 (AF357; 2 µg/ml) or $\alpha_v\beta_3$ (MAB3050; 20 µg/ml), $\alpha_5$ (AF1864; 10 µg/ml) or $\beta_1$ (MAB17781; 10 µg/ml) integrins or isotype control IgG1κ (all from R&D). Cells were incubated at 37° C. for periods ranging from 0 to 24 h and were visualized by phase-contrast microscopy. Capillary-like tubular structures were scored by counting the number of tubules (closed areas) per well in a phase-contrast microscope (Nikon E-100). For migration assays, ECs ($4\times10^4$/well) transfected or not with specific siRNA were resuspended in M199 medium supplemented with 1% FCS. Cells were placed into the top chamber of the insert while the bottom well was filled with Gal1 or VEGF-A in the absence or presence of the above mentioned stimuli. After 24 hours, inserts were stained with crystal violet (Sigma) and analyzed in an inverted microscope. For each filter, 4 images were obtained and cells were counted with ImageJ software v1.46r (NIH). For proliferation assays, ECs were seeded in 96-well microtiter plates ($1\times10^3$ cells/well), pre-incubated for 1 hour at 37° C. with lactose, sucrose, signaling pathway inhibitors or specific blocking Ab and exposed to Gal1. After 24 hours, cells were incubated in the presence of 0.8 µCi [$^3$H]-thymidine (NEN Dupont). Cells were then harvested and radioactivity was measured in a 1414 Liquid Scintillation Counter (Perkin Elmer). Tumor-associated ECs were identified by flow cytometry using Alexa Fluor 647-conjugated anti-CD34 (RAM34; eBioscience) and FITC-conjugated anti-CD45 (J33; Immunotech). Microvessel density (MVD) was determined by counting the number of CD31$^+$ microvessels present in 10 mm$^2$. Ten random 400× fields were counted.

E. Induction of Hypoxia

Tumor cell lines and HUVEC were cultured in p60 dish plates, placed in a modular incubator chamber (Billups-Rothenberg) and flushed at 2 psi for 10 min with a mixture of 1% $O_2$, 5% $CO_2$, and 94% $N_2$. The chamber was sealed and placed in a 37° C. incubator for 18 h. Controls of normoxia were placed in the same incubator at 20% $O_2$.

F. Glycan Nanoprofiling

Cells ($5\times10^6$) were detached, washed in PBS, resuspended in 1 ml milliQ water and lyophilized. Lyophilized cell lysates were then subjected to deglycosylation, glycan purification, derivatization and analysis (according to the methods described in Kalay et al., (2012)). For deglycosylation, 1 mg cell lysate was reconstituted in 100 µl denaturation buffer (2% SDS, 7M urea, 1M β-mercaptoethanol, 2 M thiourea in 0.25 M phosphate buffer, pH 8.5) and incubated with 10 U PNGase F at 37° C. for 12 hours. The released glycans were then isolated using porous graphitic carbon disposable columns for solid phase extraction (Supelco) according to the manufacturer's instructions. Bound oligosaccharides were eluted with 0.4 ml of 25% acetonitrile (ACN) and 0.1% trifluoroacetic acid (TFA). The eluates were lyophilized and re-dissolved in 3 ml milliQ water. Glycan derivatization with the fluorochrome 7-amino-4-methylcoumarin (Sigma) was achieved through reductive amination. Derivatization of glycans on their reducing end was carried out by adding 5 µl of fluorophore, 5 µl of reductant picoline boranem and 5 µl of acetic acid to lyophilized oligosaccharides and incubated for 2 hours at 65° C. Derivatized oligosaccharides were purified by paper chromatography, lyophilized and dissolved in 300 µl 75% ACN. Separation of derivatized oligosaccharides was performed by normal phase HPLC in a Dionex 3000 nanoLC Jasco FP2020 fluorescence detector with a capillary tube flow cell manifold and Thermo Finnigan LCQ decaXP iontrap mass spectrometer. Polymer based analytical (250 mm×75 µm) and trap (10 mm×300 µm) NanoLC columns were packed by Grace Alltech with amide functionalized polymer. Derivatized oligosaccharides were detected using a Waters F2020 fluorescence detector. The fluorescence flow cell was prepared according to the manufacturer's manual. Trap and analytical columns were all connected with 20 µm silica tubing. The 20 µm tubing from which the flow cell was made served also as connection tubing between LC and the MS to avoid dead volumes. Samples were loaded onto the Amide 80 trap column with 100% solvent C (10 mM ammonium formate in 80% ACN with 1% formic acid). After 10 min the column was switched in-line with the analytical column. The mass spectrometer was tuned with 7-amino-4-methylcoumarin (AMC)-labeled maltoheptoase. The capillary temperature and voltage were set at 240° C. and 46 kV, respectively. All measurements were performed in the positive mode and structural assignment was based on MS data for each parental ion.

G. ELISA

Gal1 was determined using an in-house ELISA (according to the methods described in Croci et al., *J. Exp. Med.* 209:11, 1985-2000 (2012). The mouse IFN-γ (DY485), mouse IL-17 (DY421), mouse TGF-$β_1$ (DY1679), mouse Gal3 (DY1179) and human VEGF-A (DY293B) ELISA sets were from R&D. The mouse IL-10 (555252) set was from BD Biosciences, the mouse bFGF (Ab100670) set was from Abcam, and the mouse Gal8 (SEA308Mu) set was from USCN Life Science. Optical densities were determined at 450-550 nm in a Multiskan MS microplate reader (Thermo Electron Corporation).

H. Real-Time Quantitative RT-PCR

SYBR Green PCR Master Mix was used with an ABI PRISM 7500 Sequence Detection Software (all from Applied Biosystems). Primers used were Human RN18S1, Human C2GnT1, and Human GnT5, the sequences of which are provided in U.S. Patent Application Publication No. 2013/0011409 and incorporated by reference herein.

I. Flow Cytometry

For intracellular cytokine staining, TDLN cells were made permeable with Perm2 solution (BD Biosciences) and were labeled with fluorescent-conjugated mAb anti-IFN-γ (XMG1.2; BD Biosciences), anti-IL-17 (TC11-18H10; BD Biosciences), anti-IL-10 (JESS-16E3; eBioscience), anti-CD8 (H35-17.2; eBioscience) and anti-CD4 (GK1.5; BD Biosciences). Cells were analyzed on a FACSCanto II flow cytometer (BD Biosciences). For adoptive transfer, splenic T cells ($5×10^6$) from tumor-bearing mice were labeled with CFSE (Molecular Probes) and injected through the tail vein into tumor-bearing recipient mice treated with F8.G7 mAb or isotype control. APC-fluorescent beads (7-10 μm; BD Biosciences) were injected as controls. $CFSE^+$ cells or $APC^+$ beads were analyzed after 24 h or 15 min respectively by flow cytometry in the tumor parenchyma and spleen.

J. Immunohistochemistry and Confocal Microscopy

Mice were anesthetized and intracardiacally perfused with PBS and 4% (w/v) paraformaldehyde and tissues were embedded in OCT. To visualize the vasculature, mice were intravenously injected with FITC-conjugated *Griffonia simplicifolia* Lectin-1 (GLS-$1_{B4}$; Vector) prior to heart perfusion and fixation. Pericyte maturation was assessed using Ab specific for α-SMA (1A4; Dako), desmin (D33; Dako), PDGFR-β (APB5; Biolegend) and RGS5 (HPA001821; Prestige Sigma). The fraction of pericyte coverage was calculated as the ratio of α-SMA area to the FITC-GLS-$1_{B4}$ or CD31-stained area using a specific anti-CD31 Ab (Mec13.3; BD Biosciences). Hypoxia was detected after injection of pimonidazole hydrochloride for 30 min following immunostaining with Hypoxyprobe-1 plus kit (Natural Pharmacia). Tumor-infiltrating cells were analyzed using anti-CD8 (H35-17.2; e-Bioscience) and anti-F4/80 (BM8; eBioscience) mAb.

K. Fluorescence Spectroscopy Analysis

Association between rhVEGFR2 and Gal1 was studied by a FRET-based fluorescence spectroscopy approach. NHS-activated fluorophores DyLight 488 (DL488, FRET donor) and DyLight 594 (DL594, FRET acceptor) were purchased from Thermo Scientific. For labeling, 4 mg rhGal1 and 100 μg of the recombinant extracellular domain of VEGFR2 expressed in human cells (Sino Biological Inc.) were modified with 200 μg of DL594 and 50 μg of DL488, respectively. Labeling was carried out in PBS buffer in the presence of 5 mM dithiothreitol (DTT) for 1 hour at room temperature following manufacturer's recommended protocol (Thermo Scientific). Labeled rhGal1 was purified by size exclusion chromatography using a Superdex-75 column (GE Life Sciences) generated in PBS containing 5 mM DTT and concentrated up to 200 μM using Centricon tubes (Millipore). Labeled VEGFR2 was dialyzed for 48 hours against PBS using a homemade microdialyzer. Fluorescence spectra were measured in a JASCO FP-6500 spectrofluorometer endowed with a Peltier effect thermostatized cell holder. A 4×4 mm fluorescence cell was employed. All binding assays were carried out at 25° C. in PBS buffer with the addition of 5 mM DTT. Excitation wavelength was set to 493 nm, with a bandpass of 1 nm. Emission spectra were recorded from 500 to 680 nm, using a bandpass of 3 nm. Binding assays were carried out by adding aliquots of Gal1-DyLight 594 to 400 μL of 0.5 μM VEGFR2-DyLight 488. After each addition, samples were incubated for 10 min to ensure equilibrium conditions before spectra acquisition. Fluorescence intensity at 518 nm was corrected for dilution and inner filter effects. The VEGFR2:Gal1 complex was titrated with a lactose solution in PBS supplemented with 5 mM DTT to ensure the specificity of the effect.

L. Glycophenotypic Analysis and Glycan Nanoprofiling

Cells were incubated with biotinylated L-PHA, LEL, SNA, MAL II, PNA and HPA (all from Vector) (according to methods described in Toscano et al. (2007)). Glycan nanoprofiling was performed following the deglycosylation, glycan purification and derivatization, as described above.

M. Galectin Binding, Receptor Segregation, and Endocytosis

For Gal1 binding, ECs were incubated for 1 hour at 4° C. with DyLight 488-labeled Gal1 following transfection with MGAT5, C2GNT1 or scr siRNA, or in the presence or absence of lactose, sucrose or an anti-Gal1 (F8.G7) mAb generated and characterized as described (see Ouyang et al. (2011), and Croci et al., *J. Exp. Med.* 209:11, 1985-2000 (2012)). To analyze receptor retention, HUVEC transfected or not with MGAT5 siRNA were incubated with or without Gal1 (1 μM) or VEGF-A (20 ng/ml) and stained with anti-VEGFR2 Ab (AF357; R&D). Cells were analyzed in a FACSCanto II flow cytometer (BD Biosciences). For segregation assays, ECs were treated with Gal1 (1 μM), fixed and incubated with anti-VEGFR2 Ab (55B11; Cell Signaling). For endocytosis, ECs transfected or not with MGAT5 siRNA were incubated with or without Gal1 (1 μM) and/or VEGF-A (20 ng/ml), permeabilized and incubated with anti-VEGFR2 Ab (55B11; Cell Signaling) and anti-early endosomal antigen 1 (EEA1; Sigma). Cells were analyzed on a Nikon laser confocal microscope (Eclipse E800).

N. Phospho-RTK Signaling Array, Co-Immunoprecipitation & Immunoblotting

Cells were lysed and analyzed by the human PATHSCAN RTK Signaling Antibody Array (Cell Signaling) following the manufacturer's directions. For co-immunoprecipitation, 500 μg lysates were incubated with 2 μg anti-VEGFR2 (55B11; Cell Signaling) Ab. The immunocomplexes were captured with protein G PLUS-Agarose (Santa Cruz) and processed for immunoblotting (according to methods described in Ilarregui et al., *Nat. Immunol.* 10, 981-99 (2009)). Blots were probed with anti-Erk1/2 (C14), anti-phospho-Erk1/2 (E4), anti-actin (I-19), anti-Gal3 (B2C10), anti-Gal4 (Q20), anti-Gal7 (H8) or anti-Gal8 (D18) Ab (all from Santa Cruz) or anti-Akt (9272), anti-phospho-Akt (9271 S), anti-VEGFR2 (55B11), anti-phospho-VEGFR2 (19A10) Ab (all from Cell Signaling) or a rabbit anti-Gal1 polyclonal IgG (1.5 μg/ml) (as described in Rubinstein et al., *Cancer Cell* 5:3, 241-51 (2004)).

O. Site-Directed Mutagenesis & Mutant Binding Assays

Seven different constructs were designed by site-directed mutagenesis targeting putative N-glycosylation sites in each Ig-like domain of VEGFR2 (KDR-HA-Ig-1: N46Q, N65Q, N96Q; KDR-HA-Ig-2: N143Q, N156Q; KDR-HA-Ig-3: N245Q, N318Q; KDR-HA-Ig-4: N374Q, N395Q; KDR-HA-Ig-5: N511Q, N523Q; KDR-HA-Ig-6: N580Q, N613Q, N619Q, N631Q; KDR-HA-Ig-7: N675Q, N704Q, N721Q). A full-length KDR construct was used as the control (KDR-HA-WT). The cDNAs were subcloned into pcDNA3.1 (Life Technologies) and HA-tagged constructs were transfected into HEK 293T cells using FuGene HD (Promega). For bead-based immunoprecipitation anti-HA Ab (26183; Thermo Scientific) was conjugated to 7.5 μm APC-fluorescent beads (E9, BD Bioscience) following the manufacturer's directions. Protein lysates from KDR-HA-transfected HEK 293T cells were incubated with 8 μl anti-HA Ab-conjugated beads for 2 hours. Beads were washed, centrifuged for 3 min at 900×g and incubated with Gal1 and Alexa Fluor-488-labeled anti-Gal1 Ab. Mean fluorescence intensity (MFI) in the 488 channel was calculated within the FSC vs SSC gate corresponding to APC$^+$ beads. Relative mean fluorescence intensity (rMFI) of double positive events was compared to non-transfected HEK 293T cells.

P. In Vivo Tumor Models

Wild-type or Gal1 knockdown B16-F0, LLC1 and R1.1 (2.5 or 5×10$^5$ cells) were subcutaneously inoculated into 6- to 8-week old WT, Mgat5$^{-/-}$, St6gal1$^{-/-}$ or Rag1$^{-/-}$ B6 mice. CT26 (5×10$^5$) cells were injected into syngeneic BALB/c mice. When tumors reached 100 mm$^3$, mice were inoculated intraperitoneally with anti-VEGF (B20-4.1.1; 5 or 10 mg/kg), anti-Gal1 (F8.G7; 5, 10 or 15 mg/kg) or isotype control mAb twice weekly. Axitinib (30 mg/kg; Sigma) was administered every two days by oral gavage. Mice were sacrificed when tumors reached a volume greater than 2.5 cm$^3$. Two weeks after tumor inoculation, TDLN cells (5×10$^5$/well) were re-stimulated ex vivo for 72 hours with lysates of B16-F0 or LLC1 cells and analyzed for proliferation and cytokine production (as described in Rubinstein et al., Cancer Cell 5:3, 241-51 (2004)).

Q. Statistical Analysis

Prism software (GraphPad) was used for statistical analysis. Two groups were compared with the Student's t-test for unpaired data. Two-way ANOVA and Dunnett's or Tukey post-tests were used for multiple comparisons. P values of 0.05 or less were considered significant.

Findings

A. Context-Dependent Regulation of EC Surface Glycosylation Controls Gal1 Binding and Angiogenesis To investigate the contribution of the EC surface glycome to sprouting angiogenesis, the "glycosylation signature" was examined of human ECs at baseline and following exposure to physiologically relevant stimuli. For this purpose, a panel of lectins was used that recognize specific glycan structures, including those that are relevant for Gal1 binding and signaling. Gal1 recognizes multiple galactose-β1-4-N-acetylglucosamine (LacNAc) units, which may be present on the branches of N- or O-linked glycans. Thus, regulated expression of glycosyltransferases that create poly-LacNAc ligands may determine susceptibility to Gal1 binding. This includes the N-acetylglucosaminyltransferase 5 (MGAT5), an enzyme that generates β1-6-N-acetylglucosamine (β1-6GlcNAc)-branched complex N-glycans, which are the preferred intermediates for poly-LacNAc extension (FIG. 1A, upper panel).

Figure 1B:
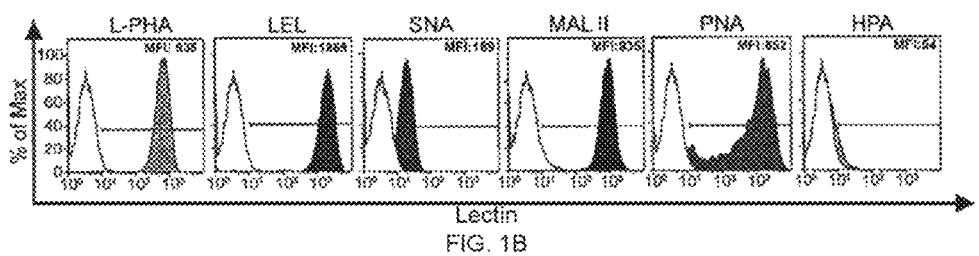

Under resting conditions, considerable expression of L-phytohemagglutinin (L-PHA)-reactive GnT5-modified N-glycans (FIG. 1A) was shown by primary human vein umbilical ECs (HUVEC), and increased significantly following exposure to immunoregulatory cytokines (IL-10 or TGF-β$_1$) or to proliferative stimuli such as basic fibroblast growth factor (bFGF) (FIG. 1B). In contrast, a significant reduction of L-PHA-reactive glycol-epitopes was shown by ECs exposed to pro-inflammatory T$_H$1-type (IFN-γ) or T$_H$17-type (IL-17) cytokines (FIG. 1B). A substantial increase in reactive glyco-epitopes following exposure to immunosuppressive or proliferative stimuli was revealed by staining with the Lycopersicon esculentum lectin (LEL), which recognizes poly-LacNAc ligands (FIGS. 1A and 1B).

As α2-6 sialyltransferase (ST6Gal1) may modify LacNAc ligands and block Gal1 signaling (Toscano et al., Nat. Immunol. (2007)), binding of Sambucus nigra agglutinin (SNA), a lectin that recognizes α2-6-linked sialic acid (SA) sequences, was examined. A decrease in SNA-reactive glyco-epitopes, as compared to resting IL-17- or IFN-γ-treated ECs, was displayed by ECs stimulated with bFGF or a combination of IL-10 and TGF-β$_1$ had (FIGS. 1A and 1B), suggesting that pro- or anti-inflammatory signals may either mask or unmask Gal$_1$-specific binding sites. In contrast, similar binding profiles for the Maackia amurensis agglutinin (MAL II), which recognizes α2-3 SA linkages, were shown by human ECs regardless of the stimulus used (FIGS. 1A and 1B); these results suggest that changes in glycosylation are specific and do not represent a global loss of SA from cell surface glycoproteins.

Exposure of Gal1-specific glyco-epitopes may also be regulated by the α2-3 sialyltransferase 1 (ST3GAL1), which competes with the core-2 β1-6-N-acetylglucosaminyltransferases (C2GNTs) for core-1 O-glycan structures and may inhibit the addition of O-linked poly-LacNAc ligands (FIG. 1A, upper panel). To assess the influence of this pathway, the EC surface glyco-receptors were probed for the absence of sialylated core-1 O-glycans using the lectin peanut agglutinin (PNA), which binds to asialo-galactose-β1-3-N-acetyl-galactosamine core-1 O-glycans. Notably, a modest but significant increase in PNA-reactive asialo-core-1 O-glycans, compared to cells exposed to pro-inflammatory T$_H$1 or T$_H$17 cytokines, was observed upon exposure of human ECs to bFGF, IL-10 or TGF-β$_1$ (FIGS. 1A and 1B). Finally, no significant binding of Helix pomatia agglutinin (HPA), a lectin that recognizes terminal α-N-acetyl-galactosamine residues, was observed (FIG. 1A). In most cases, stimulation with both IL-10 and TGF-β$_1$ had additive effects (FIG. 1B). Moreover, no significant changes in the EC glycan profile were observed upon exposure to VEGF-A (FIG. 1B). Similar results were observed using the mouse EC line EOMA (data not shown). Overall, these findings demonstrate that immunosuppressive and proliferative stimuli appear to favor a "Gal1 permissive" glycophenotype on ECs, while pro-inflammatory signals tend to interrupt exposure of these glyco-epitopes.

Figure 1C:
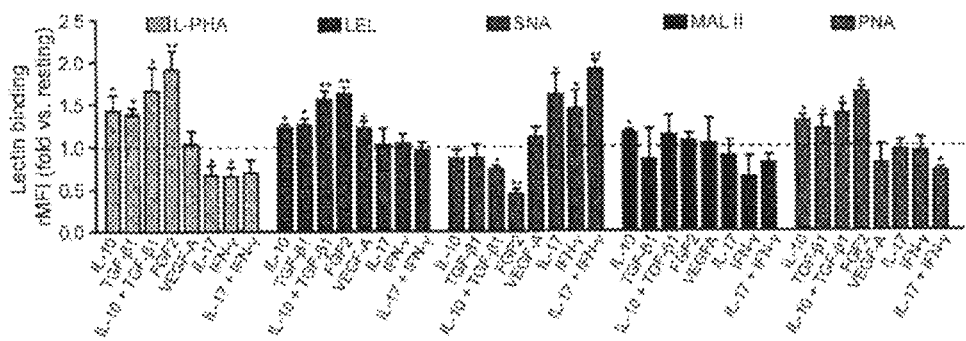
Figures 1D, 1E, 1F:
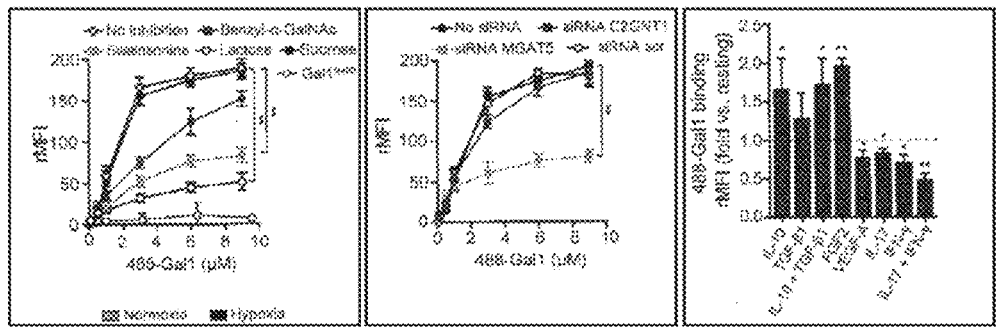

To determine the contribution of EC surface glycosylation to Gal1 signaling, Gal1 binding to ECs under different experimental conditions was examined. Dose- and carbohydrate-dependent binding of Gal1 to ECs was observed (FIG. 1C). Accordingly, no binding of a Gal1 mutant lacking carbohydrate-binding activity (Gal1$^{N46D}$) (Voss et al., (2008)) to ECs was observed at any of the concentrations tested (FIG. 1C). While Gal1 binding was almost completely abrogated by swainsonine, an inhibitor of N-glycan biosynthesis, benzyl-α-GalNAc, a metabolic competitor of O-glycan elongation, was only partially inhibitory (FIG. 1C), suggesting the essential contribution of N-glycans to Gal1 signaling. Moreover, Gal1 binding to the surface of ECs was almost completely eliminated by interruption of complex-type N-glycan branching through short interfering RNA (siRNA)-mediated silencing of MGAT5. No effect was observed due to inhibition of a core 2 O-glycan elongation through siRNA-mediated C2GNT1 silencing (FIG. 1D), demonstrating both the saccharide dependence and specificity of this effect. Consistent with changes in glycosylation, much higher binding of Gal1 was observed in ECs exposed to immunosuppressive stimuli compared to cells sensing pro-inflammatory cytokine signals (FIG. 1E). Thus, complex N-glycans may influence vascular biology through the establishment of lectin-glycan interactions which are facilitated in immunosuppressive and proliferative microenvironments.

Because hypoxia is a hallmark of tumor progression and a potential determinant of resistance to anti-angiogenic therapies (see, e.g., Bergers and Hanahan, *Nat. Rev. Cancer* 8:8, 592-603 (2008)), a study was undertaken to evaluate the influence of exposure to hypoxic microenvironments on the EC glycan profile. In comparison to normoxia, β1-6GlcNAc-branched N-glycans (L-PHA reactivity) and poly-LacNAc structures (LEL reactivity) were increased by, α2-6-linked SA (SNA binding) were decreased by, and asialo-core-1 O-glycans (PNA binding) were slightly changed by hypoxia (1% $O_2$) (FIG. 1F). These results were substantiated by glycan nanoprofiling, in which a dramatic decrease in the amount of sialylated N-glycans on ECs exposed to hypoxia was documented (FIG. 1G).

Figure 1G:
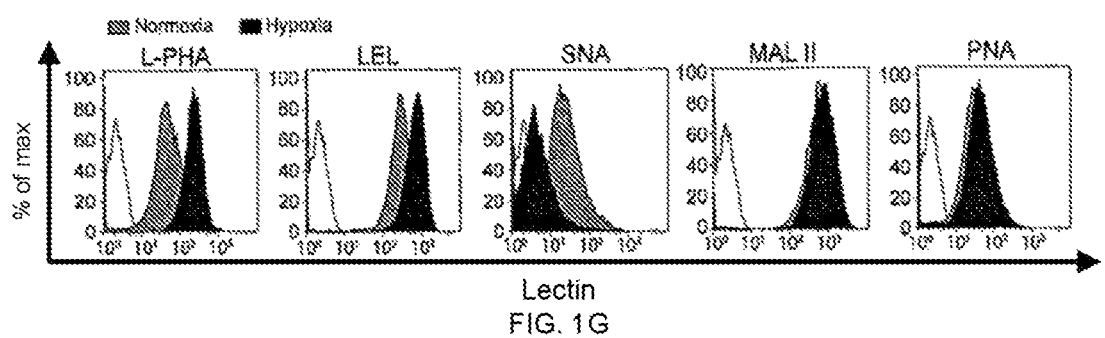
Figure 1H:
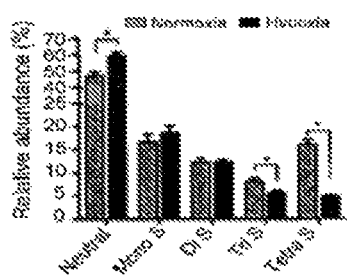

The relative abundance of neutral N-glycans was indicated by quantitative analysis, while a considerable decrease in the amounts of tri- and tetra-sialylated N-glycans was observed on ECs subjected to hypoxia (FIG. 1G). These data indicate extensive and selective remodeling of the EC surface glycome in hypoxic microenvironments, similar to that found in response to immunosuppressive stimuli, which results in increased availability of cell surface glycans for Gal1 binding. Accordingly, preferential binding of Gal1 to ECs exposed to hypoxia was found, as compared to those cultured under normoxic conditions (FIG. 1H).

Figure 1I:
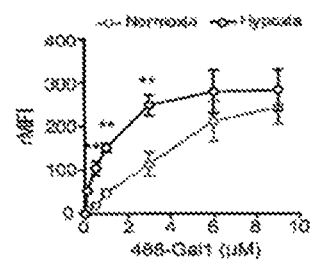
Figure 1J:
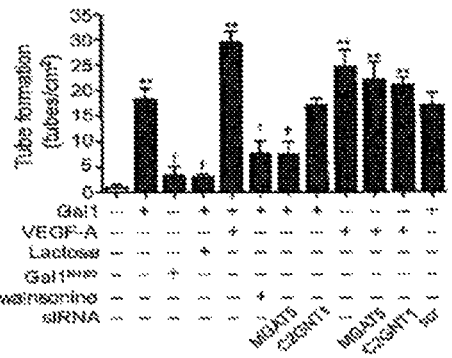

Further, the selective contribution of N- and O-glycans to the proangiogenic functions displayed by Gal1 and VEGF-A was analyzed. EC proliferation, migration and tube formation induced by Gal1 was almost completely prevented by addition of lactose or interruption of complex N-glycan branching through siRNA-mediated MGAT5 silencing or incubation with swainsonine, while no effect was observed from silencing C2GNT1 (FIG. 1I). Supporting these findings, no impact on EC response was observed upon exposure to Gal1$^{N46D}$ mutant (FIG. 1I). In contrast, the pro-angiogenic effects of VEGF-A were preserved regardless of the absence or presence of complex N- or O-glycan branching (FIG. 1I). Thus, unlike VEGF-A, Gal1 delivers pro-angiogenic signals to ECs through a glycosylation-dependent pathway involving context-dependent remodeling of complex N-glycans.

B. Glycosylation-Dependent Binding of Gal1 to ECs Mimics VEGF Signaling

Screening for changes in the phosphorylation status of a spectrum of growth factor RTKs and signaling nodes revealed that VEGFR2 was the only tested RTK that became phosphorylated following treatment of human ECs with Gal1 (FIG. 2A). This phosphorylation pattern was detected after as early as 15 min after exposure (FIG. 2A) and was sustained even after 60 min of exposure to this lectin (data not shown). In addition, phosphorylation of Akt (Thr$^{308}$), Akt (Ser$^{473}$) and the mitogen-activated protein kinase Erk1/2 increased upon Gal1 exposure, recapitulating the phosphorylation pattern elicited by VEGF-A (FIG. 2A). Akt and Erk1/2 phosphorylation induced by either Gal1 or VEGF-A were almost completely prevented by silencing VEGFR2 (FIG. 2B), and Gal1-induced EC migration and tube formation were abrogated by silencing VEGFR2 (FIGS. 2C and 2D). In contrast, no effect on Gal1-induced EC functions was observed by blockade of VEGFR1, VEGFR3 or integrins $α_vβ_3$ or $α_5β_1$ (FIG. 2D), suggesting that, in spite of their glycosylation status, only selected EC receptors function as Gal1 targets.

Additionally, no significant impact on Gal1 function was observed due to siRNA-mediated silencing of NRP-1 (FIG. 2C), in spite of its ability to interact with this lectin (Hsieh et al., *Oncogene* 27, 3746-3753 (2008)). While EC migration induced by Gal1 or VEGF-A was abrogated by inhibition of VEGFR2 signaling, VEGF-A effects were only suppressed by NRP-1 silencing. Because of the autocrine effects of VEGF signaling (Lee et al., *Cell* 130, 691-703 (2007)), it was next examined whether Gal1 signaling proceeded in the absence of VEGF-A. Consistent with lack of impact of Gal1 on VEGF-A secretion, no influence on Gal1-induced EC migration and tube formation was observed by inhibition of both intracellular and extracellular VEGF-A through siRNA-mediated silencing or Ab-mediated blockade (FIGS. 2C and 2D). Similarly, no impact on Gal1 function was observed due to blockade of bFGF.

As branching of complex N-glycans attached to growth factor receptors may fine-tune the threshold for growth factor signaling (Lau et al., *Cell* 129, 123-134 (2007); Song et al., *Cancer Res.* 70, 3361-3371 (2010)), whether MGAT5-modified glycans can directly modulate sensitivity of VEGFR2 to its canonical ligand, VEGF-A, was further investigated. Gal1 responsiveness was selectively eliminated by inhibition of MGAT5-mediated N-glycan branching; however, no impact was observed on VEGF signaling (FIG. 2B). In contrast, no substantial effect was observed on Gal1 or VEGF-A signaling due to blockade of core-2 O-glycan elongation via knock-down of C2GNT1. Therefore, rather than altering VEGF-A signaling, it was found that Gal1 may directly co-opt the VEGFR2 pathway through binding to LacNAc-enriched complex N-glycan structures. To determine whether Gal1 establishes direct interactions with VEGFR2 through N-glycosylation-dependent mechanisms, co-immunoprecipitation experiments were performed with lysates of human ECs treated with Gal1 in the absence or presence of PNGase F, an endoglycosidase that releases N-linked oligosaccharides, or following transfection with MGAT5 or C2GNT1 siRNA. Specific association of Gal1 with VEGFR2 was observed through interactions that depended on early or late stages of N-glycan elongation (FIG. 2E). To characterize further these interactions, binding of Gal1 to fully-glycosylated recombinant human VEGFR2 (rhVEGFR2) by fluorescence resonance energy transfer (FRET) was analyzed. A drop of fluorescence intensity of 488-labeled rhVEGFR2 was induced by the addition of 594-labeled Gal1, indicating a FRET phenomenon due to molecular association. Bimodal behavior was shown by this complex interaction, in which a slow evolving phase was followed by a rapid changing phase until signal saturation was reached, revealing a dissociation constant ($K_d$) within the low micromolar range (FIG. 2F, left panel). The glycan dependence of these interactions was confirmed by titration of the Gal1-VEGFR2 complex with lactose, showing a considerable increase of 488-VEGFR2 fluorescence, in which a hyperbolic behavior was displayed and an apparent $K_d$ of 250 μM (FIG. 2F, right panel) revealed similar to the $K_d$ of the Gal1-lactose complex (López-Lucendo et al., *J. Mol. Biol.* 343, 957-970 (2004)).

VEGFR2 is equipped with an approximately 750-amino-acid-residue extracellular domain, which is organized into seven immunoglobulin (Ig)-like folds and contains 18 putative N-linked glycosylation sites. While Ig domains 2 and 3 mediate VEGF-A binding, Ig-4 to -6 are involved in receptor dimerization and Ig-7 stabilizes dimer formation (Olsson et al., *Nat. Rev. Mol. Cell Biol.* 7, 359-371 (2006)). To identify which domain(s) are responsible for Gal1 binding, human VEGFR2 mutants were prepared that are devoid of N-glycosylation sites in each of the seven Ig-like domains. The wild-type (WT) and each of the seven HA-tagged VEGFR2 mutants were stably expressed in HEK-293T cells, showing similar expression levels and comparable cell surface expression. To identify specific Gal1-binding sites, mutant and WT transfectants were immunoprecipitated using anti-HA fluorescent beads, and binding of Gal1 to allophycocyanin (APC)-positive immunoprecipitates was examined.

Figure 2I:
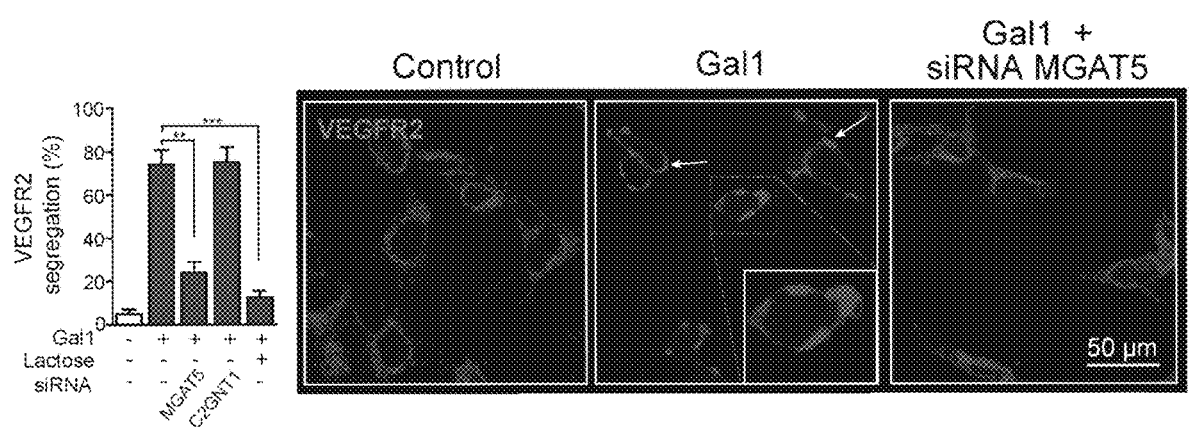
Figure 2J:
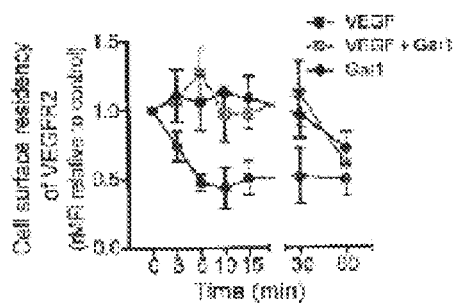

Flow cytometry of double positive beads revealed that mutations in N-glycosylation sites of Ig-3 (N245Q, N318Q), Ig-4 (N374Q, N395Q) and Ig-7 (N675Q, N704Q, N721Q) partially prevented Gal1 binding (FIG. 2G), suggesting major contributions of these domains to glycan-dependent recognition of this endogenous lectin. Moreover, segregation of VEGFR2 to membrane patches was caused by Gal1 binding, indicating rearrangement of signaling clusters on the surface of ECs (FIG. 2H). Accompaniment of segregation with N-glycan-dependent cell surface retention (FIG. 2I) and diminished internalization (FIG. 2J) of VEGFR2, either in the presence or absence of VEGF-A, was observed. Thus, Gal1 mimics VEGF-A signaling through binding to complex N-glycans on VEGFR2 Ig domains 3, 4 and 7.

Figure 3A:
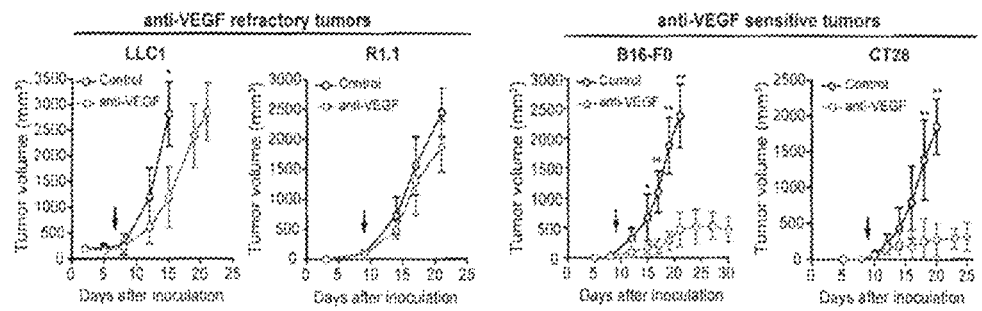
FIGS. 3A-3F show the relationship between differential EC glycosylation and refractoriness to anti-VEGF therapy.
Figure 3B:
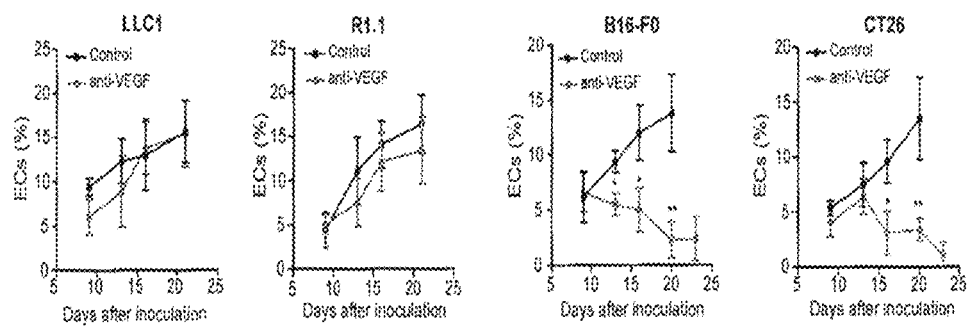

C. Differential Glycosylation of Tumor-Associated Vasculature Defines Resistance to Anti-VEGF Therapy In vitro and in vivo experiments were conducted to evaluate changes in the "glycosylation signature" of ECs associated with well-established tumors that are known to be sensitive (B16-F0 melanoma and CT26 colon carcinoma) or refractory (LLC1 Lewis lung carcinoma and R1.1 T-cell lymphoma) to anti-VEGF therapy (Shojaei et al., *Nat. Biotechnol.* 25, 911-920 (2007)). Confirming these contrasting responses, a marked inhibition of tumor growth when B16-F0 and CT26 sensitive tumors were implanted into syngeneic mice and treated with the anti-VEGF (B20-4.1.1) mAb was found, whereas growth of LLC1 and R1.1 refractory tumors was only transiently and poorly inhibited (FIG. 3A). Refractoriness was associated with the development of a neovascular supply in anti-VEGF resistant versus sensitive tumors (FIG. 3B).

Figure 3C:
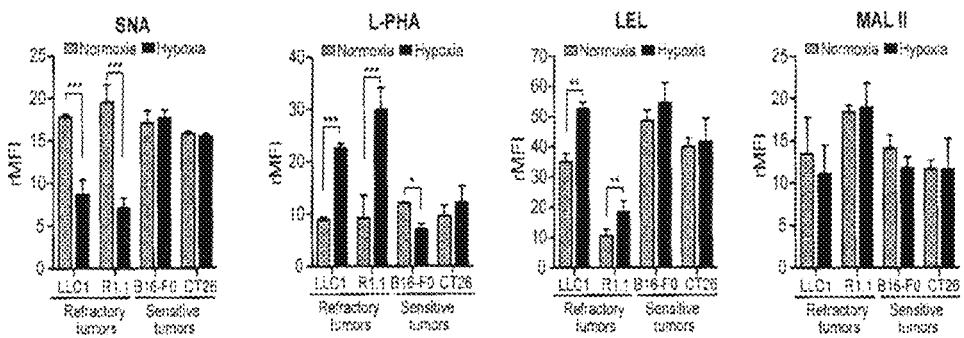
Figure 8A:
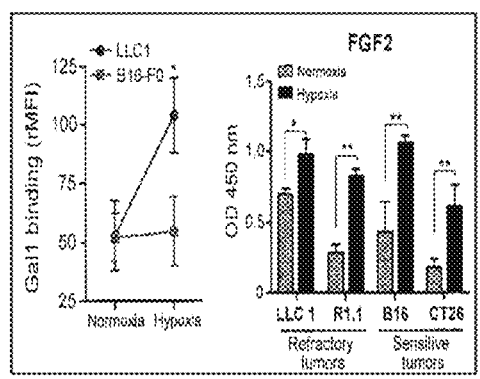
FIGS. 8A-8C show that differential EC glycosylation defines tumor refractoriness to anti-VEGF therapy.

To examine the influence of tumor cells in the 'glycosylation signature' of ECs in vitro, conditioned media from the aforementioned tumors that were previously exposed to normoxic or hypoxic conditions were collected, and changes in the EC surface glycol-profile were analyzed. Notably, consistent changes in the glycan repertoire of ECs characterized by diminished display of SNA-reactive α2-6-linked SA, greater exposure of L-PHA-reactive β1-6-branched N-glycans and increased frequency of LEL-reactive poly-LacNAc-substituted oligosaccharides were induced by conditioned media from anti-VEGF refractory tumors that were previously exposed to hypoxic microenvironments induced, compared to ECs treated with conditioned medium from tumors cultured under normoxic conditions (FIG. 3C). Induction of a "Gal1-permissive" glycan repertoire was a feature of anti-VEGF refractory but not sensitive tumors, which were unable to promote changes in EC surface glycosylation when exposed to hypoxic microenvironments (FIG. 3C). This differential response could not be attributed to selective up-regulation of common pro-angiogenic factors that could influence glycosylation (bFGF, TGF-$\beta_1$ or VEGF-A) in refractory versus sensitive tumors (FIG. 8A). These results suggest that hypoxia may act as a major driving force that instructs anti-VEGF refractory but not sensitive tumors to selectively regulate the EC surface glycoprofile.

Figure 3D:
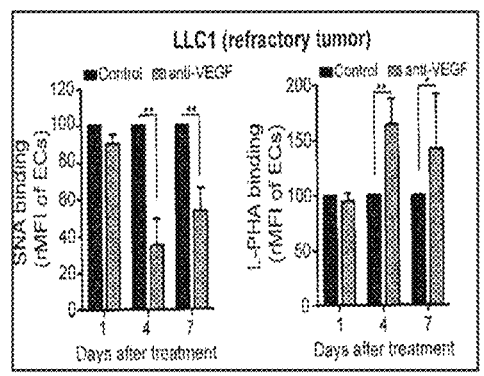
Figure 3E:
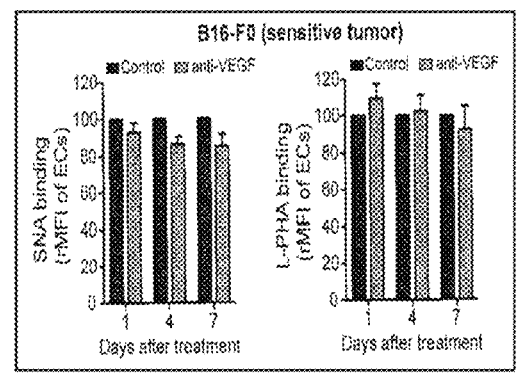
Figure 3F:
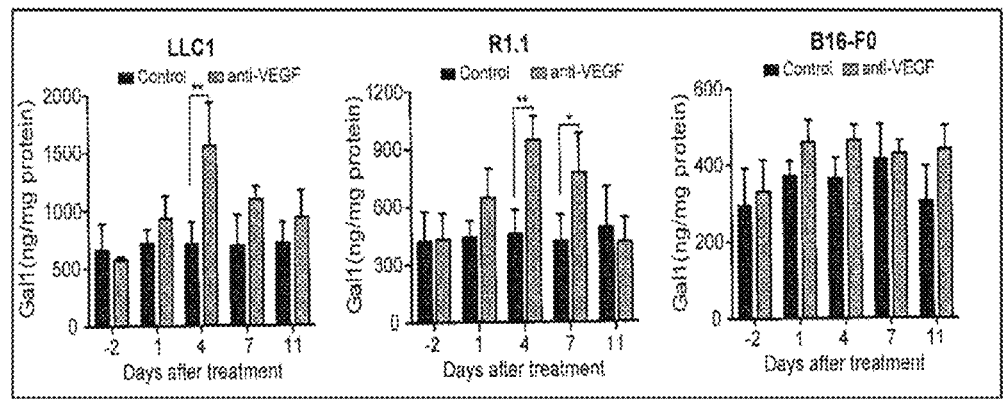
Figure 8B:
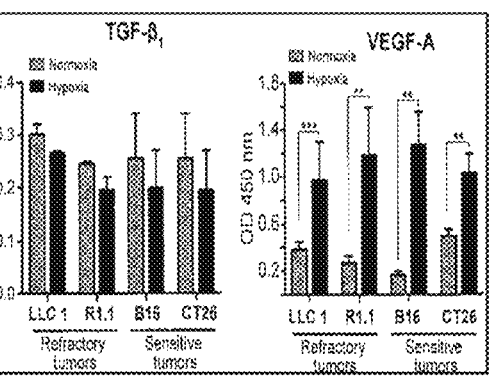
Figure 8C:
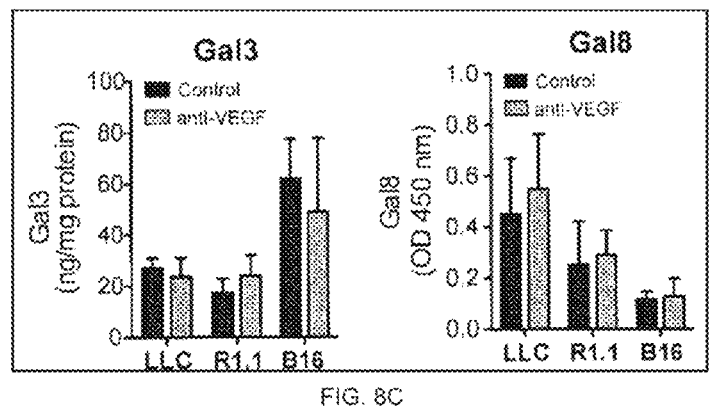
Figure 9A:
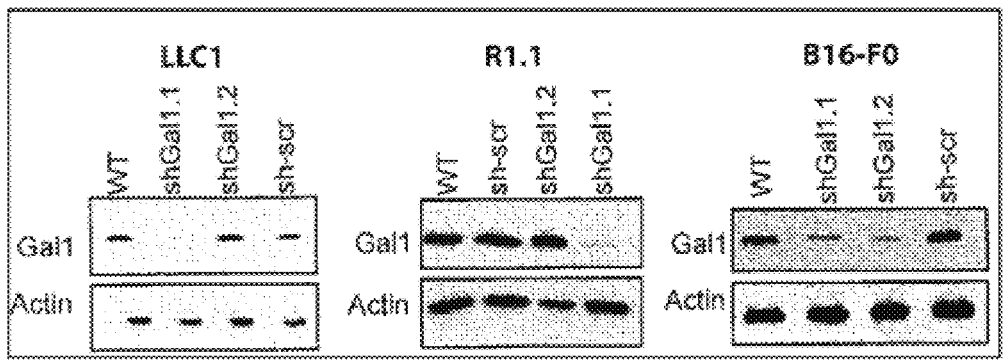
FIGS. 9A-9D show tumors devoid of Gal1 circumventing refractoriness to anti-VEGF therapy.
Figure 9B:
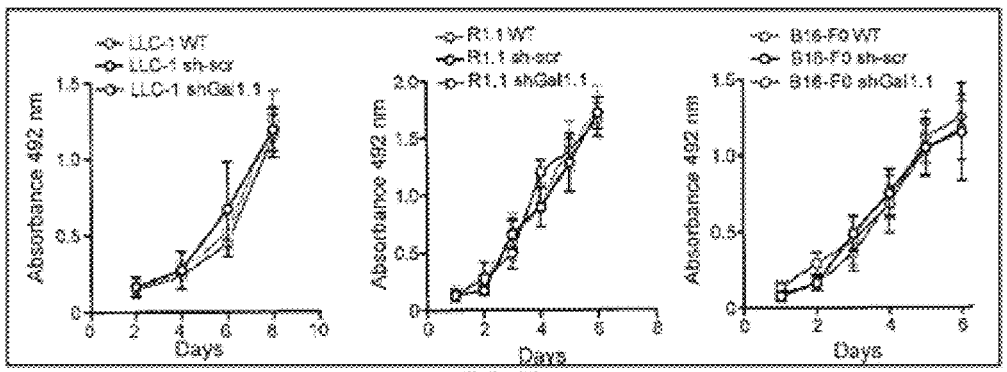
Figure 9C:
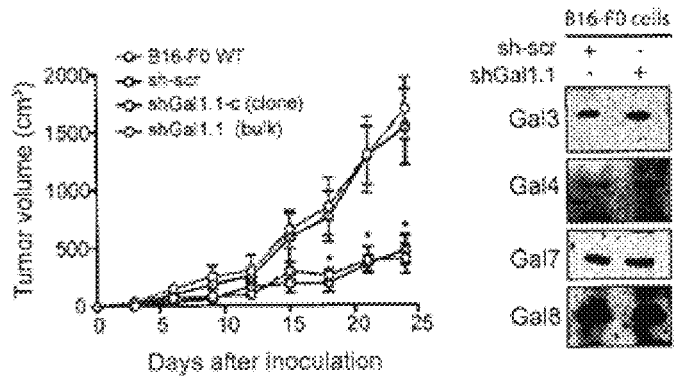
Figure 9D:
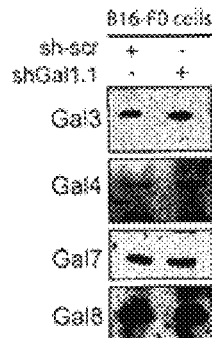
Figure 10A:
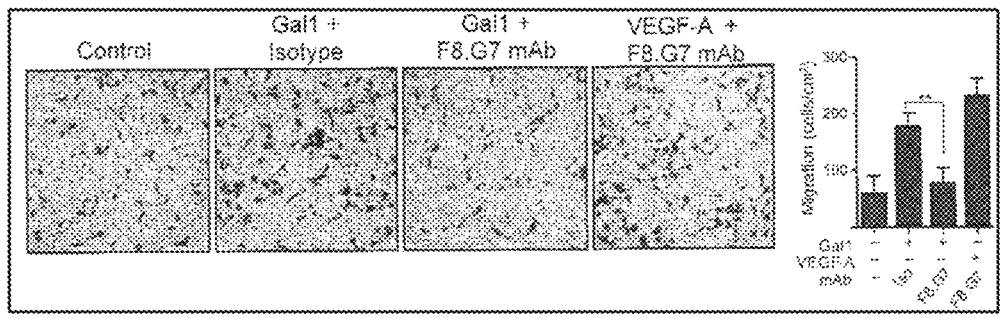
FIGS. 10A and 10B show that targeting the Gal1-N-glycan axis promotes vascular remodeling and overcomes refractoriness to anti-VEGF therapy.
Figure 10B:
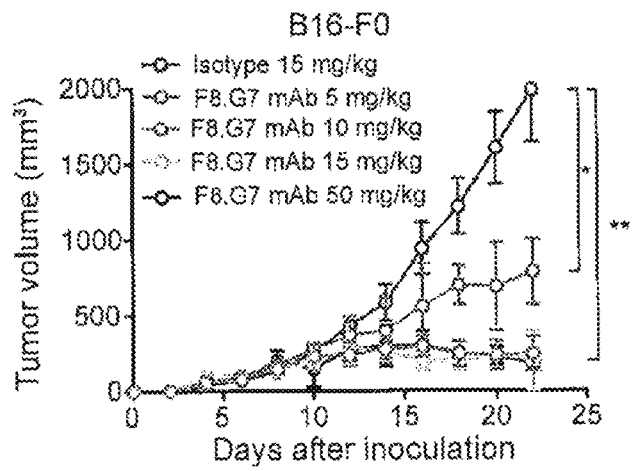

To evaluate changes in the "glycosylation signature" of the tumor-associated vasculature in vivo, mice were implanted with sensitive (B16-F0 and CT26) or refractory (LLC1 and R1.1) tumors and treated with anti-VEGF or control isotype mAb when tumors reached 100 mm$^3$. Glycan profiles were analyzed by lectin cytometry in tumor-associated ECs from each individual tumor (FIGS. 3D and 3E). Four days after anti-VEGF treatment, concurrent with the peak of hypoxia, reduced α2-6 sialylation and higher amounts of β1-6-branched complex N-glycans were displayed by vessels from LLC1 and R1.1 refractory tumors (FIG. 3D). Refractoriness was associated with higher secretion of Gal1, but not other pro-angiogenic galectins (FIGS. 3F and 8B). In contrast, no significant alterations of the EC glycophenotype and no changes in Gal1 secretion in response to anti-VEGF treatment by vessels from B16-F0 and CT26 sensitive tumors were observed (FIGS. 3E and 3F). Thus, anti-VEGF refractory tumors appeared to selectively respond to VEGF blockade by evoking an angiogenic compensatory program that facilitates establishment of Gal1-N-glycan interactions.

D. Tumors Devoid of Gal1 Circumvent Refractoriness to Anti-VEGF Therapy

Syngeneic mice were implanted with LLC1 or R1.1 tumors expressing shRNA-Gal1 constructs and treated with anti-VEGF mAb when tumors reached 100 mm$^3$. Refractoriness to anti-VEGF treatment was decreased by silencing Gal1 in both LLC1 and R1.1 tumors, as evidenced by diminished tumor burden following injection of anti-VEGF mAb (FIGS. 4A and 4B). This effect was not due to intrinsic differences in proliferation rates, as no growth advantage was shown by control LLC1 and R1.1 cells in vitro over Gal1 knockdown tumors (FIG. 4C). Remarkably, a substantial decrease in the percentage of tumor-associated ECs was involved in tumor growth inhibition (FIG. 4B).

This effect was not further enhanced when Gal1 knockdown LLC1 cells were inoculated into syngeneic Gal1-deficient (Lgals1$^{-/-}$) mice (FIG. 4C), suggesting no substantial contribution of host-derived Gal1 to this effect. On the other hand, only a slight, improvement of the therapeutic benefits were induced by targeting Gal1 in anti-VEGF sensitive B16-F0 tumors (FIGS. 4D, 4E and 4C). These effects were not due to undesired "off-target" effects as only Gal1 but not other relevant tumor galectins (Gal3, Gal4, Gal7, Gal8) were altered following shRNA transduction (FIGS. 4A and 4D).

E. Reprogramming of EC Glycosylation Converts Anti-VEGF "Refractory" Tumors to "Sensitive" Tumors To investigate the relevance of EC glycosylation in anti-VEGF compensatory programs, "loss-of-function" experiments were conducted by implanting anti-VEGF refractory or sensitive tumors into glycosyltransferase-deficient mice. Because of the selective up-regulation of β1-6GlcNAc-branched complex N-glycans in vessels associated with anti-VEGF refractory tumors (FIG. 3D), elucidation of the contribution of the N-glycan branching pathway to the compensatory angiogenic phenotype was sought. Mice lacking MGAT5 (Mgat5$^{-/-}$) were implanted with the LLC1 refractory tumor and treated with anti-VEGF or control mAb when tumors reached 100 mm$^3$. The absence of L-PHA-reactive β1-6GlcNAc-branched oligosaccharides in tumor-associated ECs from Mgat5$^{-/-}$ mice was confirmed by flow cytometry analysis (FIG. 5A). Marked inhibition of tumor growth (FIG. 5B) and greatly reduced vascularization (FIG. 5C) were caused by anti-VEGF treatment of Mgat5$^{-/-}$ mice, compared to anti-VEGF-treated WT mice. Thus, otherwise refractory tumors were converted into anti-VEGF-sensitive tumors by the lack of β1-6GlcNAc-branched complex N-glycans in tumor-associated vasculature.

Because α2-6-linked SA was found to be highly represented in the vasculature of anti-VEGF sensitive tumors, it was hypothesized that lack of α2-6 sialylation may render tumors resistant to anti-VEGF treatment. Therefore, mice lacking ST6GAL1 (St6gal1$^{-/-}$) were implanted with the B16-F0 sensitive tumor and treated with anti-VEGF or control mAb when tumors reached 100 mm$^3$. The absence of α2-6-linked SA in ECs from tumor-associated vessels was confirmed by the lack of SNA reactivity (FIG. 5D). Notably, resistance to anti-VEGF treatment was conferred by the lack of α2-6-sialylation in tumor-associated vasculature, as shown by increased tumor growth (FIG. 5E) and formation of a highly dense tumor vascular network (FIG. 5F). This prominent angiogenic phenotype could be rescued when St6gal1$^{-/-}$ mice were challenged with Gal1-deficient B16 tumors and further treated with the anti-VEGF mAb (FIG. 5G), suggesting that loss of α2-6 linked SA may enhance vascular signaling and angiogenesis by unmasking Gal1-specific ligands.

Furthermore, this angiogenic compensatory program was eliminated when St6gal1$^{-/-}$ mice were implanted with B16 tumors and further treated with anti-VEGF mAb in the presence of the RTK inhibitor Axitinib, which preferentially suppresses VEGFRs signaling (FIG. 5G). Notably, no substantial changes in tumor growth or vascularization were observed in response to anti-VEGF treatment when a sensitive tumor was inoculated into Mgat5$^{-/-}$ mice or when a refractory tumor was grown in St6 gal1$^{-/-}$ mice (data not shown). Thus, reprogramming of the EC glycome, leading to disruption of Gal1-specific ligands, may contribute to circumvent refractoriness to anti-VEGF therapy.

F. Targeting Gal1-N-glycan Axis Promotes Vascular Remodeling and Overcomes Refractoriness to Anti-VEGF Therapy In the search for a therapeutic agent capable of defeating anti-VEGF resistance by interrupting Gal1-N-glycan interactions, the effects of a function-blocking Gal1 mAb (F8.G7), selected by its ability to bind and neutralize Gal1, was evaluated but not with respect to other members of the galectin family (see Ouyang et al., (2011); and Croci et al., *J. Exp. Med.* 209:11, 1985-2000 (2012)). Capillary tube formation, EC migration induced by Gal1, but not VEGF-A (FIGS. 6A and 5A), were specifically prevented by this mAb; Gal1-induced VEGFR2 phosphorylation was inhibited to levels comparable to those attained by MGAT5 silencing through the use of the F8.G7 mAb (FIG. 6B).

To interrupt Gal1-N-glycan interactions in vivo, the F8.G7 mAb (10 mg/kg), either alone or in combination with an anti-VEGF mAb, was infused into syngeneic mice implanted with anti-VEGF refractory (LLC1 and R1.1) or sensitive (B16-F0) tumors. Anti-VEGF resistance displayed by both LLC1 and R1.1 tumors was successfully circumvented by administration of F8.G7 mAb, as evidenced by tumor growth inhibition and reduced vascularization at day 7 following combined treatment (FIGS. 6C and 6D). On the other hand, the therapeutic benefit of anti-VEGF in B16 sensitive tumors was slightly enhanced by the Ab-mediated Gal1 blockade (FIG. 6E). Remarkably, sustained inhibition of tumor growth and vascularization was afforded by a single administration of F8.G7 mAb in mice bearing refractory or sensitive tumors (FIGS. 6C-6E and 10B). Of note, the amounts of secreted Gal1 varied considerably among different tumor types when inoculated in vivo, but dropped substantially following administration of the F8.G7 mAb (FIG. 6F). Thus, mAb-mediated Gal1 blockade limits refractoriness to anti-VEGF therapy and decreases the formation of aberrant vascular networks.

Figure 6J:
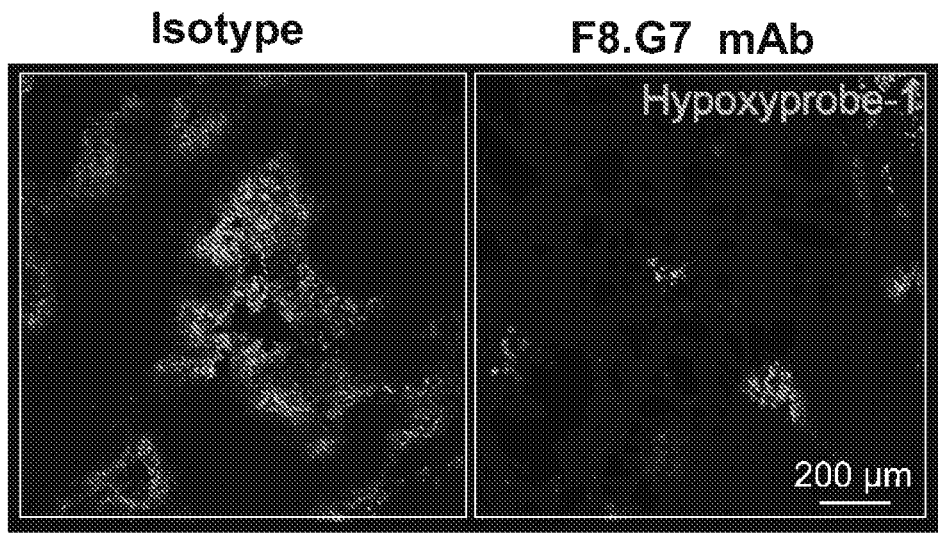

Recent studies suggest that vascular-targeted strategies should combine the traditional mechanism of vessel pruning with the capacity to promote normalization of the remaining tumor vasculature (Carmeliet and Jain, *Nature* 473, 298-307 (2011)). Therefore, a study was conducted to evaluate whether the Gal1 blockade provides a window of opportunity for tumor vessel normalization. As shown in FIGS. 6G-6J, substantial remodeling of the vasculature of B16 tumors at days 4-5 post treatment was caused by the mAb-mediated Gal1 blockade. While a disorganized and heterogeneous vascular architecture (composed of extensive sprouting and large vessels fused to microvessels) was displayed by tumors treated with the control mAb, normal vascular networks (with regard to vessel diameter and distribution with fewer dilated and tortuous vessels) were noted in tumor vasculature of mice treated with the F8.G7 mAb (FIG. 6G). Moreover, greater coverage by pericytes was shown by the resultant vasculature from F8.G7 mAb-treated tumors (FIG. 6H). In fact, a more mature phenotype was displayed by most pericytes in F8.G7 mAb-treated tumors, as revealed by higher expression of α-smooth muscle actin (α-SMA) and lower expression of regulator of G-protein signaling 5 (RGS5) and platelet-derived growth factor receptor (PDGFR-β), when compared to pericytes from control-treated tumors (FIG. 6I). Yet, no significant variations were detected in Desmin expression between F8.G7 mAb-treated tumors and control-treated tumors (FIG. 6I). These phenotypic changes typically delineate the transition from an immature to a mature pericyte profile (Hamzah et al., *Nature* 453, 410-414 (2008)). Supporting these findings, tumor hypoxia was markedly alleviated by administration of F8.G7 mAb, as shown by reduced formation of pimonidazole adducts (FIG. 6J).

Figure 6K:
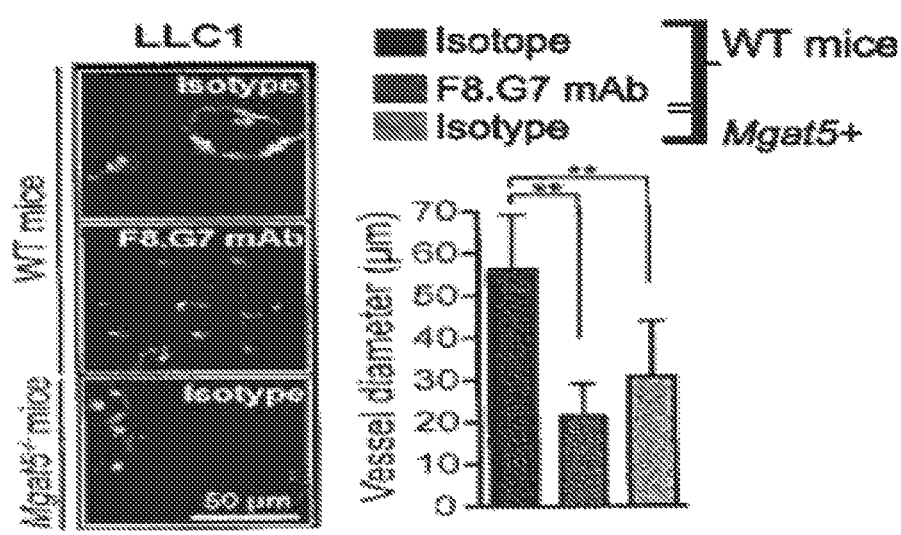
Figure 6L:
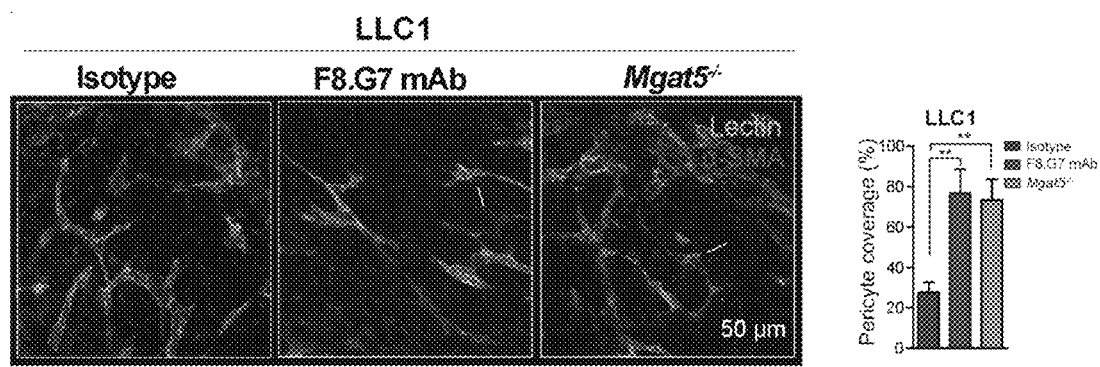

However, vascular normalization and stabilization were not promoted by Gal1 blockade later after treatment, suggesting the transient nature of this effect. Remarkably, a similar vascular remodeling profile was observed following administration of the F8.G7 mAb into WT mice bearing anti-VEGF refractory (LLC1) tumors or when tumors were implanted into Mgat5$^{-/-}$ mice even in the absence of Gal1 blockade (FIGS. 6K and 6L). Thus, disruption of Gal1-N-glycan signaling counteracts the aberrant nature of tumor vasculature not only by attenuating vessel sprouting but also by modulating vessel morphology and stability early after treatment.

G. Disruption of Gal1-N-glycan Interactions Affords Therapeutic Benefits By Controlling Both Vascular and Immune Compartments Because vascular normalization increases the accessibility of immune cells into the tumor parenchyma (Hamzah et al., (2008)) and Gal1 contributes to tumor progression by blunting tumor immunity (Rubinstein et al., *Cancer Cell* 5:3, 241-51 (2004); and Ban et al., *Cancer Res.* 71, 4423-4431 (2011)), the relative contribution of immune and vascular compartments to tumor growth suppression induced by Gal1 blockade were dissected. Whereas a marked decrease in tumor burden was observed due to administration of the anti-Gal1 mAb to tumor-bearing immunocompetent mice (FIGS. 6C-6E), only a partial anti-tumor effect was yielded by treatment of immunodeficient B6.Rag1$^{-/-}$ mice (FIG.

6A), suggesting the contribution of the immune system to the therapeutic effects of F8.G7 mAb.

Figure 7Q:
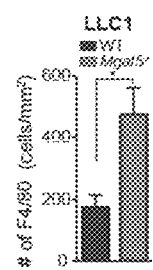
Figure 11A:
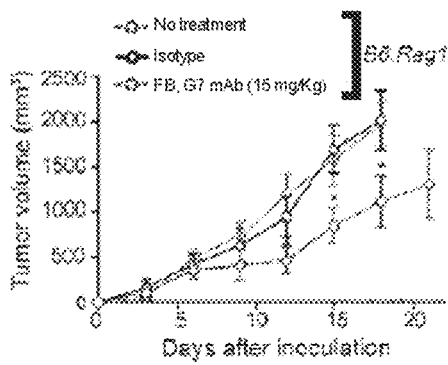
FIGS. 11A-11C show that disruption of Gal1-N-glycan interactions controls both vascular and immune compartments.
Figure 11B:
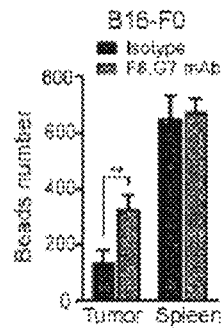
Figure 11C:
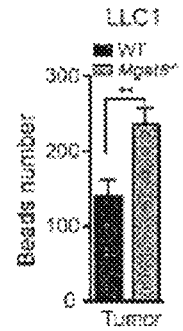
Figure 12:
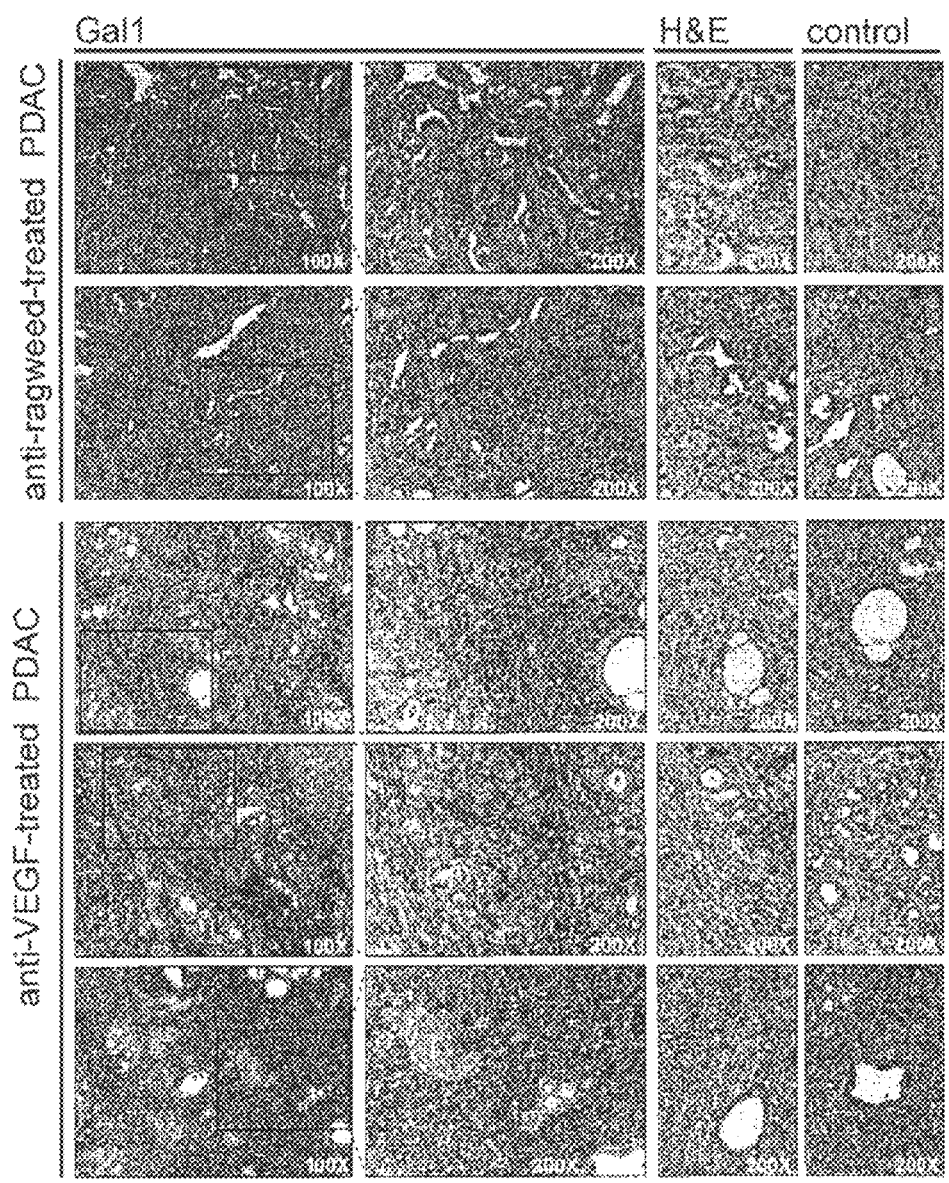
FIG. 12 shows confocal microscopy data of anti-VEGF treated PDAC and anti-ragweed-treated PDAC.
Figure 13A:
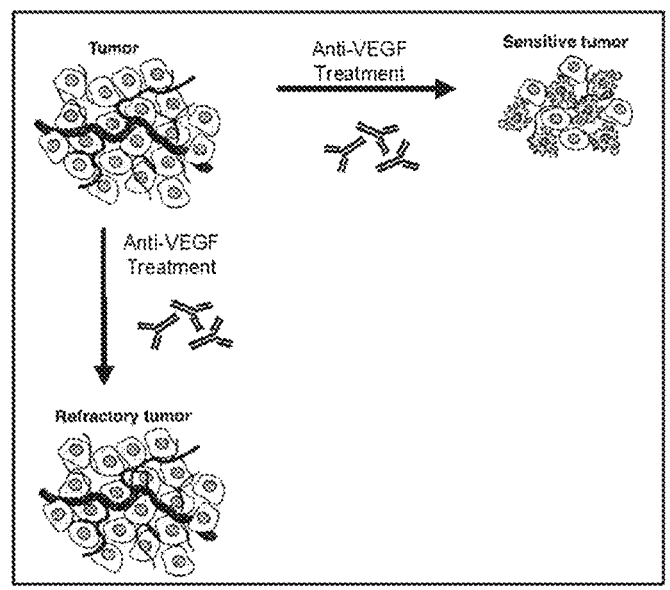
FIG. 13A is a schematic flowchart of anti-VEGF treatment for sensitive and refractory tumors that is based on the glycolysation-dependent pathway for modulating angiogenesis in response to the VEGF blockade described herein. As shown by the right-hand tumor, vessels within anti-VEGF sensitive tumors exhibit high levels of α2-6-linked sialic acid, which prevents Gal1 signaling and angiogenesis. However, as shown by the lower left-hand tumor, the vasculature of anti-VEGF refractory tumors expresses higher amounts of β1-6GlcNAc-branched N-glycans and decreased α2-6 sialylation due to an increase in secreted Gal1. As shown by the different tumors in FIG. 13A, interruption of β1-6GlcNAc-branching in ECs or silencing of tumor-derived Gal1 converts anti-VEGF refractory tumors into anti-VEGF sensitive tumors, whereas elimination of α2-6-linked sialic acid confers resistance to anti-VEGF.
Figure 13B:
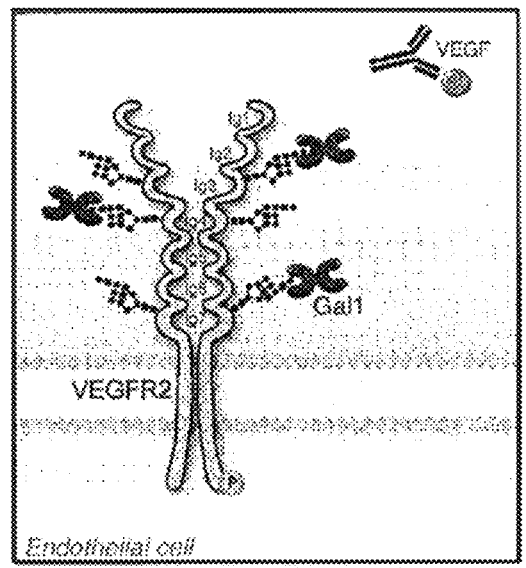
FIG. 13B is a schematic drawing showing how Gal1 mimics VEGF-A signaling through binding to complex N-glycans on VEGFR2 Ig domains (glycosylation sites) Ig-3, Ig-4, and Ig-7.

Investigation of the connection between immune and vascular programs controlled by Gal1-N-glycan interactions was undertaken to explore whether vessel remodeling induced by F8.G7 mAb was accompanied by augmented T-cell responses. T-cell proliferation was stimulated in mice bearing B16-F0 tumors, and the synthesis and secretion of IFN-γ and IL-17 by tumor-draining lymph node (TDLN) cells were restimulated ex vivo, by the therapeutic administration of the F8.G7 mAb (FIGS. 7A-7G). In contrast, tumor-specific IL-10 production was blunted by interruption of Gal1 signaling (FIGS. 7D and 11B). Moreover, a dramatic increase in the number of TDLN and tumor-infiltrating IFN-γ-producing $CD8^+$ T cells was detected in F8.G7 mAb- versus control-treated mice (FIGS. 7H-7J). This immunological phenotype was confirmed in mice inoculated with LLC1 and treated with F8.G7 mAb (FIGS. 7K-7Q).

To elucidate the contribution of N-glycan branching to this effect, LLC1 tumors were inoculated into $Mgat5^{-/-}$ mice. Remarkably, the immunostimulatory effects of Gal1 blockade was mirrored by MGAT5 deficiency, as revealed by greater amounts of IFN-γ and IL-17 (FIGS. 7K and 7L) and diminished IL-10 production (FIG. 7M) by TDLN from tumor-bearing $Mgat5^{-/-}$ mice. Moreover, a higher frequency of IFN-γ-producing $CD4^+$ and $CD8^+$ T cells (FIGS. 7N and 7O) and an increased number of intratumoral $CD8^+$ T cells and $F4/80^+$ macrophages was displayed in tumors growing in mice lacking β1-6GlcNAc-branched N-glycans compared to WT mice (FIGS. 7P and 7Q).

Figure 7R:
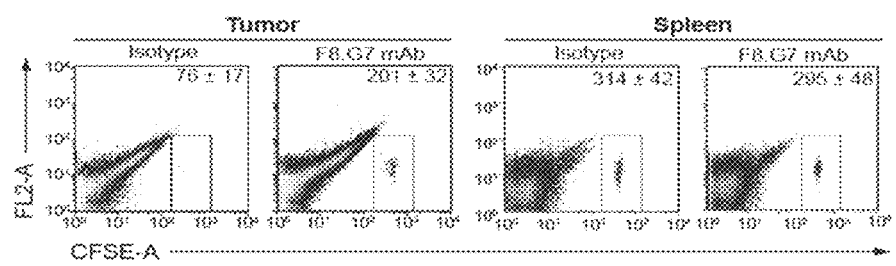

T cells obtained from tumor-bearing mice were labeled with the CFSE dye and adoptively transferred into mice bearing the same tumor but treated with F8.G7 or control mAb. Tumor parenchyma was reached by a greater number of T cells in mice receiving F8.G7 mAb, as compared to those treated with control isotype (FIG. 7R), suggesting augmented influx of immune cells subsequent to vessel normalization. In contrast, no differences were observed in the number of $CFSE^+$ T cells in spleens of tumor-bearing recipient mice (FIG. 7R). To rule out the possibility that Gal1 blockade may affect immune cell recruitment by influencing chemotaxis, similar experiments were performed using fluorescently-labeled beads as a non-cellular approach. An increased access of fluorescently-labeled beads to the tumor parenchyma of F8.G7 mAb-treated, as compared to control-treated, mice was revealed by in vivo tracking (FIGS. 6B and 6C). This effect was also apparent in $Mgat5^{-/-}$ mice implanted with LLC1 tumors (FIGS. 6K and L), thus validating the contribution of complex N-glycans to the vascular remodeling effect. These results emphasize the dual and interrelated effects of blocking Gal1-N-glycan interactions, which contribute to restrain tumor growth by attenuating aberrant angiogenesis and potentiating tumor immunity.

Discussion of Results

The results demonstrate that interactions between Gal1 and specific N-glycans decorating VEGFR2 can substitute for the absence of VEGF-A to promote receptor signaling and preserve angiogenesis in cancers or tumors refractory to anti-VEGF. Tumor-associated stimuli, including hypoxia and immunosuppression, fuel this circuit by increasing the repertoire of non-sialylated complex-type N-glycans on ECs, whereas pro-inflammatory signals tend to interrupt exposure of Gal1-specific glyco-epitopes. In this regard, tumor necrosis factor, a major pro-inflammatory cytokine, favors the transcription of genes encoding glycosyltransferases responsible for regulating leukocyte trafficking by creating specific selectin ligands (Garcia-Vallejo et al., *J. Cell Physiol.* 206, 203-210 (2006); Willhauck-Fleckenstein et al., *Angiogenesis* 13, 25-42 (2010)). These results emphasize the versatility of the EC glycome and its adaptability to cellular physiology.

Although Gal1-glycan interactions may prolong cell surface residency of VEGFR2, which amplifies responses to cognate ligand, it was discovered that receptor retention and signaling may also proceed in the absence of VEGF-A, highlighting the contribution of lectin-glycan recognition systems to ligand-independent receptor activation. Although previous findings reported direct interactions between Gal1 and NRP-1 leading to VEGFR2 phosphorylation (Hsie et al., *Oncogene* 27, 3746-3753 (2008)), the present findings demonstrate that Gal1 functions through direct interaction with Ig-3, Ig-4 and Ig-7 domains of VEGFR2. Importantly, Gal1 mutants lacking carbohydrate-binding activity do not alter EC biology, highlighting the major contribution of glycosylation to this effect.

The above experiments demonstrate the central role of endogenous N-glycans and their associated binding partners in ligand-independent receptor activation with critical implications in therapeutic settings associated with growth factor withdrawal.

Furthermore, the inventors have identified a glycosylation-based circuit that preserves angiogenesis in tumors refractory to anti-VEGF treatment and couples tumor hypoxia to vascularization. Notably, it was found that hypoxia not only induced dramatic changes in the EC surface glycome, leading to the creation of Gal1-specific glycans (as shown in FIG. 1), but also augmented Gal1 expression through mechanisms involving nuclear factor (NF)-kB-activation (Croci et al., *J. Exp. Med.* 29:11, 1985-2000 (2012)). A "Gal1-permissive" glycophenotype was evident on ECs exposed to anti-VEGF refractory, but not on sensitive tumors in response to hypoxia or VEGF blockade. Hence, rather than the up-regulation of a single pro-angiogenic cytokine, the Gal1-N-glycan axis emerges as a synchronized rescue program that is intimately connected with the VEGFR2 signaling pathway and bolsters tumor immunosuppressive networks.

Although other members of the galectin family, including Gal3 and Gal8, can also promote angiogenesis (Nangia-Makker et al., *Am. J. Pathol.* 156, 899-909 (2000); Markowska et al., *J. Biol. Chem.* 286, 29913-29921 (2011); Delgado et al., *FASEB J.* 25, 242-254 (2011)), only Gal1 was up-regulated by tumor hypoxia following anti-VEGF treatment. This suggests that the spatiotemporal regulation of individual galectins in the tumor microenvironment, their selective modulation by hypoxia, and the repertoire of glycan structures displayed by the tumor vasculature, together determine the contribution of individual glycan-binding proteins to revascularization programs. In this regard, whereas most galectins interact with poly-LacNAc structures, considerable differences exist in glycan-binding preferences among individual members of the galectin family (Rabinovich and Croci, *J. Exp. Med.* 209:11, 1985-2000 (2012)), which could potentially account for functional divergences in receptor binding and biological activity.

Based on the study undertaken by the inventors, it was confirmed that elimination of β1-6GlcNAc branching in MGAT5-deficient mice converted anti-VEGF "refractory" tumors into anti-VEGF "sensitive" tumors, as it prevented Gal1 signaling and angiogenesis. Although secreted MGAT5 may act on heparan sulfate to promote the release of pro-angiogenic bFGF through a glycan-independent pathway (Saito et al., *J. Biol. Chem.* 277, 17002-17008 (2002)), this mechanism is unlikely to mediate the reported revascularization program as: (1) a blocking anti-bFGF mAb did not modulate the pro-angiogenic effect of Gal1; (2) angiogenesis did not occur in the absence of Gal1; and (3) treatment with the N-glycan processing inhibitor swainsonine recapitulated the effects of MGAT5 silencing. Whereas MGAT5 deficiency has not been previously investigated in the context of tumor angiogenesis, studies revealed slower tumor growth in Mgat5$^{-/-}$ mice compared to control littermates through mechanisms involving focal adhesion signaling (Granovsky et al., Nat. Med. 6, 306-312 (2000)), thus substantiating the role of branched complex N-glycans in tumor promotion. Conversely, St6gal1 ablation abrogated sensitivity to anti-VEGF treatment, suggesting a major role for α2-6-linked SA in preventing revascularization. This effect was associated with elimination of Gal1-N-glycan signaling via VEGFR2, as it was prevented by Gal1 silencing or by administration of axitinib, an RTK inhibitor which preferentially perturbs VEGFRs signaling. However, α2-6 sialylation may also influence EC biology by modulating surface retention of CD31 (Kitazume et al., J. Biol. Chem. 285, 6515-21 (2010)), suggesting diverse roles for this glycan structure in shaping angiogenic phenotypes.

Together with an active search for VEGF-independent compensatory pathways, a major priority in clinical settings is the identification of predictive biomarkers of anti-VEGF responsiveness which might help tailor anti-angiogenic therapies. Studies in selected cohorts of patients revealed the contribution of soluble VEGF-A, bFGF and IL-6 as possible biomarkers of anti-VEGF resistance (Potente et al., Cell 146, 873-887 (2011)). The above findings suggest an alternative signature that could help to define refractoriness to anti-VEGF treatment by combining Gal1 up-regulation with the selective induction of a "Gal1-permissive" vascular glycophenotype (SNA$^{lo}$, L-PHA$^{hi}$, LEL$^{hi}$). Although the precise mechanisms underlying this differential glycan profile remain elusive, no significant differences were observed in the amounts of TGF-β$_1$ and bFGF (cytokines capable of imprinting a "Gal1-permissive" EC glycophenotype) in anti-VEGF "refractory" versus anti-VEGF "sensitive" tumors.

Additional factors triggered by the hypoxic microenvironment typical of anti-VEGF refractory tumors (see Bergers and Hanahan, Nat. Rev. Cancer 8:8, 592-603 (2008)) will likely contribute to reprogram the in vivo vascular glycome. Therefore, in addition to regulating malignant transformation, metastatic behavior and immune cell fate (Rabinovich and Croci, J. Exp. Med. 209:11, 1985-2000 (2012)), differential glycosylation can also serve as an "on-and-off" switch that controls sensitivity or refractoriness to anti-angiogenic treatment. Whether lectin-glycan recognition systems serve as backup mechanisms for other biological therapies targeting glycosylated receptors remains to be elucidated.

In the quest for finding a specific agent capable of disrupting the Gal1-N-glycan axis, a specific anti-Gal1 neutralizing mAb (F8.G7) was generated and validated for therapeutic efficacy. See Ouyang et al., (2011); Croci et al., J. Exp. Med. 29:11, 1985-2000 (2012). Administration of a F8.G7 mAb was found to suppress tumor growth and prevent revascularization in anti-VEGF refractory tumors, while slightly enhancing the therapeutic benefits of the VEGF blockade in tumors sensitive to this treatment. This therapeutic response did not appear to involve undesired "off-target" effects, as F8.G7 mAb did not bind to other members of the galectin family (see Croci et al., J. Exp. Med. 29:11, 1985-2000 (2012)), was active at relatively low concentrations (5-10 mg/kg), and phenocopied the consequences of MGAT5 deficiency. Similar to the effects of other anti-angiogenic agents (Carmeliet and Jain, Nature 473, 298-307 (2011)), mAb-mediated Gal1 blockade not only suppressed tumor vascular supply, but also induced transient vessel normalization early after treatment, as reflected by increased pericyte coverage and maturation, alleviation of tumor hypoxia and improved penetration of T cells into the tumor parenchyma, which resulted in amplification of immune responses. Although the precise mechanism underlying this effect remains uncertain, it was discovered that inoculation of refractory tumors into Mgat5$^{-/-}$ mice phenocopied vessel normalization and stabilization induced by Gal1 blockade, suggesting that, similar to VEGF-A, Gal1 interactions with complex N-glycans might alter pericyte interactions with nascent vascular sprouts. This is consistent with the ability of Gal1 to modulate the attachment of vascular smooth muscle cells (Moiseeva et al., J. Vasc. Res. 36, 47-58 (1999)).

The respective contributions of vascular- and immune-mediated mechanisms to the therapeutic benefits of Gal1 blockage are as follows: whereas the role of the vascular compartment is unequivocally demonstrated by the broad inhibition of tumor vascular networks following the Gal1 blockade, the contribution of the immune system is substantiated by the augmented T$_H$1 and T$_H$-17 responses in TDLNs, the increased frequency of CD8$^+$ T cells in the tumor parenchyma, and the partial therapeutic benefit of F8.G7 mAb in Rag1$^{-/-}$ mice. These mechanisms appear to be interconnected as vessel normalization influences tumor immunity by facilitating the access of immune cells to tumor sites that, in the absence of Gal1, can display augmented effector function. Although Lgals1$^{-/-}$ and Mgat5$^{-/-}$ embryos develop normally, both mutant strains display abnormal responses to extrinsic stimuli including increased T-cell reactivity and autoimmune responses (Toscano et al., Cyt. Growth Fact. Rev. 18, 57-71 (2007); Dennis et al., Cell 139, 1229-1241 (2009)). It was found that, in response to tumor growth, MGAT5 deficiency completely recapitulated the angioregulatory and immunostimulatory phenotypes elicited by Gal1 ablation, thus reinforcing the role of complex N-glycans in tumor biology. Given the increased appreciation of Ab-mediated immunotherapy in clinical oncology (Coussens et al., Science 339, 286-291 (2013)), targeting Gal1-N-glycan interactions may also contribute to immunotherapeutic modalities aimed at releasing the brakes of tumor immunity, including those involving CTLA-4 or PD-1/PD-L1 blockade.

It is also envisioned that these findings may have broader implications in other clinical settings involving disregulated angiogenesis including age-related macular degeneration, diabetic retinopathy and cardiovascular diseases.

As shown by the results described herein, antibody-mediated Gal-1 blockage alleviates tumor hypoxia and fosters the influx of anti-tumor immune cells into the tumor bed. This vascular remodeling function recapitulates that observed with other anti-angiogenic agents, which can transiently normalize tumor vasculature to make it more efficient for oxygenation, drug delivery, and immune cell entry. See also, Jain R. K., Science 307, 58-62 (2005). Moreover, as bone marrow-derived myeloid cells express considerable amounts of Gal1 (Ilarregui et al., Nat. Immunol. 10, 981-991 (2009)), their inhibition might also contribute to eliminating the vasculogenic potential of these cells. Although galectin inhibitors that block the carbohydrate recognition domain have been developed (Ingrassia et al., Curr. Med. Chem. 13, 3513-3527 (2006); Stannard et al., Cancer Lett. 299, 95-110 (2010)), most of these inhibitors lack selectivity for individual members of the galectin family and often display weak ligand affinities and poor bioavailability. These shortcomings hinder the rapid translation of these compounds into the clinic, underscoring the advantages of a mAb that specifically neutralizes Gal1 and targets both vascular and immune compartments.

Moreover, the results described herein demonstrate a strong correlation between Gal1 expression and the extent of tumor angiogenesis in human melanoma biopsies. In addition, Gal1 expression delineated highly angiogenic KS from benign vascular lesions with shared morphologic and molecular features, indicating its potential use as a differential diagnostic biomarker in vascular malignancies. These data have additional implications as Gal1 blockade may ameliorate AIDS-related KS not only by limiting aberrant angiogenesis, but also by restoring the balance between $T_H17$ and $T_{reg}$ cell populations (Favre et al., *PLoS Pathog* 5, e1000295 (2009)).

Since F8.G7 is a mouse anti-Gal1 blocking monoclonal antibody, new fully human monoclonal antibodies from scFV library were generated. This effort was intended to extend these antibodies for treatment of patients resistant to anti-VEGF treatment. New anti-Gal1 mAbs were obtained after four rounds of screening with good enriching effect and higher differences between samples screened and controls. Then, different clones were picked up and submitted to DNA sequencing. Clones with same sequence were discarded. Two clones (21 and 42) were cloned into soluble scFv-AP expression vector and were successfully expressed. Specific binding of antibodies was confirmed by soluble scFv-AP ELISA. Two new scFv were identified by phage display in human scFv library. After selection, it was decided to continue the development of a full length IgG1 human antibody with the sequence corresponding to clone 21 and clone 42 of the following tables.

```
Clone 21 Sequences:
VH (SEQ ID NO: 15), CDRs are framed in bold
(SEQ ID NOs: 16-18)
EVQLLESGGGLVQPGGSLRLSCAASGFTFSSYAMSWVRQAPGKGLE

WVSEIGRVGVNTLYADSVKGRFTISRDNSKNTLYLQMNSLRAEDTA

VYYCAKKATQFDYWGQGTLVTVSS

VK (SEQ ID NO: 19), CDRs are framed in bold
(SEQ ID NOs: 20-22)
DIQMTQSPSSLSASVGDRVTITCRASQSISSYLNWYQQKPGKAPKL

LIYRASRLQSGVPSRFSGSGSGTDFTLTISSLQPEDFATYYC**QQTI

GPPDT**FGQGTKVEIKR

Clone 42 Sequences:
VH (SEQ ID NO: 23), CDRs are framed in bold
(SEQ ID NOs: 24-26)
EVQLLESGGGLVQPGGSLRLSCAASGFTFSSYAMSWVRQAPGKGLE

WVSGISGSGDYTSYADSVKGRFTISRDNSKNTLYLQMNSLRAEDTA

VYYCAKGYGAFDYWGQGTLVTVSS

VK (SEQ ID NO: 27), CDRs are framed in bold
(SEQ ID NOs: 28-30)
DIQMTQSPSSLSASVGDRVTITCRASQSISSYLNWYQQKPGKAPKL

LIYGASWLQSGVPSRFSGSGSGTDFTLTISSLQPEDFATYYC**QQSA

NYPST**FGQGTKVEIKR
```

Figure 14A:
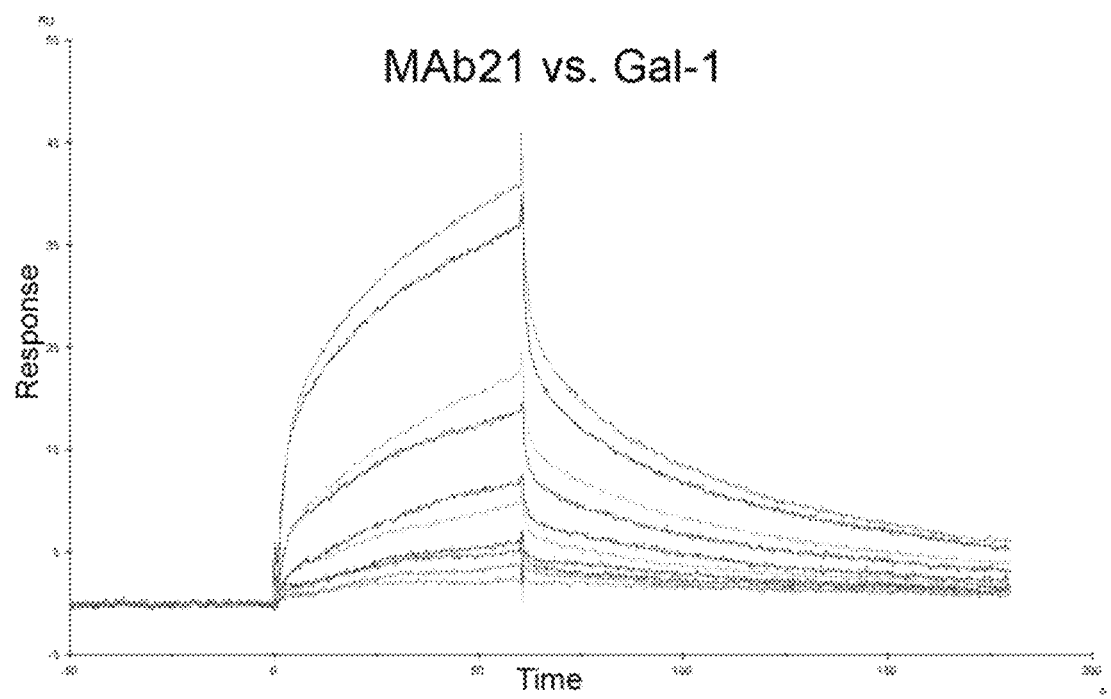
FIG. 14A and FIG. 14B are plots of dose-response (RU) curves of the interaction between monoclonal antibodies (MAb21—FIG. 14A; MAb42—FIG. 14B) and human recombinant Gal-1.
Figure 14B:
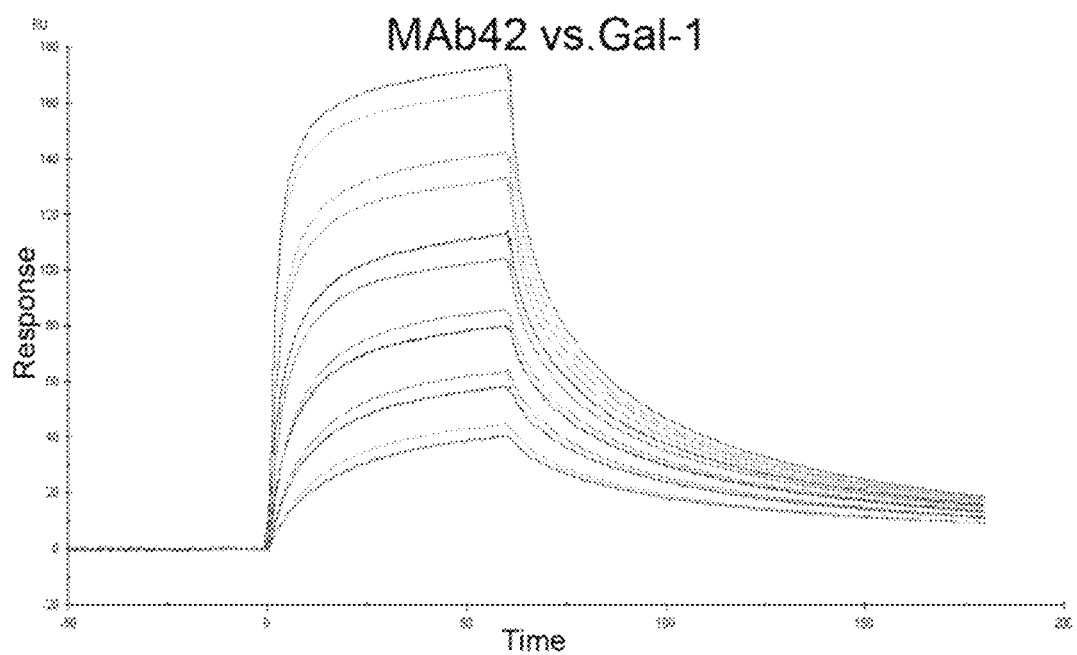

Also conducted was an affinity assay (SPR) for the newly developed fully human anti-Gal1 monoclonal antibodies. In order to characterize affinities of the new anti-Gal-1 monoclonal antibodies, dose-response (RU) curves were collected of the interactions between the monoclonal antibodies and human recombinant Gal-1 (FIG. 14A and FIG. 14B).

By using the BIAEvaluation 3.0 software in a kinetics model of interaction adjustment 1:1, kinetic parameters, constants of dissociation (Kd) and affinity (Ka) were calculated.

|  | Kd (M) | Ka (M)−1 |
|---|---|---|
| Clone 21 | 1.54E−06 | 6.49E+05 |
| Clone 42 | 1.31E−07 | 7.63E+06 |

The two monoclonal antibodies (anti-Gal1 Clone 21 and anti-Gal1 Clone 42) showed different affinities, although both of them demonstrated high specific interactions with human recombinant Gal1.

Figure 15A:
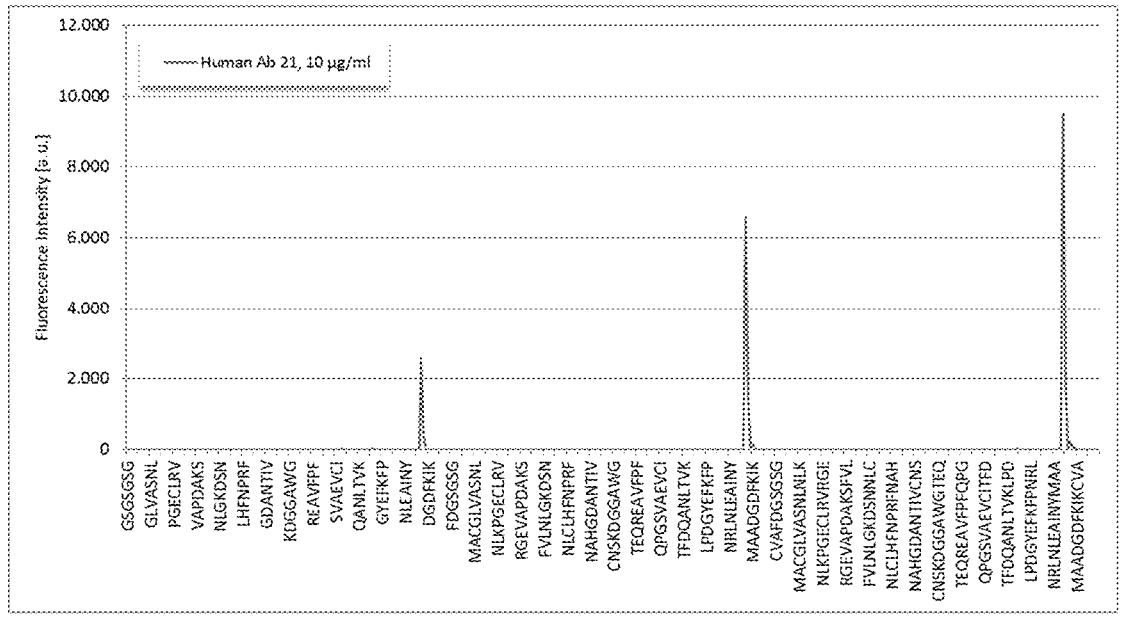
FIG. 15A and FIG. 15B depict conformational epitope mapping analyses against epitope-like spots formed by adjacent peptides within the consensus motif MAADGDF (SEQ ID NO: 31) (Human Ab 21, 10 µg/mL—FIG. 15A; Human Ab 42, 10 µg/mL—FIG. 15B). Figures disclose SEQ ID NOS 32-73 and 32-73, respectively in order of appearance.
Figure 15B:
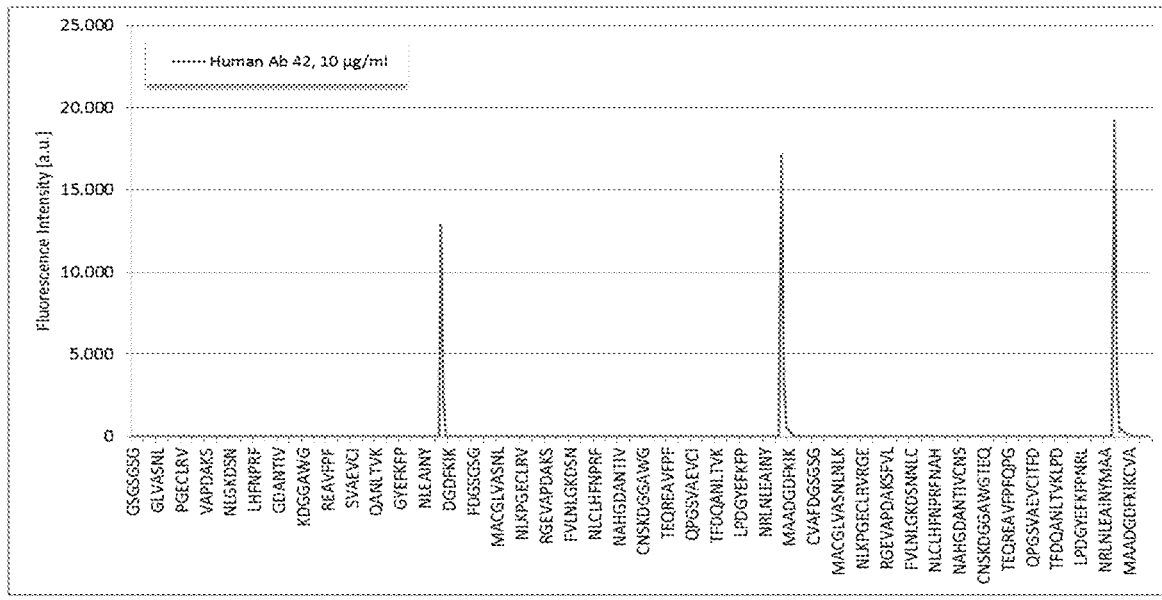

Epitope mapping: In order to determine the specific conformational epitopes recognized by the new anti-Gal1 antibodies, a PEPperMAP® Conformational Epitope Mapping Analysis was performed. Human antibodies (clone 21 and clone 42) showed virtually identical responses against epitope-like spot patterns formed by adjacent peptides within the consensus motif (MAADGDF (SEQ ID NO: 31)) with all three peptide lengths (FIG. 15A, FIG. 15B). For clone 21, moderate to high binding activity was found against epitope-like spot formed by adjacent peptides with the consensus motif MAADGDF (SEQ ID NO: 31) with all three peptide lengths. Moreover, higher spot intensities were observed with increasing peptide length. Clone 42 had a higher binding activity and higher spot intensities compared with clone 21.

Figure 16:
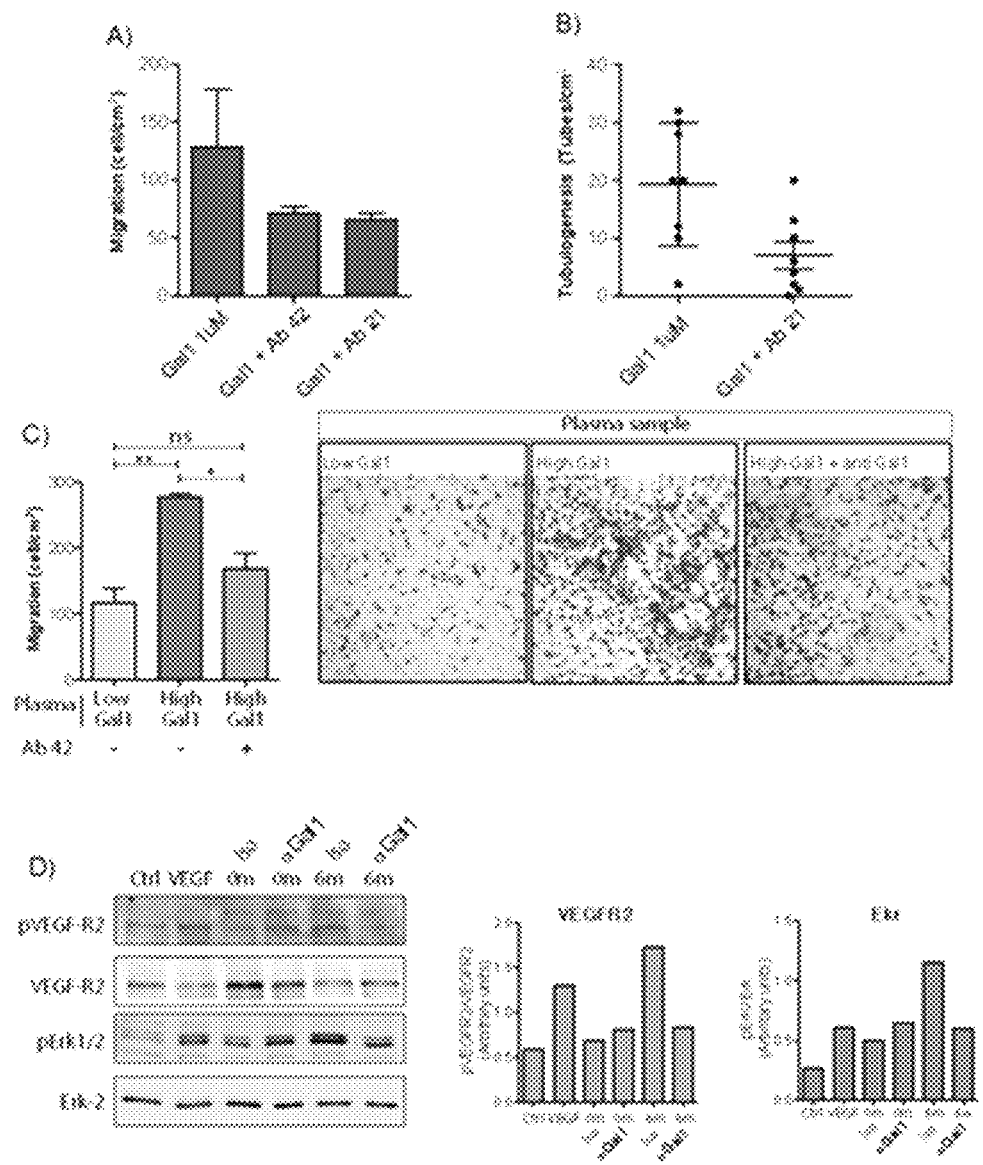
FIG. 16A-D depict the inhibition of Gal-1-induced angiogenesis by fully human anti-Gal1 antibodies. Migration of HUVEC cells in the presence of Gal-1 (1 mM) two anti-Gal-1 human mAb (1.5 mM) (FIG. 16A), or mouse anti-Gal1 (2 mM) (FIG. 16B).

Because hypoxia-promoting angiogenesis may be a key adaptive response to anti-VEGF-treatment and Gal-1 can play a key role in this effect, whether anti-Gal-1 human blocking monoclonal antibodies could eliminate the pro-angiogenic activity of this lectin was investigated. To address this issue, the inhibitory activity of clone 21 and clone 42 in Gal1-induced cell migration (FIG. 16A) and formation of tubular structures (tubulogensis) (FIG. 16B) was tested. Both antibody clones significantly blocked Gal-1 activity in endothelial cells. To address the relevance of anti-Gal-1 monoclonal antibodies in preventing Gal1-induced angiogenesis in anti-VEGF (Bevacizumab)-treated tumors, the pro-angiogenic potential was analyzed of plasma samples from anti-VEGF-treated patients. Blockade of Gal1 activity by fully human anti-Gal1 antibodies prevented Gal1-induced angiogenesis (FIG. 16C) and VEGFR2 signaling (FIG. 16D). These data reinforced the concept that Gal1 blockage was central for circumventing neovascularization and supported the clinical relevance of anti-Gal-1 antibodies in the inhibition of angiogenesis.

EQUIVALENTS

It should be understood that various principles of the disclosure have been described in illustrative embodiments. However, many combinations and modifications of the above described methods and components, and compositions used in the practice of the claimed invention, in addition to those not specifically described, may be varied without departing from the scope of the disclosure. Such variations and modifications could be ascertained by persons skilled in the art using no more than routine experimentation, and are likewise encompassed by the present disclosure.

What is claimed is:

1. A method for inhibiting angiogenesis in a cancer refractory to anti-VEGF, comprising:
   (a) identifying a cancer cell as refractory to anti-VEGF;
   (b) contacting the refractory cancer cell with an effective amount of an anti-Gal1 monoclonal antibody or antigen binding fragment thereof that binds to Galectin-1 (Gal1) or a Gal1 fragment to thereby inhibit angiogenesis in the refractory cancer cell, wherein the anti-Gal1 monoclonal antibody or antigen binding fragment thereof is selected from the group consisting of:
   i) an anti-Gal1 monoclonal antibody or antigen binding fragment thereof comprising a heavy chain variable domain of SEQ ID NO:15 and a light chain variable domain of SEQ ID NO:19;
   ii) an anti-Gal1 monoclonal antibody or antigen binding fragment thereof comprising a heavy chain variable domain with three CDRs of SEQ ID NOs:16-18 and a light chain variable domain with three CDRs of SEQ ID NOs:20-22;
   iii) an anti-Gal1 monoclonal antibody or antigen binding fragment thereof comprising a heavy chain variable domain of SEQ ID NO:23 and a light chain variable domain of SEQ ID NO:27; and
   iv) an anti-Gal1 monoclonal antibody or antigen binding fragment thereof comprising a heavy chain variable domain with three CDRs of SEQ ID NOs:24-26 and a light chain variable domain with three CDRs of SEQ ID NOs:28-30.

2. The method according to claim 1, wherein the inhibition of angiogenesis decreases angiogenesis in the cancer cell by at least 10% with respect to a level of angiogenesis in a corresponding control refractory cancer cell.

3. The method according to claim 1, wherein the contacting of the cancer cell with the anti-Gal1 monoclonal antibody or antigen binding fragment thereof occurs in vivo.

4. The method according to claim 1, wherein the contacting of the cancer cell with the anti-Gal1 monoclonal antibody or antigen binding fragment thereof occurs in vitro.

5. The method according to claim 1, wherein the anti-Gal1 monoclonal antibody or antigen-binding fragment thereof is: chimeric, humanized, or human antibody.

6. The method according to claim 1, wherein the monoclonal antibody is selective for Gal1 over other galectins.

7. The method according to claim 1, wherein the refractory cancer cell in which angiogenesis is inhibited is a cell selected from the group consisting of LLCI Lewis lung carcinoma, R1.1 T cell lymphoma, and pancreatic cancer.

8. The method according to claim 1, further comprising contacting the refractory cancer cell with a second agent that is an anti-angiogenic agent.

9. The method according to claim 8, wherein the anti-angiogenic agent is an anti-VEGF antibody.

10. A method for treating a subject having a cancer refractory to anti-VEGF treatment, comprising:
administering to the subject having the refractory cancer to the anti-VEGF treatment a therapeutically effective amount of anti-Gal1 monoclonal antibody or antigen binding fragment thereof that binds to Galectin-1 (Gal1) or a Gal1 fragment wherein the anti-Gal1 monoclonal antibody or antigen binding fragment thereof is selected from the group consisting of:
i) an anti-Gal1 monoclonal antibody or antigen binding fragment thereof comprising a heavy chain variable domain of SEQ ID NO:15 and a light chain variable domain of SEQ ID NO:19;
ii) an anti-Gal1 monoclonal antibody or antigen binding fragment thereof comprising a heavy chain variable domain with three CDRs of SEQ ID NOs:16-18 and a light chain variable domain with three CDRs of SEQ ID NOs:20-22;
iii) an anti-Gal1 monoclonal antibody or antigen binding fragment thereof comprising a heavy chain variable domain of SEQ ID NO:23 and a light chain variable domain of SEQ ID NO:27; and
iv) an anti-Gal1 monoclonal antibody or antigen binding fragment thereof comprising a heavy chain variable domain with three CDRs of SEQ ID NOs:24-26 and a light chain variable domain with three CDRs of SEQ ID NOs:28-30.

11. The method according to claim 10, wherein the anti-Gal1 monoclonal antibody or antigen binding fragment thereof administered to the subject is therapeutically effective in:
(a) slowing or inhibiting growth of the refractory cancer;
(b) preventing spreading of the refractory cancer;
(c) preventing recurrence of a previously spread tumor associated with the refractory cancer;
(d) preventing spreading of one or more metastases associated with the refractory cancer;
(e) reducing a size of a tumor associated with the refractory cancer; and/or
(f) preventing recurrence of the refractory cancer that has been previously treated.

12. The method according to claim 10, wherein the anti-Gal1 monoclonal antibody or antigen binding fragment thereof that inhibits angiogenesis upregulates an immune response.

13. The method according to claim 10, wherein the anti-Gal1 monoclonal antibody or antigen binding fragment thereof is administered to the subject in a pharmaceutical composition that comprises a pharmaceutically acceptable carrier selected from the group consisting of solvents, dispersion media, coatings, antibacterial agents, antifungal agents, isotonic agents and absorption delaying agents.

14. The method according to claim 13, wherein the pharmaceutical excipient is selected from the group consisting of starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol.

15. The method according to claim 13, wherein the pharmaceutical composition is administered to the subject in combination with at least one other mode of therapy selected from the group consisting of radiotherapy, chemotherapy, and surgery.

16. The method according to claim 13, wherein the pharmaceutical composition is administered to the subject by a mode selected from the group consisting of parenteral, intravenous, intradermal, subcutaneous, inhalation, transdermal, transmucosal, and rectal.

17. The method according to claim 13, wherein the pharmaceutical composition is administered to the subject in a form selected from the group consisting of an injectable solution, an aerosol, a nasal spray, a suppository, a cream, a gel, a tablet, and a capsule.

18. The method according to claim 10, wherein the cancer refractory to anti-VEGF is not breast cancer or Kaposi's sarcoma.

19. The method according to claim 16, further comprising administering to the subject an anti-VEGF antibody.

20. The method according to claim 1, wherein the anti-Gal1 monoclonal antibody or antigen binding fragment thereof comprises a heavy chain variable domain of SEQ ID NO:15 and a light chain variable domain of SEQ ID NO:19.

21. The method according to claim 1, wherein the anti-Gal1 monoclonal antibody or antigen binding fragment thereof comprises a heavy chain variable domain with three CDRs of SEQ ID NOs:16-18 and a light chain variable domain with three CDRs of SEQ ID NOs:20-22.

22. The method according to claim 1, wherein the anti-Gal1 monoclonal antibody or antigen binding fragment thereof comprises a heavy chain variable domain of SEQ ID NO:23 and a light chain variable domain of SEQ ID NO:27.

23. The method according to claim 1, wherein the anti-Gal1 monoclonal antibody or antigen binding fragment thereof comprises a heavy chain variable domain with three CDRs of SEQ ID NOs:24-26 and a light chain variable domain with three CDRs of SEQ ID NOs:28-30.

* * * * *

SEQUENCE LISTING

<160> NUMBER OF SEQ ID NOS: 73

<210> SEQ ID NO 1
<211> LENGTH: 408
<212> TYPE: DNA
<213> ORGANISM: Homo sapiens

<400> SEQUENCE: 1

| | | |
|---|---|---|
| atggcttgtg gtctggtcgc cagcaacctg aatctcaaac ctggagagtg ccttcgagtg | 60 |
| cgaggcgagg tggctcctga cgctaagagc ttcgtgctga acctgggcaa agacagcaac | 120 |
| aacctgtgcc tgcacttcaa ccctcgcttc aacgccacg gcgacgccaa caccatcgtg | 180 |
| tgcaacagca aggacggcgg ggcctggggg accgagcagc gggaggctgt ctttcccttc | 240 |
| cagcctggaa gtgttgcaga ggtgtgcatc accttcgacc aggccaacct gaccgtcaag | 300 |
| ctgccagatg gatacgaatt caagttcccc aaccgcctca acctggaggc catcaactac | 360 |
| atggcagctg acggtgactt caagatcaaa tgtgtggcct ttgactga | 408 |

<210> SEQ ID NO 2
<211> LENGTH: 135
<212> TYPE: PRT
<213> ORGANISM: Homo sapiens

<400> SEQUENCE: 2

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135

<210> SEQ ID NO 3
<211> LENGTH: 4071
<212> TYPE: DNA
<213> ORGANISM: Homo sapiens

<400> SEQUENCE: 3

| | | |
|---|---|---|
| atgcagagca aggtgctgct ggccgtcgcc ctgtggctct gcgtggagac ccgggccgcc | 60 |
| tctgtgggtt tgcctagtgt ttctcttgat ctgcccaggc tcagcataca aaagacata | 120 |
| cttacaatta aggctaatac aactcttcaa attacttgca ggggacagag ggacttggac | 180 |
| tggcttttggc ccaataatca gagtggcagt gagcaaaggg tggaggtgac tgagtgcagc | 240 |
| gatggcctct ctgtaagac actcacaatt ccaaaagtga tcggaaatga cactggagcc | 300 |
| tacaagtgct ctctaccggga aactgacttg gcctcggtca tttatgtcta tgttcaagat | 360 |

```
tacagatctc catttattgc ttctgttagt gaccaacatg gagtcgtgta cattactgag    420
aacaaaaaca aaactgtggt gattccatgt ctcgggtcca tttcaaatct caacgtgtca    480
ctttgtgcaa gatacccaga aaagagattt gttcctgatg gtaacagaat tcctgggac    540 agcaagaagg gctttactat tcccagctac atgatcagct atgctggcat ggtcttctgt    600
gaagcaaaaa ttaatgatga agttaccag  tctattatgt acatagttgt cgttgtaggg    660
tataggattt atgatgtggt tctgagtccg tctcatggaa ttgaactatc tgttggagaa    720
aagcttgtct taaattgtac agcaagaact gaactaaatg tggggattga cttcaactgg    780
gaataccctt cttcgaagca tcagcataag aaacttgtaa accgagacct aaaaacccag    840
tctgggagtg agatgaagaa atttttgagc accttaacta tagatggtgt aacccggagt    900
gaccaaggat tgtacacctg tgcagcatcc agtgggctga tgaccaagaa gaacagcaca    960
tttgtcaggg tccatgaaaa acctttttgtt gcttttggaa gtggcatgga atctctggtg   1020
gaagccacgg tgggggagcg tgtcagaatc cctgcgaagt accttggtta cccacccccca  1080 gaaataaaat ggtataaaaa tggaataccc cttgagtcca atcacacaat taaagcgggg   1140
catgtactga cgattatgga agtgagtgaa agagacacag gaaattacac tgtcatcctt   1200
accaatccca tttcaaagga gaagcagagc catgtggtct ctctggttgt gtatgtccca   1260
ccccagattg gtgagaaatc tctaatctct cctgtggatt cctaccagta cggcaccact   1320
caaacgctga catgtacggt ctatgccatt cctcccccgc atcacatcca ctggtattgg   1380
cagttggagg aagagtgcgc caacgagccc agccaagctg tctcagtgac aaacccatac   1440
ccttgtgaag aatggagaag tgtggaggac ttccagggga gaaataaaat tgaagttaat   1500
aaaaatcaat ttgctctaat tgaaggaaaa aacaaaactg taagtaccct tgttatccaa   1560
gcggcaaatg tgtcagcttt gtacaaatgt gaagcggtca acaaagtcgg gagaggagag   1620
agggtgatct ccttccacgt gaccagggt  cctgaaatta ctttgcaacc tgacatgcag   1680
cccactgagc aggagagcgt gtcttttgtgg tgcactgcag acagatctac gttttgagaac  1740 ctcacatggt acaagcttgg cccacagcct ctgccaatcc atgtgggaga gttgcccaca   1800 cctgttttgca agaacttgga tactctttgg aaattgaatg ccaccatgtt ctctaatagc   1860
acaaatgaca ttttgatcat ggagcttaag aatgcatcct gcaggaccaa aggagactat   1920
gtctgccttg ctcaagacag gaagaccaag aaaagacatt gcgtggtcag gcagctcaca   1980
gtcctagagc gtgtggcacc cacgatcaca ggaaacctgg agaatcagac gacaagtatt   2040
ggggaaagca tcgaagtctc atgcacggca tctgggaatc cccctccaca gatcatgtgg   2100
tttaaagata atgagaccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca ttttttcataa tagaaggtgc ccaggaaaag   2280
acgaacttgg aaatcattat tctagtaggc acgcggtga  ttgccatgtt cttctggcta   2340
cttcttgtca tcatcctacg gaccgttaag cgggccaatg gaggggaact gaagacaggc   2400
tacttgtcca tcgtcatgga tccagatgaa ctcccattgg atgaacattg tgaacgactg   2460
ccttatgatg ccagcaaatg ggaattcccc agagaccggc tgaagctagg taagcctctt   2520
ggccgtggtg cctttggcca agtgattgaa gcagatgcct ttggaattga caagacagca   2580
acttgcagga cagtagcagt caaaatgttg aaagaaggag caacacacag tgagcatcga   2640
gctctcatgt ctgaactcaa gatcctcatt catattggtc accatctcaa tgtggtcaac   2700
cttctaggtg cctgtaccaa gccaggaggg ccactcatgg tgattgtgga attctgcaaa   2760
```

-continued

```
tttggaaacc tgtccactta cctgaggagc aagagaaatg aatttgtccc ctacaagacc    2820 aaagggcac gattccgtca agggaaagac tacgttggag caatccctgt ggatctgaaa    2880
cggcgcttgg acagcatcac cagtagccag agctcagcca gctctggatt tgtggaggag    2940
aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggacctggcg gcacgaaata tcctcttatc ggagaagaac    3120
gtggttaaaa tctgtgactt tggcttggcc cgggatattt ataaagatcc agattatgtc    3180
agaaaaggag atgctcgcct ccctttgaaa tggatggccc cagaaacaat ttttgacaga    3240
gtgtacacaa tccagagtga cgtctggtct tttggtgttt tgctgtggga aatattttcc    3300
ttaggtgctt ctccatatcc tggggtaaag attgatgaag aattttgtag gcgattgaaa    3360
gaaggaacta gaatgagggc ccctgattat actacaccag aaatgtacca gaccatgctg    3420
gactgctggc acggggagcc cagtcagaga cccacgtttt cagagttggt ggaacatttg    3480
ggaaatctct tgcaagctaa tgctcagcag gatggcaaag actacattgt tcttccgata    3540
tcagagactt tgagcatgga agaggattct ggactctctc tgcctacctc acctgtttcc    3600
tgtatggagg aggaggaagt atgtgacccc aaattccatt atgacaacac agcaggaatc    3660
agtcagtatc tgcagaacag taagcgaaag agccggcctg tgagtgtaaa aacatttgaa    3720
gatatcccgt tagaagaacc agaagtaaaa gtaatcccag atgacaacca gacggacagt    3780
ggtatggttc ttgcctcaga agagctgaaa actttggaag acagaaccaa attatctcca    3840
tcttttggtg gaatggtgcc cagcaaaagc agggagtctg tggcatctga aggctcaaac    3900
cagacaagcg gctaccagtc cggatatcac tccgatgaca cagacaccac cgtgtactcc    3960
agtgaggaag cagaactttt aaagctgata gagattggag tgcaaaccgg tagcacagcc    4020
cagattctcc agcctgactc ggggaccaca ctgagctctc ctcctgttta a             4071
```

<210> SEQ ID NO 4
<211> LENGTH: 1356
<212> TYPE: PRT
<213> ORGANISM: Homo sapiens

<400> SEQUENCE: 4

```
Met Gln Ser Lys Val Leu Leu Ala Val Ala Leu Trp Leu Cys Val Glu
1               5                   10                  15

Thr Arg Ala Ala Ser Val Gly Leu Pro Ser Tyr Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Tyr Ser Asp Gln His Gly Val Val Tyr Ile Thr Glu Asn Lys Asn Lys
    130                 135                 140
```

-continued

```
Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
                195                 200                 205

Tyr Gln Ser Ile Met Tyr Ile Val Val Val Gly Tyr Arg Ile Tyr
                210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
                275                 280                 285

Leu Ser Thr Leu Thr Ile Asp Gly Val Thr Arg Ser Asp Gln Gly Leu
290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
                340                 345                 350

Lys Tyr Leu Gly Tyr Pro Pro Glu Ile Lys Trp Tyr Lys Asn Gly
                355                 360                 365

Ile Pro Leu Glu Ser Asn His Thr Ile Lys Ala Gly His Val Leu Thr
                370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
                435                 440                 445

Ala Ile Pro Pro Pro His His Ile His Trp Tyr Trp Gln Leu Glu Glu
                450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
                515                 520                 525

Lys Cys Glu Ala Val Asn Lys Val Gly Arg Gly Glu Arg Val Ile Ser
                530                 535                 540

Phe His Val Thr Arg Gly Pro Glu Ile Thr Leu Gln Pro Asp Met Gln
545                 550                 555                 560
```

-continued

Pro Thr Glu Gln Glu Ser Tyr Ser Leu Trp Cys Thr Ala Asp Arg Ser
            565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
            595                 600                 605

Leu Trp Lys Leu Asn Ala Thr Met Phe Ser Asn Ser Thr Asn Asp Ile
            610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
            645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
            675                 680                 685

Thr Ala Ser Gly Asn Pro Pro Pro Gln Ile Met Trp Phe Lys Asp Asn
            690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Gly Leu Tyr Thr
            725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
            755                 760                 765

Val Gly Thr Ala Val Ile Ala Met Phe Phe Trp Leu Leu Leu Val Ile
            770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
            805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
            835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
            885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
            915                 920                 925

Arg Ser Lys Arg Asn Glu Phe Val Pro Tyr Lys Thr Lys Gly Ala Arg
            930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
            965                 970                 975

Phe Val Glu Glu Lys Ser Leu Ser Asp Val Glu Glu Glu Glu Ala Pro

Glu Asp Leu Tyr Lys Asp Phe Leu Thr Leu Glu His Leu Ile Cys Tyr
     980             985                 990
                995                 1000                1005

Ser Phe Gln Val Ala Lys Gly Met Glu Phe Leu Ala Ser Arg Lys
    1010            1015                1020

Cys Ile His Arg Asp Leu Ala Ala Arg Asn Ile Leu Leu Ser Glu
    1025            1030                1035

Lys Asn Val Val Lys Ile Cys Asp Phe Gly Leu Ala Arg Asp Ile
    1040            1045                1050

Tyr Lys Asp Pro Asp Tyr Val Arg Lys Gly Asp Ala Arg Leu Pro
    1055            1060                1065

Leu Lys Trp Met Ala Pro Glu Thr Ile Phe Asp Arg Val Tyr Thr
    1070            1075                1080

Ile Gln Ser Asp Val Trp Ser Phe Gly Val Leu Leu Trp Glu Ile
    1085            1090                1095

Phe Ser Leu Gly Ala Ser Pro Tyr Pro Gly Val Lys Ile Asp Glu
    1100            1105                1110

Glu Phe Cys Arg Arg Leu Lys Glu Gly Thr Arg Met Arg Ala Pro
    1115            1120                1125

Asp Tyr Thr Thr Pro Glu Met Tyr Gln Thr Met Leu Asp Cys Trp
    1130            1135                1140

His Gly Glu Pro Ser Gln Arg Pro Thr Phe Ser Glu Leu Val Glu
    1145            1150                1155

His Leu Gly Asn Leu Leu Gln Ala Asn Ala Gln Gln Asp Gly Lys
    1160            1165                1170

Asp Tyr Ile Val Leu Pro Ile Ser Glu Thr Leu Ser Met Glu Glu
    1175            1180                1185

Asp Ser Gly Leu Ser Leu Pro Thr Ser Pro Val Ser Cys Met Glu
    1190            1195                1200

Glu Glu Glu Val Cys Asp Pro Lys Phe His Tyr Asp Asn Thr Ala
    1205            1210                1215

Gly Ile Ser Gln Tyr Leu Gln Asn Ser Lys Arg Lys Ser Arg Pro
    1220            1225                1230

Val Ser Val Lys Thr Phe Glu Asp Ile Pro Leu Glu Glu Pro Glu
    1235            1240                1245

Val Lys Val Ile Pro Asp Asp Asn Gln Thr Asp Ser Gly Met Val
    1250            1255                1260

Leu Ala Ser Glu Glu Leu Lys Thr Leu Glu Asp Arg Thr Lys Leu
    1265            1270                1275

Ser Pro Ser Phe Gly Gly Met Val Pro Ser Lys Ser Arg Glu Ser
    1280            1285                1290

Val Ala Ser Glu Gly Ser Asn Gln Thr Ser Gly Tyr Gln Ser Gly
    1295            1300                1305

Tyr His Ser Asp Asp Thr Asp Thr Thr Val Tyr Ser Ser Glu Glu
    1310            1315                1320

Ala Glu Leu Leu Lys Leu Ile Glu Ile Gly Val Gln Thr Gly Ser
    1325            1330                1335

Thr Ala Gln Ile Leu Gln Pro Asp Ser Gly Thr Thr Leu Ser Ser
    1340            1345                1350

Pro Pro Val
    1355

<210> SEQ ID NO 5

<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Anti-human

<400> SEQUENCE: 5

```
gaggttcagc tgcagcagtc tgtggcagag tttgtgaggc caggggcctc agtcaggttg      60
tcctgcacag cttctggctt caacattaaa aacacctata tacactgggt gaggcagagg     120
cctgaacagg gcctggagtg gattggaaag attgatcctg cgaatggtaa tactaaatat     180
gtcccggagt tccagggcaa ggccactatg actgcggaca tcctccaa cacagtctac       240
ctgcacctca gcagcctgac atctgaggac actgccatct attactgtgt cgatggttac     300
tacggctggt atttcgctgt ctggggcaca gggaccacgg tcaccgtctc ctca           354
```

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Anti-human

<400> SEQUENCE: 6

```
Glu Val Gln Leu Gln Gln Ser Val Ala Glu Phe Val Arg Pro Gly Ala
1               5                  10                  15

Ser Val Arg Leu Ser Cys Thr Ala Ser Gly Phe Asn Ile Lys Asn Thr
            20                  25                  30

Tyr Ile His Trp Val Arg Gln Arg Pro Glu Gln Gly Leu Glu Trp Ile
        35                  40                  45

Gly Lys Ile Asp Pro Ala Asn Gly Asn Thr Lys Tyr Val Pro Glu Phe
    50                  55                  60

Gln Gly Lys Ala Thr Met Thr Ala Asp Thr Ser Ser Asn Thr Val Tyr
65                  70                  75                  80

Leu His Leu Ser Ser Leu Thr Ser Glu Asp Thr Ala Ile Tyr Tyr Cys
            85                  90                  95

Val Asp Gly Tyr Tyr Gly Trp Tyr Phe Ala Val Trp Gly Thr Gly Thr
           100                 105                 110

Thr Val Thr Val Ser Ser
        115
```

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Anti-human

<400> SEQUENCE: 7

```
Asn Thr Tyr Ile His
1               5
```

<210> SEQ ID NO 8
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Anti-human

<400> SEQUENCE: 8

Lys Ile Asp Pro Ala Asn Gly Asn Thr Lys Tyr Val Pro Glu Phe Gln
1               5                   10                  15

Gly

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Anti-human

<400> SEQUENCE: 9

Gly Tyr Tyr Gly Trp Tyr Phe Ala Val
1               5

<210> SEQ ID NO 10
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Anti-human

<400> SEQUENCE: 10
caggctgttg tgactcagga atctgcactc accacatcac ctggtgaaac agtcacactc        60
acttgtcgct caagcactgg ggctgttaca actagtaact atgccaactg ggtccaagaa       120
aaaccagatc atttattcac tggtctaata ggtgctacca caaccgagc tccaggtgtt       180 cctgccagat tctcaggctc cctgattgga gacaaggctg tcctcaccat cacaggggca       240
caaactgagg atgaggcaat atatttctgt gctctatggt acagaaacca ttttattttc       300
ggcagtggaa ccaaggtcac tgtcctc                                           327

<210> SEQ ID NO 11
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Anti-human

<400> SEQUENCE: 11

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Ala Thr Asn Asn Arg Ala Pro Gly Val Pro Ala Arg Phe
```

```
                    50                  55                  60
Ser Gly Ser Leu Ile Gly Asp Lys Ala Val Leu Thr Ile Thr Gly Ala
 65                  70                  75                  80

Gln Thr Glu Asp Glu Ala Ile Tyr Phe Cys Ala Leu Trp Tyr Arg Asn
                 85                  90                  95

His Phe Ile Phe Gly Ser Gly Thr Lys Val Thr Val Leu
                100                 105
```

```
<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Anti-human

<400> SEQUENCE: 12

Arg Ser Ser Thr Gly Ala Val Thr Thr Ser Asn Tyr Ala Asn
 1               5                  10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Anti-human

<400> SEQUENCE: 13

Ala Thr Asn Asn Arg Ala Pro
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Anti-human

<400> SEQUENCE: 14

Ala Leu Trp Tyr Arg Asn His Phe Ile
 1               5

<210> SEQ ID NO 15
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45
```

```
Ser Glu Ile Gly Arg Val Gly Val Asn Thr Leu Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Lys Ala Thr Gln Phe Asp Tyr Trp Gly Gln Gly Thr Leu Val
            100                 105                 110

Thr Val Ser Ser
        115

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Tyr Ala Met
1

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Ile Gly Arg Val Gly Val Asn Thr Leu Tyr Ala Asp Ser Val Lys
1               5                  10                  15

Gly Arg Phe Thr Ile
                20

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Ala Thr Gln Phe Asp Tyr
1               5

<210> SEQ ID NO 19
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Arg Ala Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Ile Gly Pro Pro Asp
                 85                  90                  95

Thr Phe Gly Gln Gly Thr Lys Val Glu Ile Lys Arg
            100                 105
```

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Cys Arg Ala Ser Gln Ser Ile Ser Ser Tyr Leu Asn
 1               5                   10
```

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Arg Ala Ser Arg Leu Gln Ser
 1               5
```

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Gln Gln Thr Ile Gly Pro Pro Asp Thr
 1               5
```

<210> SEQ ID NO 23
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Asp Tyr Thr Ser Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Lys Gly Tyr Gly Ala Phe Asp Tyr Trp Gly Gln Gly Thr Leu Val
            100                 105                 110

Thr Val Ser Ser
        115
```

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Ser Tyr Ala Met
1
```

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Gly Ile Ser Gly Ser Gly Asp Tyr Thr Ser Tyr Ala Asp Ser Val Lys
1               5                   10                  15

Gly Arg Phe Thr Ile
            20
```

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Gly Tyr Gly Ala Phe Asp Tyr
1               5
```

<210> SEQ ID NO 27
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Trp Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Ala Asn Tyr Pro Ser
                 85                  90                  95

Thr Phe Gly Gln Gly Thr Lys Val Glu Ile Lys Arg
            100                 105

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ala Ser Gln Ser Ile Ser Ser Tyr Leu Asn
 1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ala Ser Trp Leu Gln Ser
 1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gln Ser Ala Asn Tyr Pro Ser Thr
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Ala Ala Asp Gly Asp Phe
 1               5

<210> SEQ ID NO 32
<211> LENGTH: 7
<212> TYPE: PRT
<213> ORGANISM: Homo sapiens

<400> SEQUENCE: 32

Gly Ser Gly Ser Gly Ser Gly
 1               5

<210> SEQ ID NO 33
<211> LENGTH: 7
```

```
<212> TYPE: PRT
<213> ORGANISM: Homo sapiens

<400> SEQUENCE: 33

Gly Leu Val Ala Ser Asn Leu
1               5

<210> SEQ ID NO 34
<211> LENGTH: 7
<212> TYPE: PRT
<213> ORGANISM: Homo sapiens

<400> SEQUENCE: 34

Pro Gly Glu Cys Leu Arg Val
1               5

<210> SEQ ID NO 35
<211> LENGTH: 7
<212> TYPE: PRT
<213> ORGANISM: Homo sapiens

<400> SEQUENCE: 35

Val Ala Pro Asp Ala Lys Ser
1               5

<210> SEQ ID NO 36
<211> LENGTH: 7
<212> TYPE: PRT
<213> ORGANISM: Homo sapiens

<400> SEQUENCE: 36

Asn Leu Gly Lys Asp Ser Asn
1               5

<210> SEQ ID NO 37
<211> LENGTH: 7
<212> TYPE: PRT
<213> ORGANISM: Homo sapiens

<400> SEQUENCE: 37

Leu His Phe Asn Pro Arg Phe
1               5

<210> SEQ ID NO 38
<211> LENGTH: 7
<212> TYPE: PRT
<213> ORGANISM: Homo sapiens

<400> SEQUENCE: 38

Gly Asp Ala Asn Thr Ile Val
1               5

<210> SEQ ID NO 39
<211> LENGTH: 7
<212> TYPE: PRT
<213> ORGANISM: Homo sapiens

<400> SEQUENCE: 39

Lys Asp Gly Gly Ala Trp Gly
1               5

<210> SEQ ID NO 40
<211> LENGTH: 7
<212> TYPE: PRT
<213> ORGANISM: Homo sapiens
```

<400> SEQUENCE: 40

Arg Glu Ala Val Phe Pro Phe
1               5

<210> SEQ ID NO 41
<211> LENGTH: 7
<212> TYPE: PRT
<213> ORGANISM: Homo sapiens

<400> SEQUENCE: 41

Ser Val Ala Glu Val Cys Ile
1               5

<210> SEQ ID NO 42
<211> LENGTH: 7
<212> TYPE: PRT
<213> ORGANISM: Homo sapiens

<400> SEQUENCE: 42

Gln Ala Asn Leu Thr Val Lys
1               5

<210> SEQ ID NO 43
<211> LENGTH: 7
<212> TYPE: PRT
<213> ORGANISM: Homo sapiens

<400> SEQUENCE: 43

Gly Tyr Glu Phe Lys Phe Pro
1               5

<210> SEQ ID NO 44
<211> LENGTH: 7
<212> TYPE: PRT
<213> ORGANISM: Homo sapiens

<400> SEQUENCE: 44

Asn Leu Glu Ala Ile Asn Tyr
1               5

<210> SEQ ID NO 45
<211> LENGTH: 7
<212> TYPE: PRT
<213> ORGANISM: Homo sapiens

<400> SEQUENCE: 45

Asp Gly Asp Phe Lys Ile Lys
1               5

<210> SEQ ID NO 46
<211> LENGTH: 7
<212> TYPE: PRT
<213> ORGANISM: Homo sapiens

<400> SEQUENCE: 46

Phe Asp Gly Ser Gly Ser Gly
1               5

<210> SEQ ID NO 47
<211> LENGTH: 10
<212> TYPE: PRT
<213> ORGANISM: Homo sapiens

<400> SEQUENCE: 47

Met Ala Cys Gly Leu Val Ala Ser Asn Leu
1               5                   10

<210> SEQ ID NO 48
<211> LENGTH: 10
<212> TYPE: PRT
<213> ORGANISM: Homo sapiens

<400> SEQUENCE: 48

Asn Leu Lys Pro Gly Glu Cys Leu Arg Val
1               5                   10

<210> SEQ ID NO 49
<211> LENGTH: 10
<212> TYPE: PRT
<213> ORGANISM: Homo sapiens

<400> SEQUENCE: 49

Arg Gly Glu Val Ala Pro Asp Ala Lys Ser
1               5                   10

<210> SEQ ID NO 50
<211> LENGTH: 10
<212> TYPE: PRT
<213> ORGANISM: Homo sapiens

<400> SEQUENCE: 50

Phe Val Leu Asn Leu Gly Lys Asp Ser Asn
1               5                   10

<210> SEQ ID NO 51
<211> LENGTH: 10
<212> TYPE: PRT
<213> ORGANISM: Homo sapiens

<400> SEQUENCE: 51

Asn Leu Cys Leu His Phe Asn Pro Arg Phe
1               5                   10

<210> SEQ ID NO 52
<211> LENGTH: 10
<212> TYPE: PRT
<213> ORGANISM: Homo sapiens

<400> SEQUENCE: 52

Asn Ala His Gly Asp Ala Asn Thr Ile Val
1               5                   10

<210> SEQ ID NO 53
<211> LENGTH: 10
<212> TYPE: PRT
<213> ORGANISM: Homo sapiens

<400> SEQUENCE: 53

Cys Asn Ser Lys Asp Gly Gly Ala Trp Gly
1               5                   10

<210> SEQ ID NO 54
<211> LENGTH: 10
<212> TYPE: PRT
<213> ORGANISM: Homo sapiens

<400> SEQUENCE: 54

Thr Glu Gln Arg Glu Ala Val Phe Pro Phe

```
1               5                   10
```

<210> SEQ ID NO 55
<211> LENGTH: 10
<212> TYPE: PRT
<213> ORGANISM: Homo sapiens

<400> SEQUENCE: 55

```
Gln Pro Gly Ser Val Ala Glu Val Cys Ile
1               5                   10
```

<210> SEQ ID NO 56
<211> LENGTH: 10
<212> TYPE: PRT
<213> ORGANISM: Homo sapiens

<400> SEQUENCE: 56

```
Thr Phe Asp Gln Ala Asn Leu Thr Val Lys
1               5                   10
```

<210> SEQ ID NO 57
<211> LENGTH: 10
<212> TYPE: PRT
<213> ORGANISM: Homo sapiens

<400> SEQUENCE: 57

```
Leu Pro Asp Gly Tyr Glu Phe Lys Phe Pro
1               5                   10
```

<210> SEQ ID NO 58
<211> LENGTH: 10
<212> TYPE: PRT
<213> ORGANISM: Homo sapiens

<400> SEQUENCE: 58

```
Asn Arg Leu Asn Leu Glu Ala Ile Asn Tyr
1               5                   10
```

<210> SEQ ID NO 59
<211> LENGTH: 10
<212> TYPE: PRT
<213> ORGANISM: Homo sapiens

<400> SEQUENCE: 59

```
Met Ala Ala Asp Gly Asp Phe Lys Ile Lys
1               5                   10
```

<210> SEQ ID NO 60
<211> LENGTH: 10
<212> TYPE: PRT
<213> ORGANISM: Homo sapiens

<400> SEQUENCE: 60

```
Cys Val Ala Phe Asp Gly Ser Gly Ser Gly
1               5                   10
```

<210> SEQ ID NO 61
<211> LENGTH: 13
<212> TYPE: PRT
<213> ORGANISM: Homo sapiens

<400> SEQUENCE: 61

```
Met Ala Cys Gly Leu Val Ala Ser Asn Leu Asn Leu Lys
1               5                   10
```

<210> SEQ ID NO 62
<211> LENGTH: 13
<212> TYPE: PRT
<213> ORGANISM: Homo sapiens

<400> SEQUENCE: 62

Asn Leu Lys Pro Gly Glu Cys Leu Arg Val Arg Gly Glu
1               5                   10

<210> SEQ ID NO 63
<211> LENGTH: 13
<212> TYPE: PRT
<213> ORGANISM: Homo sapiens

<400> SEQUENCE: 63

Arg Gly Glu Val Ala Pro Asp Ala Lys Ser Phe Val Leu
1               5                   10

<210> SEQ ID NO 64
<211> LENGTH: 13
<212> TYPE: PRT
<213> ORGANISM: Homo sapiens

<400> SEQUENCE: 64

Phe Val Leu Asn Leu Gly Lys Asp Ser Asn Asn Leu Cys
1               5                   10

<210> SEQ ID NO 65
<211> LENGTH: 13
<212> TYPE: PRT
<213> ORGANISM: Homo sapiens

<400> SEQUENCE: 65

Asn Leu Cys Leu His Phe Asn Pro Arg Phe Asn Ala His
1               5                   10

<210> SEQ ID NO 66
<211> LENGTH: 13
<212> TYPE: PRT
<213> ORGANISM: Homo sapiens

<400> SEQUENCE: 66

Asn Ala His Gly Asp Ala Asn Thr Ile Val Cys Asn Ser
1               5                   10

<210> SEQ ID NO 67
<211> LENGTH: 13
<212> TYPE: PRT
<213> ORGANISM: Homo sapiens

<400> SEQUENCE: 67

Cys Asn Ser Lys Asp Gly Gly Ala Trp Gly Thr Glu Gln
1               5                   10

<210> SEQ ID NO 68
<211> LENGTH: 13
<212> TYPE: PRT
<213> ORGANISM: Homo sapiens

<400> SEQUENCE: 68

Thr Glu Gln Arg Glu Ala Val Phe Pro Phe Gln Pro Gly
1               5                   10

<210> SEQ ID NO 69

```
<211> LENGTH: 13
<212> TYPE: PRT
<213> ORGANISM: Homo sapiens

<400> SEQUENCE: 69

Gln Pro Gly Ser Val Ala Glu Val Cys Ile Thr Phe Asp
1               5                   10

<210> SEQ ID NO 70
<211> LENGTH: 13
<212> TYPE: PRT
<213> ORGANISM: Homo sapiens

<400> SEQUENCE: 70

Thr Phe Asp Gln Ala Asn Leu Thr Val Lys Leu Pro Asp
1               5                   10

<210> SEQ ID NO 71
<211> LENGTH: 13
<212> TYPE: PRT
<213> ORGANISM: Homo sapiens

<400> SEQUENCE: 71

Leu Pro Asp Gly Tyr Glu Phe Lys Phe Pro Asn Arg Leu
1               5                   10

<210> SEQ ID NO 72
<211> LENGTH: 13
<212> TYPE: PRT
<213> ORGANISM: Homo sapiens

<400> SEQUENCE: 72

Asn Arg Leu Asn Leu Glu Ala Ile Asn Tyr Met Ala Ala
1               5                   10

<210> SEQ ID NO 73
<211> LENGTH: 13
<212> TYPE: PRT
<213> ORGANISM: Homo sapiens

<400> SEQUENCE: 73

Met Ala Ala Asp Gly Asp Phe Lys Ile Lys Cys Val Ala
1               5                   10
```